United States Patent
Faulkner et al.

(10) Patent No.: US 8,448,516 B2
(45) Date of Patent: May 28, 2013

(54) APPARATUS AND METHOD FOR ASSESSING PERCUTANEOUS IMPLANT INTEGRITY

(75) Inventors: Gary Faulkner, Edmonton (CA); Donald Wayne Raboud, Edmonton (CA); Ryan Clair Swain, Edmonton (CA); Johan Francis Wolfaardt, Edmonton (CA)

(73) Assignee: Covenant Health, Edmonton, Alberta (CA)

( * ) Notice: Subject to any disclaimer, the term of this patent is extended or adjusted under 35 U.S.C. 154(b) by 315 days.

(21) Appl. No.: 12/377,768

(22) PCT Filed: Aug. 17, 2007

(86) PCT No.: PCT/CA2007/001416
§ 371 (c)(1),
(2), (4) Date: Jan. 13, 2011

(87) PCT Pub. No.: WO2008/019489
PCT Pub. Date: Feb. 21, 2008

(65) Prior Publication Data
US 2011/0259076 A1    Oct. 27, 2011

Related U.S. Application Data

(60) Provisional application No. 60/822,686, filed on Aug. 17, 2006.

(51) Int. Cl.
*G01H 13/00* (2006.01)
(52) U.S. Cl.
USPC .......................................................... 73/582
(58) Field of Classification Search
None
See application file for complete search history.

(56) References Cited

U.S. PATENT DOCUMENTS

| | | | |
|---|---|---|---|
| 4,482,324 A | 11/1984 | Wohlgemuth | |
| 5,392,779 A | 2/1995 | Meredith et al. | |
| 5,518,008 A | 5/1996 | Cucchiaro et al. | |
| 5,951,292 A | 9/1999 | Lee et al. | |
| 6,120,466 A | 9/2000 | Earthman | |
| 6,360,602 B1* | 3/2002 | Tazartes et al. | 73/514.18 |
| 2004/0096803 A1* | 5/2004 | Huang et al. | 433/150 |

OTHER PUBLICATIONS

Notes_8, GEOS 585A, Spring 2009, http://www.ltrr.arizona.edu/~dmeko/notes_8.pdf, 10 pages in total.
International Search Report for PCT/CA2007/001416, Nov. 30, 2007, 2 pages in total.

* cited by examiner

*Primary Examiner* — Robert R Raevis
(74) *Attorney, Agent, or Firm* — Bennett Jones LLP

(57) ABSTRACT

Provided is an apparatus for assessing interface integrity between a medium and an implant. A first signal is translated from a motion of an impact body during impact with an abutment connected to the implant. In some embodiments, the first signal is filtered using a zero phase shift filter and then used for assessing the interface integrity. Since no phase shift is introduced, the interface integrity is accurately assessed. In another embodiment, the apparatus maintains a system model for impacting the impact body against the abutment. The apparatus analytically determines an interface property by applying a system property that has been determined to the system model. An accurate system model allows for an accurate assessment. According to another broad aspect, there is provided a method of conducting the impact test. According to the method, a person ensures that the impact body impacts against a consistent portion of the abutment.

27 Claims, 55 Drawing Sheets

The Periotest rod strikes the implant/abutment system in A, they both deflect to a maximum deflection as seen in B, the rod/implant/abutment return to their initial strike position at C, and then the rod loses contact and returns into the hand piece.

Typical Implant/Abutment System

The Periotest rod strikes the implant/abutment system in A, they both deflect to a maximum deflection as seen in B, the rod/implant/abutment return to their initial strike position at C, and then the rod loses contact and returns into the hand piece.

Typical Accelerometer Signal

Testing Apparatus for *In Vitro* Model

Moving average filtered signal and Periotest signal for a 10mm implant with a 3mm abutment.

Comparison of contact times in micro-seconds (μs) of the moving average filtered signal to the Periotest signal.

Strain gauge, moving average filtered and Periotest signal readings for a 4mm implant with 5.5mm abutment. This plot demonstrates that the moving average signal contact time realistically represents the motion of the system, while the Periotest signal does not.

Measurements on the repeatability and reproducibility of the experimental setup.

Schematic of Simplified *In Vitro* Model

Finite Element Model Used for Impact Analysis

Typical Transient Analysis Signal

First Natural Frequency Comparison for Oral Implants

Second Natural Frequency Comparison for Oral Implants

Second Natural Frequency Comparison for BAHA Implants

First Mode Response to Changing Interface Stiffness – Oral Implant

Second Mode Response to Changing Interface Stiffness – Oral Implant

First Mode Response to Changing Interface Stiffness – BAHA Implant

Four degree of freedom model.

Effect of Hand Piece Distance from abutment on resonant frequency. No noticeable difference between distances were found.

Effect of abutment torque on the resonant frequency of a 5.5mm abutment with a 4mm implant.

Effect of striking height on resonant frequency. Natural frequency increases very significantly as the abutment is hit lower from the top. This highlights the importance of controlling where the rod strikes when using the instrument.

Effect of angulation on the resonant frequency readings. If angulation is kept between 1-5° there is very little change in the readings.

APPARATUS AND METHOD FOR ASSESSING PERCUTANEOUS IMPLANT INTEGRITY

RELATED APPLICATION

This application claims the benefit of and is a National Phase Entry of International Application Number PCT/CA2007/001416 filed Aug. 17, 2007, and claims the benefit of U.S. Provisional Patent Application No. 60/822,686 filed Aug. 17, 2006, which is hereby incorporated by reference in its entirety.

FIELD OF THE INVENTION

This invention relates to techniques for assessing percutaneous implant integrity, and in particular to careful control of conditions under which impact-style techniques are utilised, and the analysis of data received therefrom.

BACKGROUND OF THE INVENTION

Osseointegrated implants are routinely utilized in a broad range of oral and extraoral applications including removable and fixed dental prostheses, in re-construction of the head and neck, as a transmission path for bone anchored hearing aids (BAHA™), to provide anchorage in orthodontic treatment and in orthopedic applications. FIG. 1 shows a cross-sectional side view of a typical in-situ implant and abutment system. Such implants are typically 3-6 mm in diameter and range in length from 3-4 mm (BAHA and orbit applications) to 7-20 mm (dental reconstructions). Such implants are often formed of Titanium.

The success of these implants is dependent on the quality of the bone-implant bond at the interface of the implant. A direct structural and functional connection between living bone and the surface of a load-carrying implant is defined as osseointegration. This process typically begins immediately after the implant has been installed. If this does not occur, the development of connective soft tissue in the bone-implant interface may begin and can lead to failure of the implant. The status of the implant-bone interface during this crucial time is extremely important in evaluating when the implant can be put into service (loaded) or whether further healing is necessary.

In addition, over time osseointegration can deteriorate and/or the degree of bone in contact with the implant surface can reduce. Although implant survival rates are high in many applications, it is important to be able to determine if any change in the health of this interface occurs. As a result of these potential clinical conditions, there is an ongoing desire to monitor the "health" or integrity of the bone-implant interface from initial installation of the implant throughout the life of the implant.

Conventional diagnostic techniques, such as radiography and magnetic resonance imaging, are generally able to evaluate bone quantity and in some cases may provide parameters that relate to bone quality (eg. Hounsfield radiodensity scale). However, these techniques are limited in their ability to monitor the actual bone-implant interface, as the implant tends to shield this region resulting in poor image resolution in this vital area. Therefore, the condition of the bone-implant interface including the implant threads and the adjacent tissue undergoing remodelling is much more difficult to evaluate. When using radiography, the changes in bone are often well advanced before becoming evident on radiographic images. Furthermore, images obtained in this manner are costly and high quality radiographs carry additional risks associated with radiation exposure.

Other techniques such as measuring removal torque are too invasive to be used in either the operating room or for clinical visits. As a result, dynamic mechanical testing methods have been proposed and are presently in use. These mechanical techniques are all, in one form or another, based on determining the resonant frequency of the implant-tissue system including the transducer. As the resonant frequency is dependent on the manner in which the implant is supported by the surrounding biological tissue, changes in this resonant frequency (perhaps coupled with changes in the internal damping) should be linked to changes in the status of this interface. This, of course, assumes that there are no other changes in the implant system (such as a loosening of the abutment/implant joint) that may overshadow those in the interface.

Presently, the primary commercially available system developed specifically for monitoring implants is Osstell™, which employs a transducer attached to the abutment or directly to the implant. The transducer excites the system over a range of frequencies while simultaneously monitoring the resulting transducer motion to determine the resonant frequency of the overall implant/transducer or implant/abutment/transducer system. The results of several investigations using this system have reported varying degrees of success in identifying changes in the implant status. A disadvantage of the Osstell is that it is designed to be used with retrievable systems only.

Alternative techniques to the Osstell are based on transient measurements in which the abutment is excited using an external impact. Subsequently, a measurement method was developed that utilised an instrumented impact hammer to evaluate the mechanical impedance variations caused by interface changes. One approach involved an impacting rod to excite the abutment and the resulting resonant frequency was determined from an acoustic signal obtained from a microphone mounted in close proximity.

Another system that has been used is the Periotest™, which was originally developed to measure the mobility of natural dentition. As shown in FIG. 2, there is a Periotest handpiece, which contains a metal rod of approximately 9 grams. The metal rod is accelerated towards the implant-abutment via an electromagnet. The acceleration response of the rod, while in contact with the implant-abutment, is measured using an accelerometer attached to the rear of this rod. In particular, the acceleration signal is used to determine the period of time during which the rod and tooth remain in contact. This period of time is indicative of the integrity of the tooth interface.

There are benefits to the Periotest system. The Periotest handpiece provides a convenient means to dynamically excite the implant abutment system in areas that may be too cramped to utilise Osstell or impact hammer devices. Also, the Periotest handpiece can be used on implant abutment systems with non-recoverable, cemented restorations. As well, the output signal from the accelerometer may contain information unavailable to the RFA systems, which can be more completely utilised to determine the status of the interface layer. For example, the handpiece has recently been adapted for use in a system designed to measure the damping capacity of materials.

Several researchers have attempted to adopt the Periotest in monitoring the integrity of artificial implants instead of natural teeth. The results of these investigations have shown varying degrees of success. When used to monitor the mobility of natural teeth, the contact time is not used directly but is used to calculate a so-called Periotest value (PTV) which was originally chosen to correspond to the established Miller Mobility Index for natural teeth. For natural teeth, which are supported by periodontal ligaments, the PTV's range is from approximately −8 to 50 with −8 representing a tooth with a very stiff supporting structure and a PTV of 50 corresponds to a tooth which is noticeably loose and moveable by finger pressure.

When used to measure artificial implants the contact times involved correspond to PTV's that are significantly lower than for natural teeth, as the bone to implant interface provides a much stiffer supporting structure than periodontal ligaments. Since the Periotest has a built in lower PTV limit of −8 and only produces integer values, there is a limited range of PTV readings available for a typical implant application. For example, it has been found that well integrated implants have a range of PTV values between −7 and 0 in the mandible and −7 to +1 in the maxilla at the time of abutment connection. This limited range does not provide enough resolution to monitor subtle changes in the bone-implant interface over time. The Periotest system cannot accurately determine a contact time for very stiff implant interfaces, especially for those that are extraoral.

BRIEF DESCRIPTION OF THE DRAWINGS

FIGS. 41A and 42B are graphs comparing model to measurement values with and without a flange;

SUMMARY OF THE INVENTION

Figure 1:
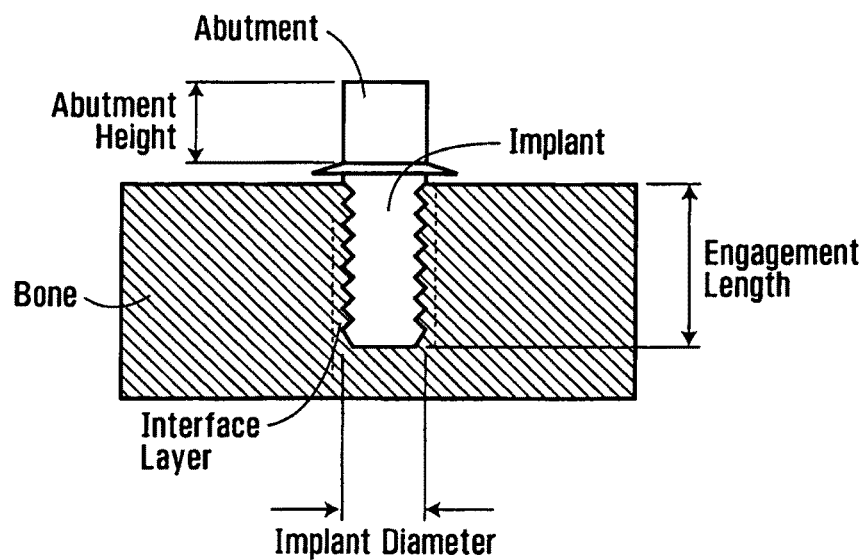
FIG. 1 is a cross-sectional side view of a typical in-situ implant and abutment system.
Figure 2:
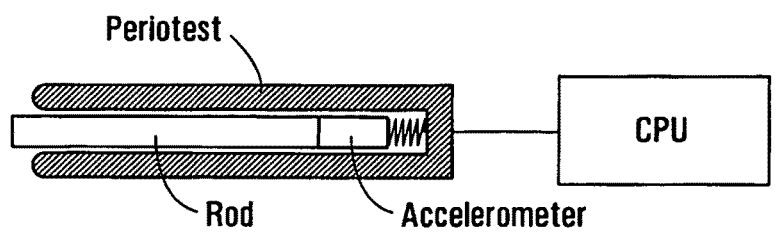
FIG. 2 is a cross-sectional side view of a typical Periotest system.

According to a broad aspect, there is provided an apparatus for processing a signal for determining an indication of an interface integrity between a medium and an implant that is at least partially embedded therein, the apparatus comprising: an input for receiving a first signal generated from a motion of an impact body during impact with an abutment connected to the implant; and a zero phase shift filter for filtering the first signal thereby generating a filtered signal to be used for determining the indication of the interface integrity.

According to another broad aspect, there is provided a method of processing a signal for determining an indication of an interface integrity between a medium and an implant that is at least partially embedded therein, the method comprising: receiving a first signal generated from a motion of an impact body during impact with an abutment connected to the implant; and filtering the first signal using a zero phase shift filter thereby generating a filtered signal to be used for determining the indication of the interface integrity.

According to another broad aspect, there is provided a computer readable medium having computer executable instructions stored thereon for execution on a processor so as to implement the method summarised above.

According to another broad aspect, there is provided an apparatus for determining a property of an interface between a medium and an implant that is at least partially embedded therein, the apparatus comprising: an input for receiving a signal generated from a motion of an impact body during impact with an abutment connected to the implant; and a property determiner for: (a) maintaining a mathematical model for impacting the impact body against the abutment; (b) determining a system property from the signal; and (c) analytically determining the property of the interface by applying the system property to the mathematical model.

According to another broad aspect, there is provided a method of determining a property of an interface between a medium and an implant that is at least partially embedded therein, the method comprising: maintaining a mathematical model for impacting an impact body against an abutment connected to the implant; receiving a signal generated from a motion of the impact body during impact with the abutment; determining a system property based on the signal; and analytically determining the property of the interface by applying the system property to the mathematical model.

According to another broad aspect, there is provided a computer readable medium having computer executable instructions stored thereon for execution on a processor so as to implement the method summarised above.

According to another broad aspect, there is provided a method of conducting an impact test to assess integrity of a plurality of implants using an impact-type testing system, each implant being at least partially embedded in a medium and having an abutment connected thereto, the method comprises: impacting an impact body against each abutment; and ensuring that the impact body impacts against each abutment at a consistent portion of the abutment.

According to another broad aspect, there is provided a method of conducting impact tests to assess integrity of an implant over time using an impact-type testing system, the implant being at least partially embedded in a medium and having an abutment connected thereto, the method comprises: from time to time, conducting an impact test by impacting an impact body against the abutment; and ensuring that the impact body impacts against the abutment at a consistent portion of the abutment for each impact test.

According to another broad aspect, there is provided a calibration block comprising: a medium; and a plurality of systems, each system comprising a respective implant embedded in the medium and a respective abutment connected to the implant; wherein each system has a predetermined nominal value for a system property.

DETAILED DESCRIPTION OF EMBODIMENTS

While the methods of the present invention are described in the context of an impact test conducted on an abutment attached to an artificial implant, it is to be understood that these methods may also be employed in the context of natural dentition. Thus, in this specification, the term "abutment" includes the crown of a natural tooth, while "implant" includes the root of a tooth. It is also to be understood that the present invention is applicable to replacement teeth. In such applications, the "implant" is synthetic and might for example be formed of titanium. The "abutment" connected to the implant is also synthetic and is typically designed to function as a tooth crown.

Section I: Zero Phase Shift Filter

Introduction

Figure 3:
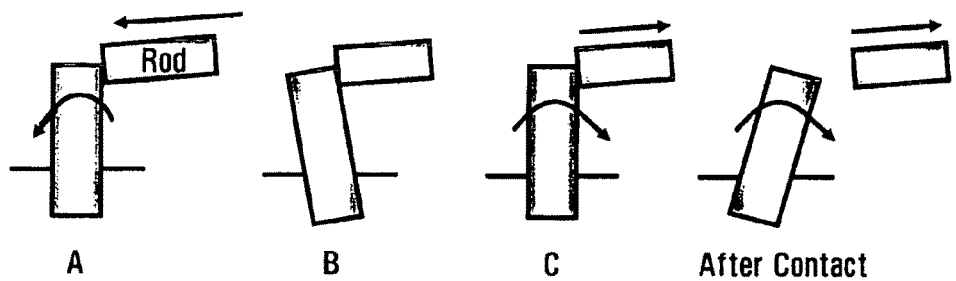
FIG. 3 is a schematic drawing of a Periotest rod striking an implant abutment.

Referring now to FIG. 3, shown is a schematic drawing of a Periotest rod striking an implant abutment. At point A, the Periotest rod strikes the implant abutment. The Periotest rod and the implant abutment remain in contact through points B and C. At point C the accelerometer signal reaches zero. The interval between A and C is termed the contact time and is indicative of the integrity of the implant interface. The Periotest system measures the contact time in order to access the integrity of the implant interface, but as noted above, the resolution of the Periotest system is limited.

The limited resolution of the Periotest system is further compounded by the fact that the Periotest unit does not base the contact time on the accelerometer signal directly. Instead, the accelerometer signal is first conditioned using a filter to smooth the signal. The contact time is then based on this filtered signal. However, the filter used can produce a noticeable and significant phase shift in the accelerometer signal, which introduces a distortion of the contact time.

Figure 4:
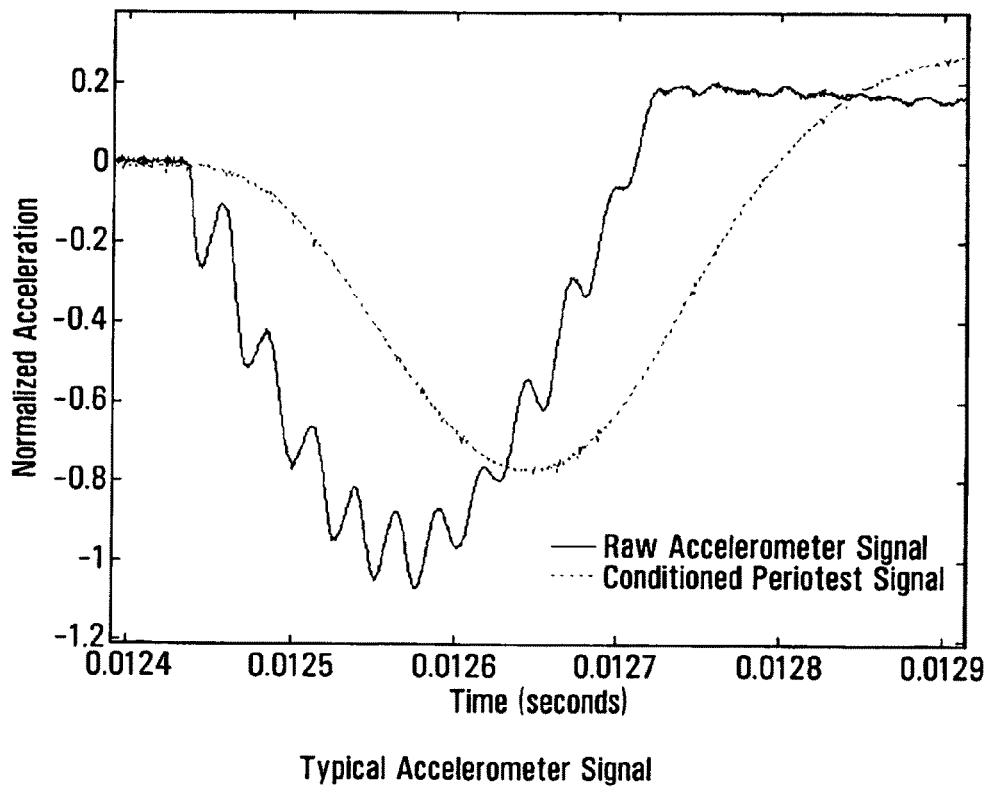
FIG. 4 is a graph showing typical raw and conditioned Periotest signals.

In the Periotest system, the accelerometer signal is filtered and processed to yield a quantitative measure of mobility related to the Miller Mobility Index for natural dentition. An example of the signal before and after filtering is shown in FIG. 4 for the corresponding motion of the implant and rod shown in FIG. 3. There are two major differences between the conditioned and unconditioned signals in FIG. 4. A comparison of the two signals shows the unconditioned having a distinct higher frequency component that has been removed in the conditioning. In addition, the time for the acceleration to return to zero is considerably longer for the conditioned than the unconditioned signal.

The differences between the conditioned and unconditioned signals suggest that perhaps the filtering discards information that could be used for a more complete diagnosis. Also, the differences suggest that the filtering alters the fundamental time (to return to zero acceleration) used to calculate the response in terms of a so-called Periotest value (PTV). While these differences may not be significant for natural dentition, as the range of PTV values is relatively large (−6 to 50), they have more significance for implant-abutment systems where the majority of results have PTV's over a much more limited range (−8 to 2).

The possibility of using the impact technique of the Periotest system to more precisely monitor the status of the bone to implant interface has been investigated. An issue to consider is whether variables such as osseointegration levels and loss of bone margin height have an appreciable effect on the overall response. To investigate these issues, the raw accelerometer signal such as the one shown in FIG. 4 has been investigated.

System and Method

Figure 5:
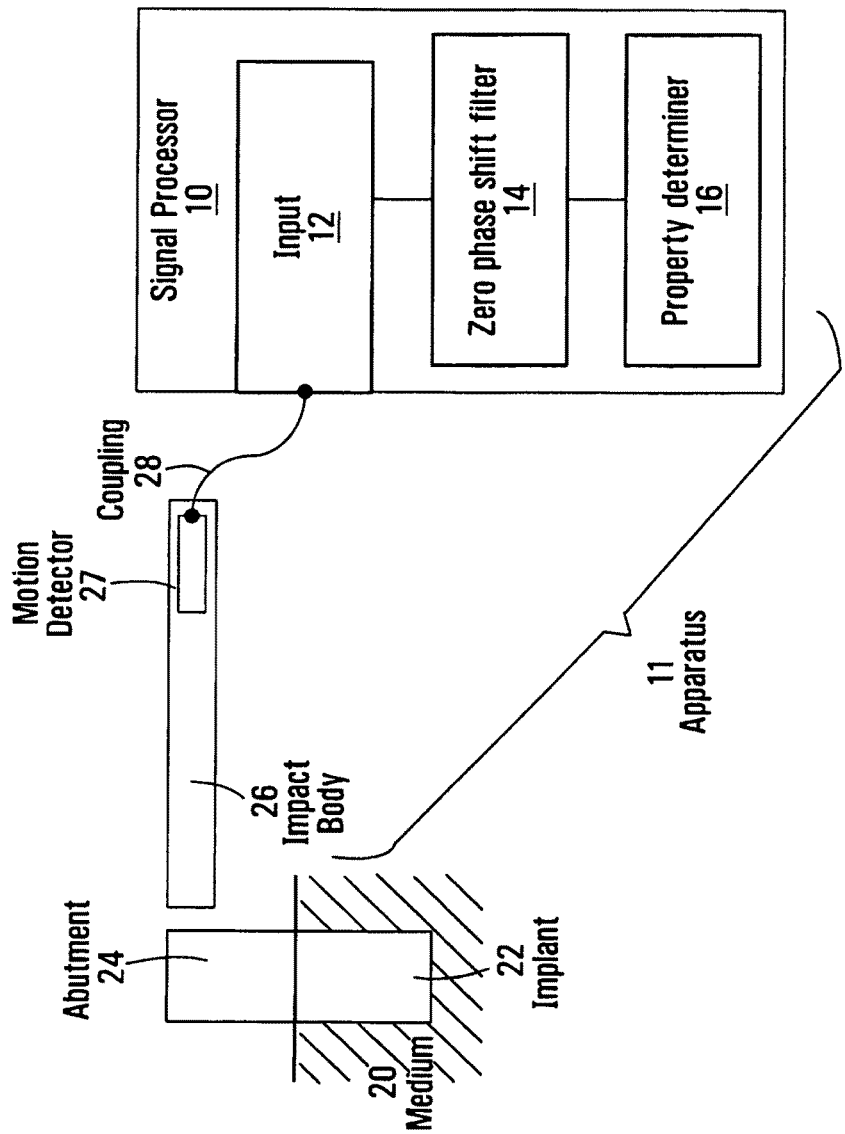
FIG. 5 is a schematic of an apparatus for determining an indication of an interface integrity between a medium and an implant that is at least partially embedded therein.

Turning now to FIG. 5, shown is a schematic of an apparatus 11 for determining an indication of an interface integrity between a medium 20 and an implant 22 that is at least partially embedded therein. An abutment 24 is connected to the implant 22. The apparatus 11 has a signal processor 10 connected to an impact body 26 via a coupling 28. The impact body 26 has a motion detector 27, which might for example be an accelerometer. The signal processor 10 has an input 12, a zero-phase shift filter 14, and a property determiner 16. The apparatus 11 may have other components, but they are not shown for sake of simplicity.

In operation, a user impacts the impact body 26 against the abutment 24. The impact body 26 might be accelerated towards the abutment 24 for example via an electromagnet. The motion detector 27 translates the motion of the impact body 26 during impact into a first signal, which is provided to the signal processor 10 over the coupling 28. The coupling 28 is a wired connection, but in alternative implementations might be a wireless connection. The signal processor 10 receives the first signal over the input 12. According to an embodiment of the invention, the first signal is filtered with the zero phase shift filter 14 thereby generating a filtered signal to be used for determining the indication of the interface integrity. The property determiner 16 determines the indication of the interface integrity based on the filtered signal. Since no phase shift is introduced, the indication of the interface integrity can be accurately determined from the filtered signal.

There are many possibilities for the zero-phase shift filter 14. In some implementations, the zero-phase shift filter 14 is a moving average filter. In other implementations, the zero-phase shift filter 14 is a symmetrical filter such as a Gaussian filter or a Hamming filter. Other zero-phase shift filters are possible. Additionally, many digital filters that introduce a phase shift (such as a Butterworth filter for example) can be made to be zero-phase by applying the filter on the data a second time but in reverse order. More generally, a "zero-phase shift filter" can include any appropriate combination of components that provide suitable filtering with a zero net phase shift. Other implementations are possible. Note that a "zero-phase shift filter" ideally introduces no phase shift at all, but in practical implementations might introduce a very small amount of phase shift. Therefore, a zero-phase shift filter is characterised in that it introduces no meaningful phase shift. Any phase shift introduced by such a filter is not detectable or is negligible for the purposes described herein.

It is to be understood that the "abutment connected to the implant" does not necessarily mean that the abutment and the implant are formed of separate members. In some implementations, the abutment and the implant are formed of a same continuous member. In this manner, although the abutment and the implant are referred to separately, they are still part of the same continuous member. In other implementations, the abutment and the implant are formed of separate members.

There are many possibilities for the indication of the interface integrity. In some implementations, the indication is an explicit indication of the interface integrity. In these implementations, a measure of the interface integrity is determined by the property determiner 16. In other implementations, the indication is an implicit indication of the interface integrity. In these implementations, a measure of the interface integrity may not have been determined, but at least a variable or parameter has been determined that is indicative of the interface integrity. Such variable or parameter might for example be the contact time or the natural frequency of the system. Note that the contact time and the natural frequency of the system are not explicit measures of the interface integrity, but are still indicative of the interface integrity.

There are many ways for the property determiner 16 to determine the indication of the interface integrity. In some implementations, the property determiner 16 determines a natural frequency of the system based on a contact time measured from the filtered signal. Note that since no phase shift is introduced, the indication of the contact time can be accurately determined from the filtered signal. Upon determining the contact time, the natural frequency of the system can be determined. Finally, the property of the interface can be determined based on the natural frequency. In some implementations, this is performed by applying the natural frequency to predetermined correlations or look-up tables. In other implementations, this is performed by applying the natural frequency to a predetermined mathematical model for the system. Note that the "system" includes many components such as the implant 22 and the abutment 24, and may include other components and/or considerations depending on the complexity of the model. Further details of system modelling are provided later.

In the illustrated example, signal processing is performed by the signal processor 10. More generally, signal processing can be implemented by hardware, firmware, software, or any appropriate combination thereof. For software implementations, there is provided a computer readable medium having computer executable instructions stored thereon for execution on a processor for implementing functionality described herein.

Figure 6:
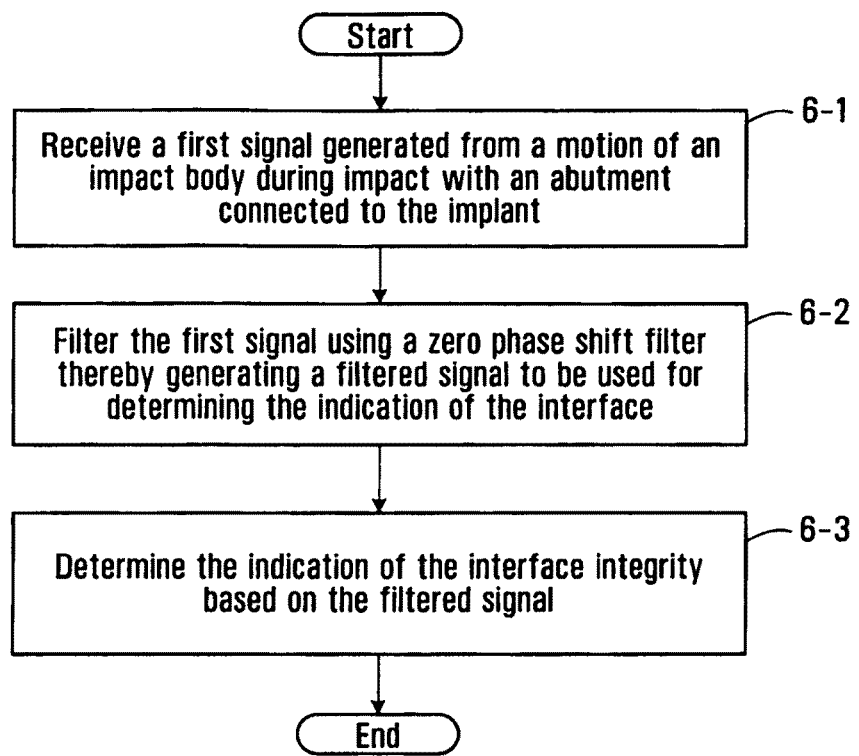
FIG. 6 is a flowchart of a method of processing a signal for determining an indication of an interface integrity between a medium and an implant that is at least partially embedded therein.

Referring now to FIG. 6, shown is a flowchart of a method of processing a signal for determining an indication of an interface integrity between a medium and an implant that is at least partially embedded therein. This method can be implemented by a signal processor, for example by the signal processor 10 shown in FIG. 5. More generally, this method may be implemented in any appropriate apparatus.

At step 6-1, the apparatus receives a first signal generated from a motion of an impact body during impact with an abutment connected to the implant. According to an embodiment of the invention, at step 6-2 the apparatus filters the first signal using a zero phase shift filter thereby generating a filtered signal to be used for determining the indication of the interface integrity. Examples of zero phase shift filters that can be used have been described above. At step 6-3, the apparatus determines the indication of the interface integrity based on the filtered signal. Examples for the indication of the interface integrity have been provided above. Since no phase shift is introduced, the indication of the interface integrity can be accurately determined from the filtered signal. Examples of how this might be accomplished have been provided above.

In the examples described above with reference to FIGS. 5 and 6, it is assumed that the zero-phase shift filter and the property determiner are implemented by the same component. In alternative implementations, they are implemented separately. For example, the zero-phase shift filter might be included as part of the impact body. An example of this is described below with reference to FIGS. 7 and 8. Other implementations are possible. For example, all of the signal processing could be performed by hardware that is part of the impact body. For such implementations, there is no need for a separate processor coupled to the impact rod.

Another System and Method

Figure 7:
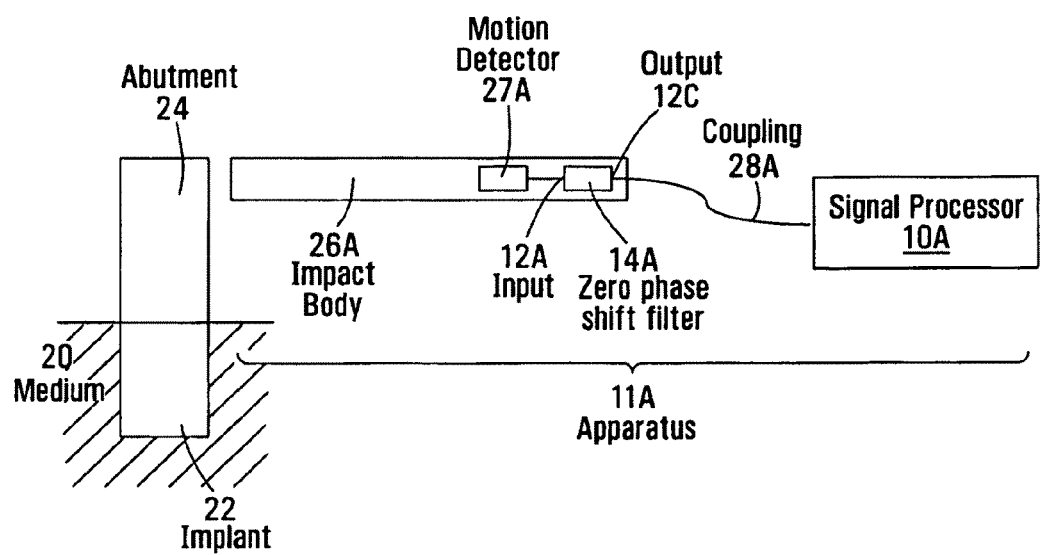
FIG. 7 is a schematic of another apparatus for determining an indication of an interface integrity between the medium and the implant that is at least partially embedded therein.

Turning now to FIG. 7, shown is a schematic of another apparatus 11A for determining an indication of an interface integrity between the medium 20 and the implant 22 that is at least partially embedded therein. The apparatus 11A has a signal processor 10A connected to an impact body 26A via a coupling 28A. The impact body 26A has a motion detector 27A, which might for example be an accelerometer, and a zero-phase shift filter 14A. The zero-phase shift filter 14A has an input 12A and an output 12C. The signal processor 10A is not shown with any components for sake of simplicity. The apparatus 11A may have other components, but they are not shown for sake of simplicity.

In operation, a user impacts the impact body 26A against the abutment 24. The impact body 26A might be accelerated towards the abutment 24 for example via an electromagnet. The motion detector 27A translates the motion of the impact body 26A during impact into a first signal. According to an embodiment of the invention, the first signal is filtered with the zero phase shift filter 14A thereby generating a filtered signal to be used for determining the indication of the interface integrity. Examples of zero phase shift filters that can be used have been described above. The filtered signal is provided over the coupling 28A to another entity that determines the indication of the interface integrity based on the filtered signal. The coupling 28A is a wired connection, but in alternative implementations might be a wireless connection. In this example, the "other entity" is the signal processor 10A. The property signal processor 10A determines the indication of the interface integrity based on the filtered signal. Examples for the indication of the interface integrity have been provided above. Since no phase shift is introduced, the indication of the interface integrity can be accurately determined from the filtered signal. Examples of how this might be accomplished have been provided above.

In the illustrated example, the zero-phase filter 14A is implemented as hardware. More generally, the zero-phase filter 14A can be implemented by hardware, firmware, software, or any appropriate combination thereof. For software implementations, there is provided a computer readable medium having computer executable instructions stored thereon for execution on a processor for implementing functionality described herein.

Figure 8:
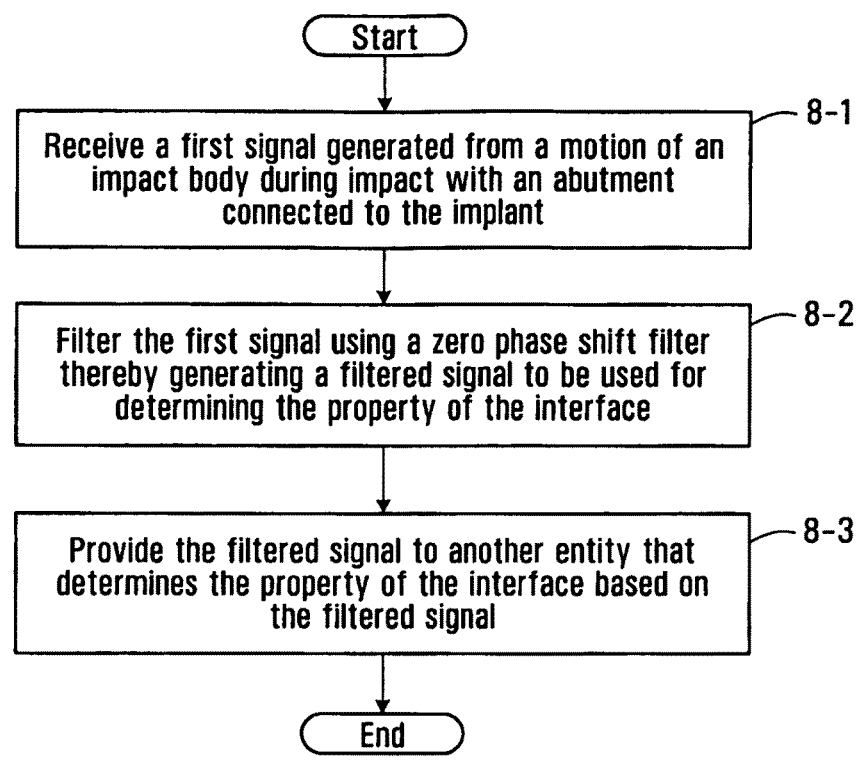
FIG. 8 is a flowchart of another method of processing a signal for determining an indication of an interface integrity between a medium and an implant that is at least partially embedded therein.

Referring now to FIG. 8, shown is a flowchart of another method of processing a signal for determining an indication of an interface integrity between a medium and an implant that is at least partially embedded therein. This method can be implemented by an impact body, for example by the zero-phase shift filter 14A of the impact body 26A shown in FIG. 7. More generally, this method may be implemented in any appropriate apparatus.

At step 8-1, the apparatus receives a first signal generated from a motion of an impact body during impact with an abutment connected to the implant. According to an embodiment of the invention, at step 8-2 the apparatus filters the first signal using a zero phase shift filter thereby generating a filtered signal to be used for determining the indication of the interface integrity. Examples of zero phase shift filters that can be used have been described above. At step 8-3, the apparatus provides the filtered signal to another entity that determines the indication of the interface integrity based on the filtered signal. Examples for the indication of the interface integrity have been provided above. Since no phase shift is introduced, the indication of the interface integrity can be accurately determined from the filtered signal. Examples of how this might be accomplished have been provided above.

Testing Apparatus

Figure 9:
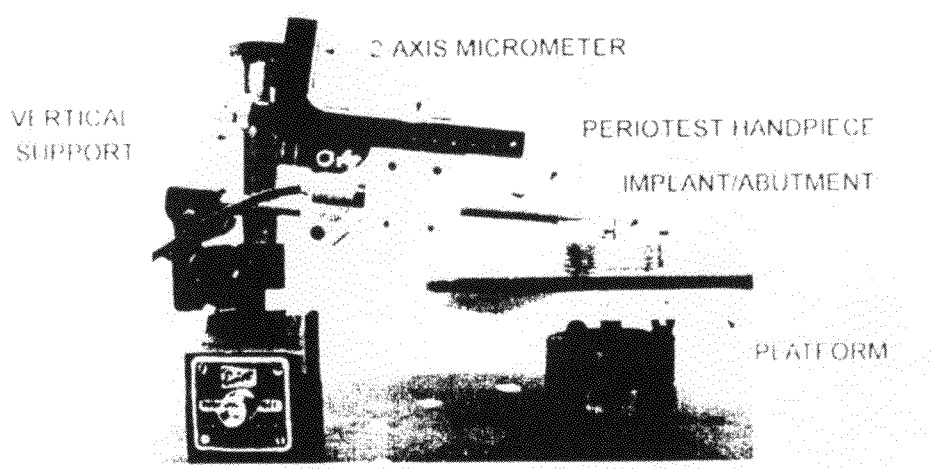
FIG. 9 is a photograph of a testing apparatus for an in vitro model.

Referring now to FIG. 9, shown is a photograph of a testing apparatus for an in vitro model. A disk is clamped in a circular trough which is in turn mounted in a clamping device that also supports the clamped Periotest handpiece. The clamped handpiece is mounted on a microscope stage to allow adjustment of the position of the rod relative to the abutment.

To simulate bone anchored implants, two implant/abutment systems were chosen to simulate a range of implant applications. The implants used were a 4 mm flanged extra-oral implant (4 mm×Ø 3.75 mm, SEC 002-0, Entific Medical Systems, Toronto, Ontario, Canada) and a 10 mm intra-oral implant (10 mm×Ø 3.75 mm, Nobel Biocare, Toronto, Ontario, Canada). The implants were mounted in 41 mm diameter discs of Photoelastic FRB-10 plastic (Measurements Group Inc., Raleigh N.C., USA). Implants were installed into the discs by drilling an appropriate diameter hole and then cutting threads using a tap matched to the implant. The 4 mm implant was inserted into a disc of 5 mm thickness while the 10 mm implant was in a 10 mm thick disc. Both implants were secured to the discs with epoxy cement (5 Minute Epoxy, Devcon, Danvers, Mass., USA) to ensure as uniform an interface as possible. FRB-10 was chosen as its elastic modulus of 9.3 GPa is of the same order as that reported for cortical bone and for dense cancellous bone (1.3-25.8 GPa).

Two different abutments were used in the experiments, a standard 5.5 mm (SDCA 005-0, Nobel Biocare, Toronto, Ontario, Canada), and a standard 10 mm abutment (SDCA 043-0, Nobel Biocare, Toronto, Ontario, Canada). The abutments were attached to the implants using a torque wrench (DIB 038, Nobel Biocare, Toronto, Ontario, Canada) and torqued to 20 Ncm unless otherwise specified. The FRB discs were then mounted in a circular steel base that was in turn mounted to a stand which also held the Periotest handpiece.

The Periotest handpiece was mounted on a custom built adjustable stand that allowed for vertical, horizontal and angular rotations of the handpiece. The holder had two micrometer attachments (Vickers Instrument Ltd., England) to control the horizontal and vertical displacements. Handpiece angulation was measured using a standard bevel gauge (not shown). The implant and abutment were formed of a single aluminum post.

Mechanical properties and sizes of the components are given in Table 1 and Table 2.

TABLE 1

Model Dimensions

| Oral Model Dimensions | | | |
|---|---|---|---|
| Post Radius ($P_r$) | 2 mm | Post Height ($P_h$) | 20 mm |

TABLE 1-continued

| Model Dimensions | | | |
|---|---|---|---|
| Abutment Heigh ($A_h$) | 10 mm | Engagement Length ($E_L$) | 9 mm |
| Interface Thickness ($I_t$) | 0.38 mm | Interface Height ($I_h$) | 9 mm |
| Disk Radius ($D_r$) | 20 mm | Disk Height ($D_h$) | 9 mm |
| Periotest ® Rod Signal ($R_r$) | 1 mm | Periotest ® Rod Length ($R_L$) | 20 mm |
| BAHA Model Dimensions | | | |
| Post Radius ($P_r$) | 2 mm | Post Height ($P_h$) | 20 mm |
| Abutment Height ($A_h$) | 5 mm | Engagement Length ($E_L$) | 4 mm |
| Interface Thickness ($I_t$) | 0.38 mm | Interface Height ($I_h$) | 9 mm |
| Disk Radius ($D_r$) | 20 mm | Disk Height ($D_h$) | 9 mm |
| Periotest ® Rod Radius ($R_r$) | 1 mm | Periotest ® Rod Length ($R_L$) | 20 mm |

TABLE 2

| Model Properties | | | |
|---|---|---|---|
| Component | Young's Modulus (GPa) | Poisson's Ratio | Density (kg/m³) |
| FRB Disk | 8.4 | 0.31 | 1800 |
| Aluminium Post | 73 | 0.32 | 2800 |
| Acrylic Interface Layer | 0.5 | 0.30 | 1800 |
| Periotest ® Rod | 200 | 0.30 | 9.4 grams |

To measure the Periotest signal and the un-modified acceleration signal simultaneously, a DAP 5400a sampling card (Microstar Laboratories, Bellevue, Wash., USA) with a sampling rate of 2 MHz was used. The un-modified acceleration signal collected from the Periotest handpiece was filtered by a moving average filter, so as not to introduce phase shift and distortion of the contact time. After filtering, the contact time was measured. The fundamental mode dominates the response and with the removal of higher frequency components in the signal the contact times calculated serve as an approximation of the half period of vibration of the system's first mode during impact. The resonant frequency of the system was then calculated using $$Freq = \frac{1}{2 \cdot (ContactTime)}$$

To measure the extent of the differences between the moving average filtered signal and the Periotest signal the contact times for three different systems have been evaluated:

4 mm implant with a 10 mm abutment to simulate a less stiff system (longer contact time), 10 mm implant with a 3 mm abutment to simulate a stiff system (shorter contact time), and 10 mm implant with a 10 mm abutment to evaluate the intermediate case.

Results of Testing

Figure 10:
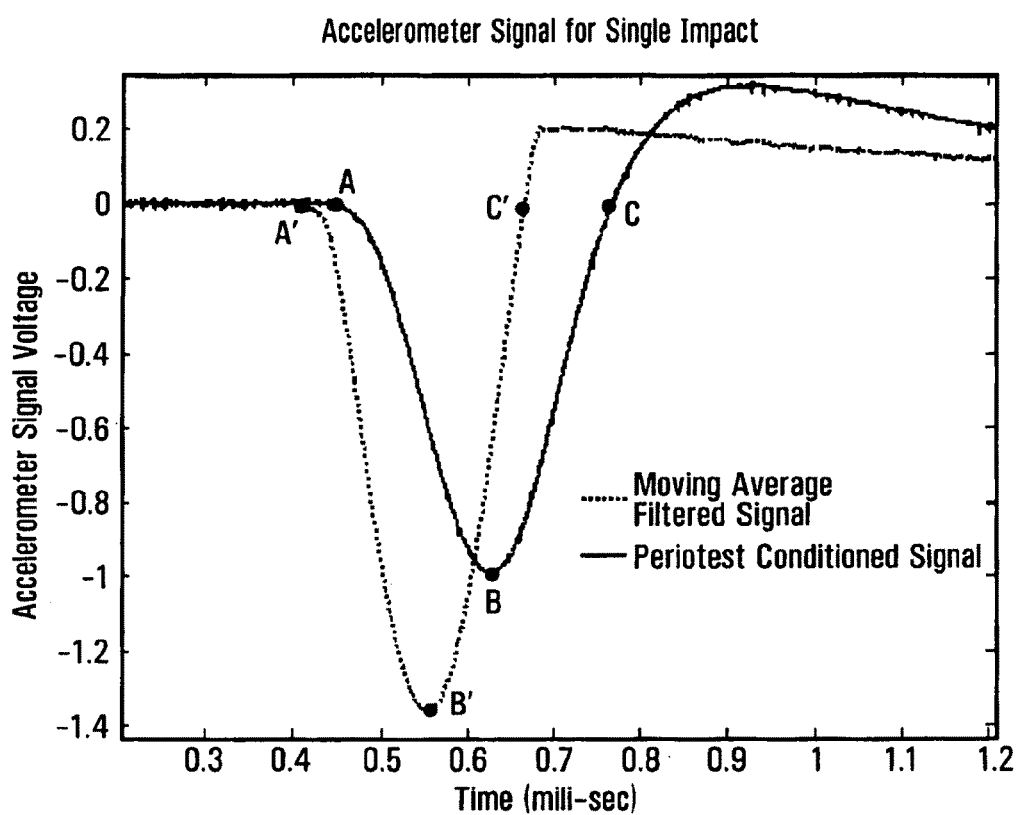
FIG. 10 is a graph showing a Periotest conditioned signal and a moving average filtered signal.

Referring now to FIG. 10, shown is a graph depicting a Periotest conditioned signal and a moving average filtered signal. It can be seen that there is a significant difference between the contact time based on the Periotest filtered signal (A to C) and the contact time based on a signal that has been filtered with a moving average filter (A' to C') which does not introduce any phase shift in the signal. While this difference between the signals may not be important for natural teeth with relatively long contact times, it becomes very significant for the smaller contact times associated with artificial implant measurements.

Due to the filtering distortion of the signal and the limited resolution of the PTV scale it is preferable to measure the resonant frequency based on an accelerometer signal which has not been distorted. For an implant/abutment system with a PTV range between −8 and 0 the resonant frequency will have values ranging from 2700 Hz to 1300 Hz (higher frequency corresponds to a more stable system and lower frequency a less stable system).

Figure 11:
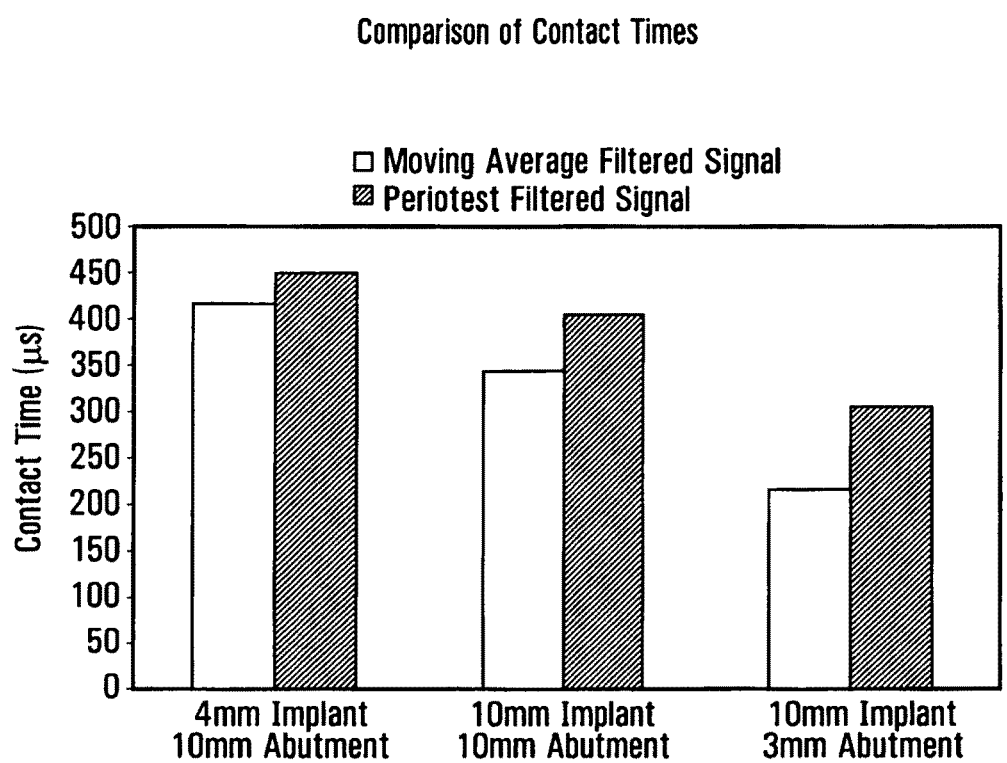
FIG. 11 is a graph depicting a comparison of contact times calculated based on the moving average filtered signal and the conditioned Periotest signal.

Referring now to FIG. 11, shown is a graph depicting a comparison of contact times calculated based on the moving average filtered signal and the conditioned Periotest signal. The differences between the conditioned signal used by the Periotest to calculate the PTV and the alternative signal conditioned using a moving average filter technique, can be significantly different—especially for more rigidly mounted implants. The largest difference in contact time was 88 µs (the 10 mm implant with a 3 mm abutment), which is over 40% of the moving average filtered value. The results show that as the stiffness of the implant/abutment increases the difference between the Periotest conditioned signal and the moving average filter increases. The difference was 8% for a 4 mm implant and a 10 mm abutment, while for the 10 mm implant with a 3 mm abutment this difference increased to 40%.

To independently monitor the motion of the implant/abutment system, a strain gauge was mounted on a separate abutment to measure the bending strain during the impact by the Periotest rod. A linear strain gauge, type EA-06-015EH-120 (Micro-Measurements, Measurements Group Inc., Raleigh, N.C., USA), was mounted vertically on the exterior surface of a 5.5 mm abutment on the side impacted by the rod. The strain gauge was attached using M-Bond 200 (Micro-Measurements) adhesive and then coated with M-Coat D acrylic (Micro-Measurements). The lead wires from the strain gauge were 0.005-inch diameter type 7X00157 (California Fine Wire, California, USA). The strain gauge measurements utilized a DAP 5400a sampling card (Microstar Laboratories, Bellevue, Wash., USA) with a sampling rate of 2 MHz which could simultaneously monitor the strain gauge signal, the moving average filtered accelerometer signal and the Periotest acceleration signal. The strain gauge abutment was then attached to the 4 mm implant and measurements were taken by striking the top of the 5.5 mm abutment.

Figure 12:
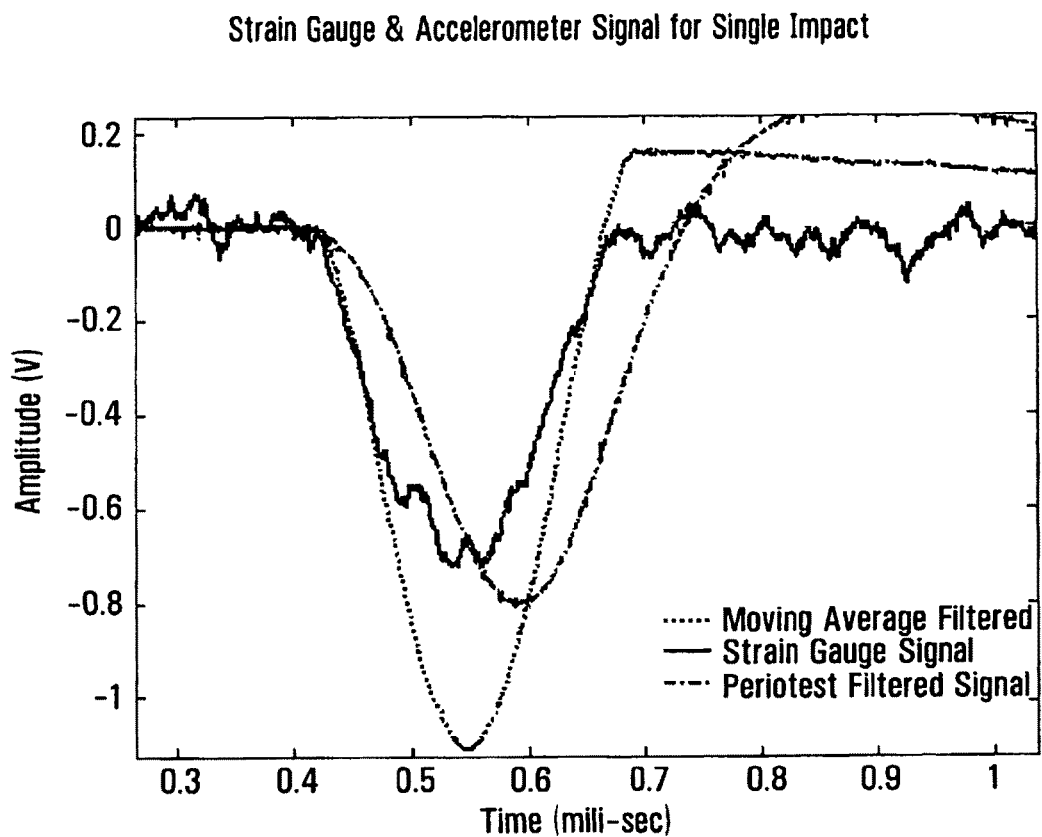
FIG. 12 is a graph depicting a Periotest conditioned signal, a moving average filtered signal and a strain gauge signal.

Referring now to FIG. 12, shown is a graph depecting a Periotest conditioned signal, a moving average filtered signal and a strain gauge signal. This shows one of the 16 strikes taken on the 5.5 mm strain gauged abutment with a 4 mm implant. The contact time based on the strain signal matches the moving average accelerometer signal almost identically, while the Periotest filtered signal shows a significantly longer contact time. The analysis of the accelerometer signal from the handpiece coupled with that from the strain gauge mounted on the abutment showed that the moving average filtered signal is a better measure of the actual motion of the implant/abutment system and provides a more representative measure of the resonant frequency (and thus the stiffness) of the system.

To evaluate the repeatability and reproducibility of the measurement system, seven sets of five consecutive measurements were taken on the 4 mm implant with a 5.5 mm abutment. The handpiece was set at an angle of 5° from an axis perpendicular to the implant. The distance between the end of the handpiece and the abutment was set to 1.5 mm. The micrometer was set so that the Periotest rod would strike the rim of the 5.5 mm abutment. Between each set of five readings the stand was moved and then re-aligned to strike the rim of the abutment in an attempt to replicate the previous set of readings.

Figure 13:
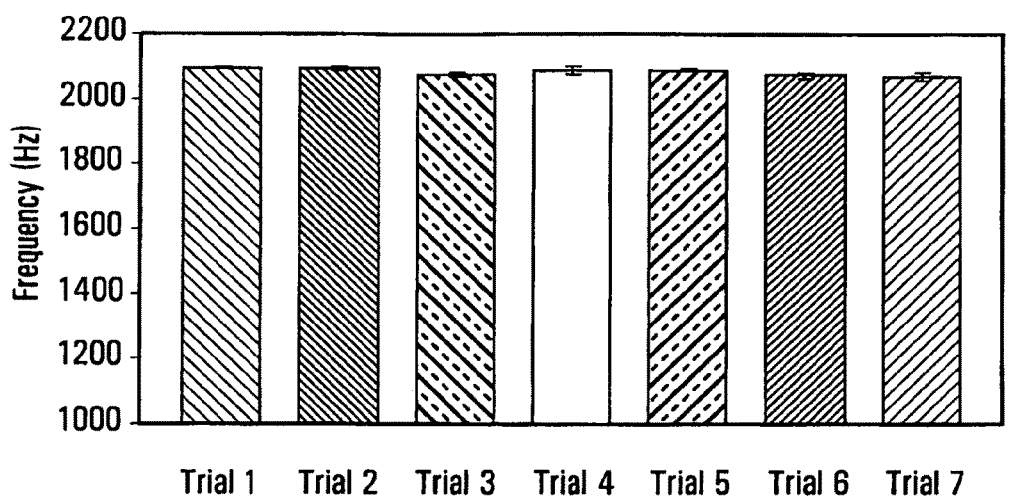
FIG. 13 is a chart depicting the repeatability and reproducibility of the experimentation.

Referring now to FIG. 13, shown is a chart depicting the repeatability and reproducibility of the experimentation. The mean resonant frequency of the 4 mm implant/5.5 mm abutment system for 35 readings (7 sets of 5 readings) was found to be 2083±12 Hz (n=35). Within a single group of five consecutive readings the largest standard deviation was 12 Hz (n=5). Of the seven sets of readings the lowest average value was 2070±12 Hz and the highest average reading was 2095±3 Hz. The error bars on the plot (and subsequent plots for following sections) are one standard deviation of the measurements.

The repeatability and reproducibility measurements show that for 95% confidence (±2 standard deviations) the resonant frequency can be determined to within ±24 Hz when using the moving average filter. With a range of resonant frequencies between 1300 and 2700 Hz for implant/abutment systems this technique provides 58 resolution steps while the PTV scale offers eight (PTV readings between −8 and 0).

Conclusion

While the Periotest system as a whole has some shortcomings when used to monitor implant integrity, the concept of an impact test remains a viable one. The Periotest handpiece itself provides a very convenient method to dynamically excite the implant/abutment system. In fact, the Periotest handpiece has been incorporated as part of a system to measure the damping capacity of materials. The Periotest handpiece was used to develop an improved impact test to monitor implant integrity. Alternate signal processing which avoids the phase shift in the accelerometer signal reducing or eliminating distortions in the contact time was analyzed. Additionally, the effect of critical clinical parameters on the results of the proposed technique was examined such that appropriate clinical protocols could be developed.

Section II: Mathematical Model

Introduction

The drive for a clinically effective, non-invasive technique for monitoring implant stability has led to a number of testing methods based on the concept of resonant frequency. Resonant frequency measurements are an indirect measure of the bone-implant interface integrity and do not provide any specific measures of the physical properties of the interface itself. While initial testing by some researchers suggested that Periotest was an objective and easily applied measurement technique for stability assessment of implants, recent literature reviews of the Periotest discuss some of the failings of the instrument including the effect clinical variables have on the measurements as well as the reduced resolution and low sensitivity when measuring implant-abutment systems. Some of the inconsistencies in the reported Periotest results may be due to a lack of understanding of how the system being measured responds when excited.

For instance, there has been some debate as to what the higher frequency component found in the raw accelerometer signal (see FIG. 4) represents. Some suggest that the higher frequency is a result of partial separation between the impact tool and the implant, resulting in a "bouncing" affect. It has also been hypothesised that this frequency is merely electrical noise on the accelerometer signal or the second mode of vibration of the implant-tissue system. Simulations and modelling are performed to understand the source of this component of the signal and if it can be used to better understand the status of the interface. The higher frequency component can potentially be used to glean more information about the integrity of the implant interface.

In order to gain a greater understanding of the Periotest measurement system, mechanical models of the system have been developed. One approach was to model a Periotest impact. The system shown in FIG. 1 was modeled analytically as a single degree of freedom system in which the implant-abutment was assumed to be a rigid body pinned at the implant base. The model was used to estimate the force of the impact and relate the PTV to an overall equivalent interface stiffness. However, analytical results were purely theoretical and were not verified by directly comparing the theoretical results to in vitro or in vivo experiments.

A subsequent approach involved a two degree of freedom analytical model in which the bone-implant properties were modeled as a series of springs acting along the length of the implant. Model results were then correlated to in vitro measurements for extraoral implant-abutment systems. The in vitro testing and model results determined that implant diameter, length of engagement between bone and implant, angulation of Periotest handpiece and striking height along the abutment all influenced the output of the Periotest. An in vivo patient study was also attempted, however, results were inconclusive due to what the authors believed was a poor understanding of the effects due to measurement parameters and lack of a rigorous clinical testing protocol. Unfortunately, this study utilized the filtered accelerometer signal from the Periotest which, as previously discussed, is not an accurate reflection of the impact response.

More recently, FEA was used for the system shown in FIG. 1 to produce a complete transient simulation of the impact by the rod. This study utilized the un-filtered (raw) accelerometer response and compared finite element solutions with in vitro data for oral and extraoral implants. It was shown that the stiffness of the components as well as the junctions between them significantly affect the overall response and that the implant and abutment do not act as a single rigid body during the contact. One difficulty in using this technique was the very long processing time involved and the necessity of doing a somewhat imprecise frequency analysis on the transient response.

It is desired to develop a better understanding of the dynamics that occur during the impact and how this affects the accelerometer response during measurements. To achieve this, an analytical model of the implant/abutment/Periotest system is developed to aid in interpreting the acceleration signal and in particular how the supporting bone properties affect this signal over a range of implant applications. Analytical model results are compared directly to in vitro measurements. Studies done with the Periotest often erroneously refer to the device as measuring the damping characteristics of the interface. The analytical model can be used to help clear some of the confusion about what bone properties are currently being measured. Additionally, the developed analytical model can be used to simulate changes in the bone stiffness supporting the implant and to determine the effect of bone loss around the neck of the implant. Finally, since some implants currently used incorporate a flange, the model can be used to understand the influence the flange has on the impact accelerometer response.

System and Method

Figure 14:
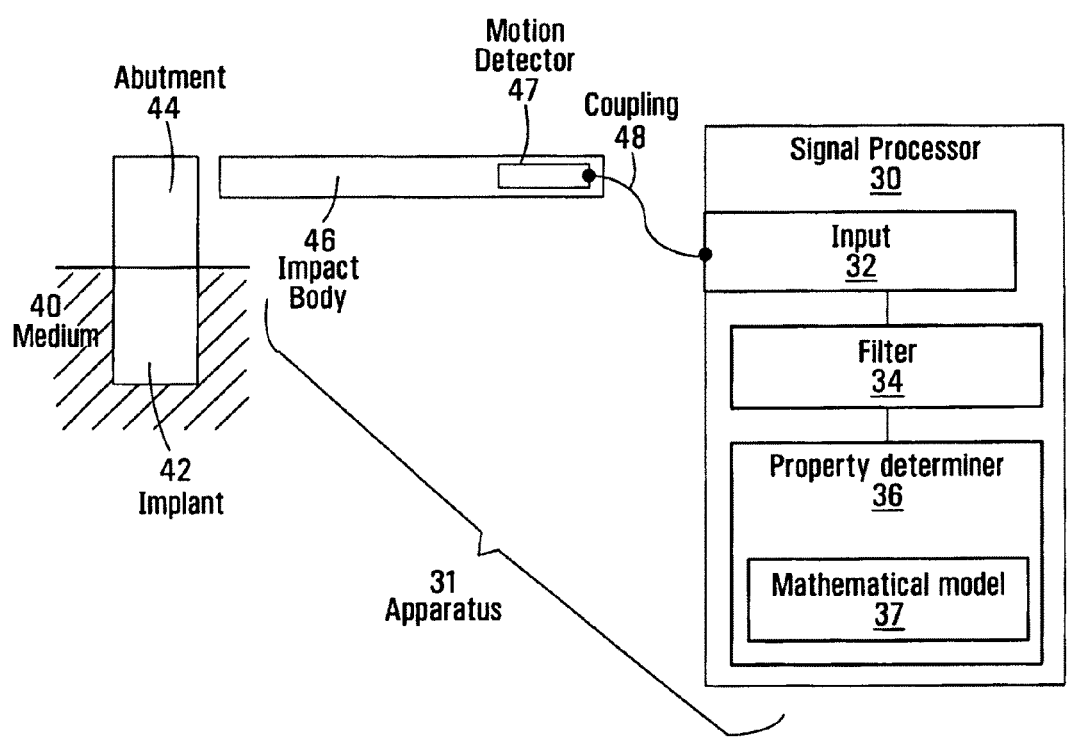
FIG. 14 is a schematic of an apparatus for determining a property of an interface between a medium and an implant that is at least partially embedded therein.

Turning now to FIG. 14, shown is a schematic of an apparatus 31 for determining a property of an interface between a medium 40 and an implant 42 that is at least partially embedded therein. The property of the interface might for example be a measure of the integrity of the interface. The measure of the integrity of the interface might for example be a stiffness of the interface. An abutment 44 is connected to the implant 42. The apparatus 31 has a signal processor 30 connected to an impact body 46 via a coupling 48. The impact body 46 has a motion detector 47, which might for example be an accelerometer. The signal processor 30 has an input 32, a filter 34, and a property determiner 36. The property determiner 36 has a mathematical model 37 for impacting the impact body 46 against the abutment 44. The apparatus 31 may have other components, but they are not shown for sake of simplicity.

In operation, a user impacts the impact body 46 against the abutment 44. The impact body 46 might be accelerated towards the abutment 44 for example via an electromagnet. The motion detector 47 translates the motion of the impact body 46 during impact into a first signal, which is provided to the signal processor 30 over the coupling 48. The coupling 48 is a wired connection, but in alternative implementations might be a wireless connection. The signal processor 30 receives the first signal over the input 32. The first signal is filtered by the filter 34 thereby generating a filtered signal to be used for determining the property of the interface. The property determiner 36 determines a system property based on the signal. The system property might for example be a natural frequency of the system. According to an embodiment of the application, the property determiner 36 analytically determines the property of the interface by applying the system property to the mathematical model 37. Therefore, the property determiner 36 solves for the property of the interface based on the mathematical model 37 and the system property that has been determined.

It is to be understood that the "abutment connected to the implant" does not necessarily mean that the abutment and the implant are formed of separate members. In some implementations, the abutment and the implant are formed of a same continuous member. In this manner, although the abutment and the implant are referred to separately, they are still part of the same continuous member. In other implementations, the abutment and the implant are formed of separate members.

In the illustrated example, the first signal is filtered by the signal processor 30. In other implementations, the first signal is filtered before reaching the signal processor 30. In some implementations, a zero-phase shift filter is implemented. Example zero-phase shift filters that can be used have been described above. In other implementations, the first signal is not filtered at all.

There are many possibilities for the mathematical model 37. The mathematical model 37 can have varying complexity depending on how many components and/or considerations the model is to include. In some implementations, the mathematical model 37 has three-degrees of movement. In other implementations, the mathematical model 37 has four-degrees of movement. Other implementations are possible. Example mathematical models are provided below.

In the illustrated example, the property determiner 36 is implemented by a signal processor. More generally, the property determiner 36 can be implemented by hardware, firmware, software, or any appropriate combination thereof. For software implementations, there is provided a computer readable medium having computer executable instructions stored thereon for execution on a processor for implementing functionality described herein.

Figure 15:
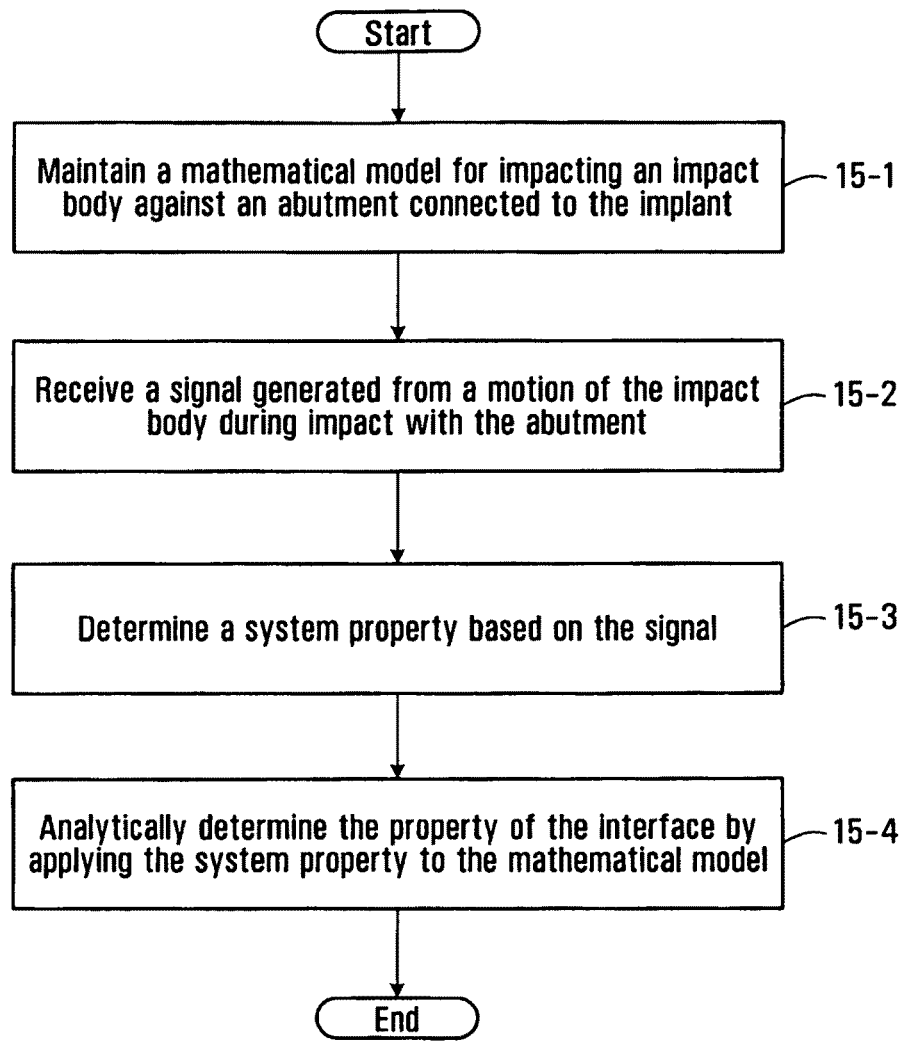
FIG. 15 is a flowchart of a method of determining a property of an interface between a medium and an implant that is at least partially embedded therein.

Referring now to FIG. 15, shown is a flowchart of a method of determining a property of an interface between a medium and an implant that is at least partially embedded therein. The property of the interface might for example be a measure of the integrity of the interface. The measure of the integrity of the interface might for example be a stiffness of the interface. This method can be implemented by a signal processor, for example by the property determiner 36 of the signal processor 30 shown in FIG. 14. More generally, this method may be implemented in any appropriate apparatus.

At step 15-1, the apparatus maintains a mathematical model for impacting an impact body against an abutment connected to the implant. Example mathematical models are provided below. At step 15-2, the apparatus receiving a signal generated from a motion of the impact body during impact with the abutment. At step 15-3, the apparatus determines a system property based on the signal. The system property might for example be a natural frequency of the system. According to an embodiment of the invention, at step 15-4 the apparatus analytically determines the property of the interface by applying the system property to the mathematical model. Therefore, the apparatus solves for the property of the interface based on the mathematical model and the system property that has been determined.

In Vitro Experimental Model

Figure 16:
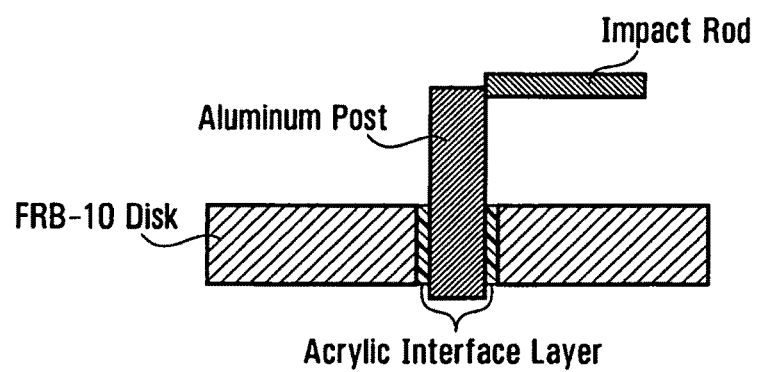
FIG. 16 is a schematic of the in vitro experimental model for impact testing.

Referring now to FIG. 16, shown is a schematic drawing of the in vitro experimental model for impact testing. The in vitro experimental model was developed to assist in the development of a measurement protocol and for validation of analytical and numerical models. The model is approximately the size of an oral implant-abutment system. It includes an aluminum post fixed with acrylic into the centre of a disk of FRB-10 (Measurements Group Inc, Raleigh, N.C., USA).

Finite Element Analysis (FEA) Model

Finite element analysis (FEA) models have been used by various researchers to attempt to find relationships between natural frequencies and the surrounding conditions of the implant. One approach involved modal analysis of the implant-tissue system to investigate how bone type and bone density affects resonant frequency. In the current work, FEA is used to produce a more thorough dynamic model of the implant-abutment by including the impact of the Periotest rod with the implant.

Figure 17:
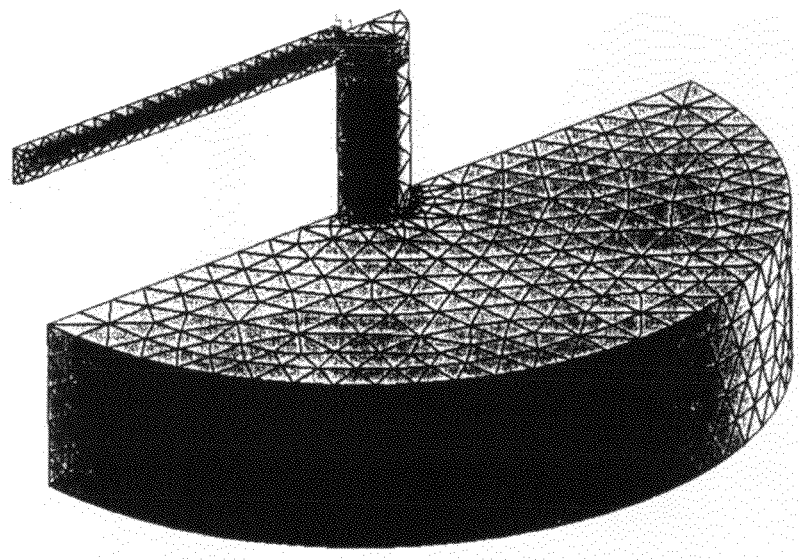
FIG. 17 is a schematic of a finite element analysis (FEA) model for the impact test.

Referring now to FIG. 17, shown is a schematic of an FEA model for an impact test. The finite element model created to simulate this in vitro model used ANSYS 7.1 (ANSYS Inc, Canonsburg, Pa., USA) on a personal computer. Containing approximately 15000 elements, the model includes the in vitro geometry and the Periotest rod. Only one half of the structure is considered due to symmetry resulting in decreased processing time used to arrive at a solution. The model was meshed with tetrahedral elements with mid-sided nodes. These quadratic elements are comprised of 10 nodes having three degrees of freedom at each node: translation in the nodal x, y, and z directions. Element properties and geometric values were matched to those of the in vitro model, as listed in Table 1 and Table 2. Convergence testing was performed to ensure the mesh was adequately dense such that solutions did not change more that 1% when the element size was halved.

To model the impact between the rod and the aluminum post, contact elements were created between the two adjacent surfaces so that the rod and the rest of the system can move independently of each other without allowing the rod to penetrate the post. This was done using a combination of 3-D eight node, surface to surface contact elements which are used to represent contact and sliding between three dimensional deformable surfaces and 3-D target elements which overlay the solid elements describing the boundary of the deformable body. Since the impact is direct, sliding is assumed to be negligible thus friction coefficients were ignored to save processing time. The Periotest rod was constrained to move horizontally and was assumed to have an initial velocity of 0.2 m/s towards the aluminum post to match the manufacturer's specifications of the Periotest's performance. A transient analysis was used to determine the motion of the system with a typical sampling rate of once every 0.6 microseconds. In cases where greater resolution was desired, this was increased such that the highest resolved frequency was 20 times faster than the highest desired frequency as recommended by ANSYS.

As mentioned previously, one of the goals of the model was to simulate changes in the natural frequencies of the implant-tissue-Periotest system due to changes in the status of the interface. Specifically, these include loss of osseointegration, loss of bone margin height and development of connective soft tissue in the bone-implant interface. This was accomplished through slight modifications to the interface region of the model. To ensure a smooth transition of the elements from the relatively small interface elements to the disk, the ANSYS element expansion function was utilized to keep aspect ratios small while expanding each consecutive element by 130% until the specified disk element size was reached.

For a fully osseointegrated implant, the implant and interface layer shared nodes along their common boundaries and thus allowed no separation between the two. When a loss of osseointegration was simulated, the implant and interface layer no longer shared nodes along the common boundaries. Instead a layer of contact elements were meshed between the two to allow separation in the area of osseointegration loss but not penetration. The nodes below this loss still coincided however. For the simulation of reduced bone margin height, the height of the interface layer was reduced to simulate receding bone around the neck of the implant. From a mechanical viewpoint, the difference is that while in both of these cases there is no possibility of generating tensile forces between the implant and the surrounding tissue in the area of loss, compressive forces can be generated in the non-osseointegrated case. The development of connective soft tissue in the interface layer was simply modelled as a reduction in the stiffness of the entire interface layer.

To verify the FEA model, the implant-abutment system while being impacted with the rod at the free end was modelled as a Bernoulli-Euler beam fixed at one end with a point mass at the other. The solution for this problem results in the transcendental equation for the frequency parameter ($\beta L$). For the beam parameters given in Table 1 and Table 2, the first two values of ($\beta L$) are 0.5776 and 3.9311. The natural frequency of vibration of this system can be determined using the following:

$$p = (\beta L)^2 \sqrt{\left(\frac{EI}{m_b L^3}\right)} \quad (1)$$

where p is natural frequency, E is Young's modulus of the cantilever, I is the second moment of area about the neutral axis, L is the length of the cantilever and $m_b$ is the mass of the cantilever.

Simulations were for the typical implant-abutment systems mentioned previously (extraoral prostheses: 4 mm implants with 5 mm abutments and oral implants: 9 mm implants with 10 mm abutments). In all instances it was assumed that the rod impacts the top of the abutment. For simulation of the loss of osseointegration and bone loss, it was assumed that this begins at the outer surface of the hard tissue and propagates toward the base of the implant. In the extraoral case, the dimensions of the model were altered to those found in Table 1.

Figure 18:
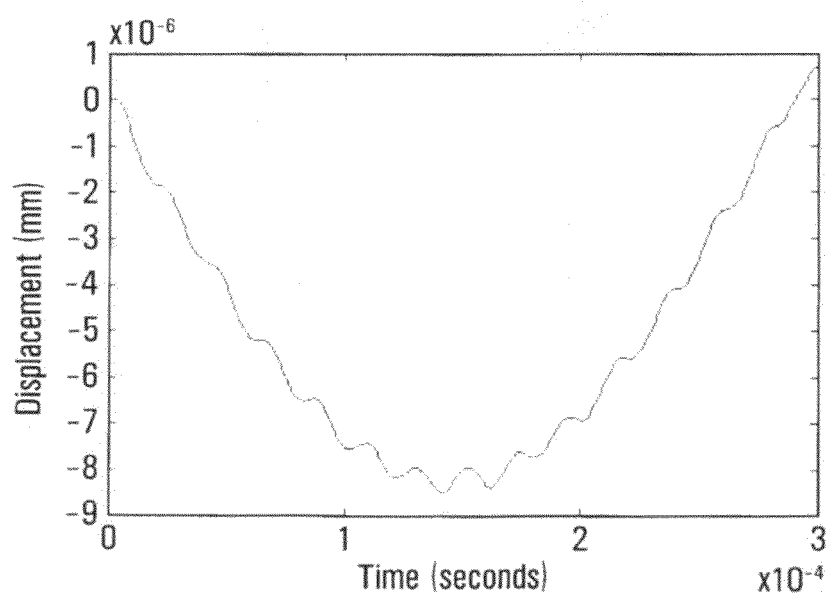
FIG. 18 is a graph depicting a typical transient analysis signal for the FEA model of FIG. 17.

Referring now to FIG. 18, shown is a graph depicting a typical transient analysis signal for the FEA model of FIG. 17. Note that the transient analysis signal is produced assuming a system with an infinitely stiff disk and interface layer resulting in a rigidly fixed, 10 mm long cantilevered aluminum post. Even though transient analysis signal is a displacement/time result, it is very similar to that of the raw experimental result shown in FIG. 4. For instance, the transient analysis signal shows two natural frequencies. If the signals are assumed to be a combination of harmonic functions, the acceleration signal is equivalent to a scaled displacement signal. Therefore the transient signal can be related to the experimental signal. As with the experimental result, the simulated signal appears to have a fundamental frequency with a higher frequency superimposed. When the contact status between the Periotest rod and the implant was reviewed, it was found that they remained in contact throughout the strike. The transient signals were analyzed using the custom software to determine the two natural frequencies, which appeared to combine to produce the characteristic signal.

These FEA results were compared to the frequencies predicted by Equation (1). The results for the FEA model and analytical solution for the first natural frequency were 2728 Hz and 2711 Hz respectively and 127 kHz and 126 kHz for the second natural frequency. Therefore the FEA model was within 0.8% relative error of the analytical solution for both cases. As this is below the convergence criterion of 1%, the model yielded accurate results.

The finite element simulation was also compared to the in vitro model. The FEA simulation parameters were set to those found in Table 1 and Table 2, and the results were compared to the results of in vitro testing. With the rod impacting the top of the post, the FEA produced results of 1726 Hz and 46 kHz for the first two natural frequencies respectively, while the in vitro tests produced 1790 Hz and 40 kHz (averaged from the three tests each on the six identical post/disk systems). This equates to 3.5% relative error for the first natural frequency and 13% for the second. Again the status of the contact elements remained closed throughout the entire strike.

Since no separation was found to occur during the strike in the finite element analysis and the model predicted the second natural frequency for both the analytical and in vitro cases, there is strong evidence that the higher frequency in the experimental signal is indeed the second mode of vibration of the implant-abutment system.

Figure 19A:
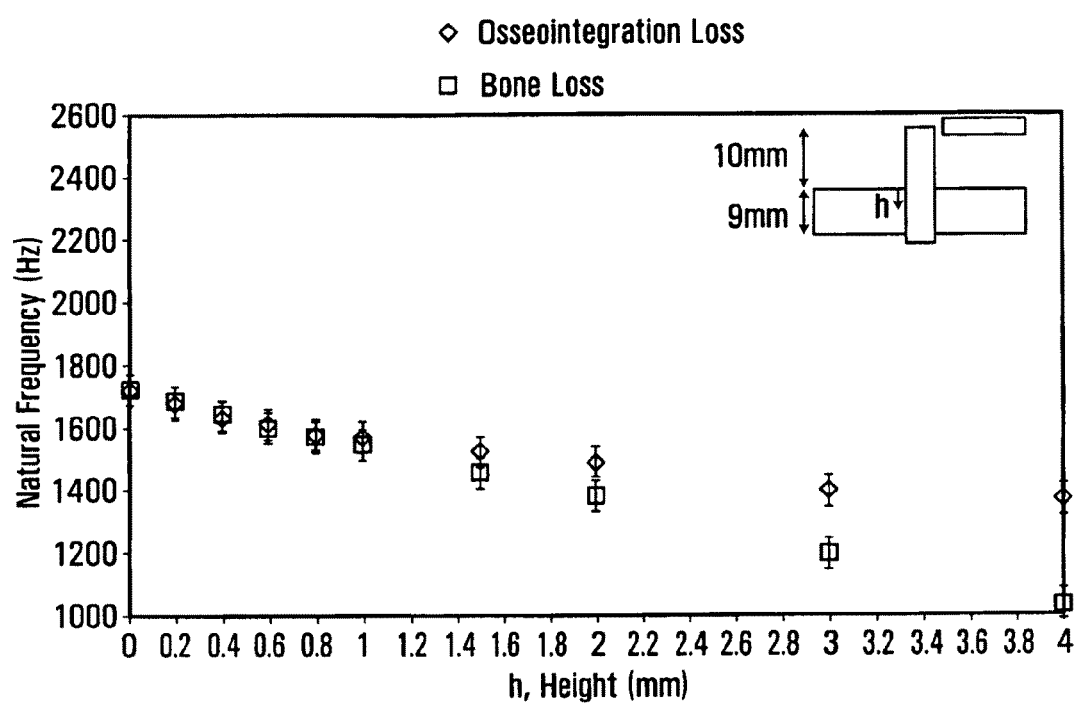
FIGS. 19A through 19D are graphs depicting changes in first and second natural frequencies of the implant abutment as a function of increasing loss of osseointegration and bone margin height.
Figure 19B:
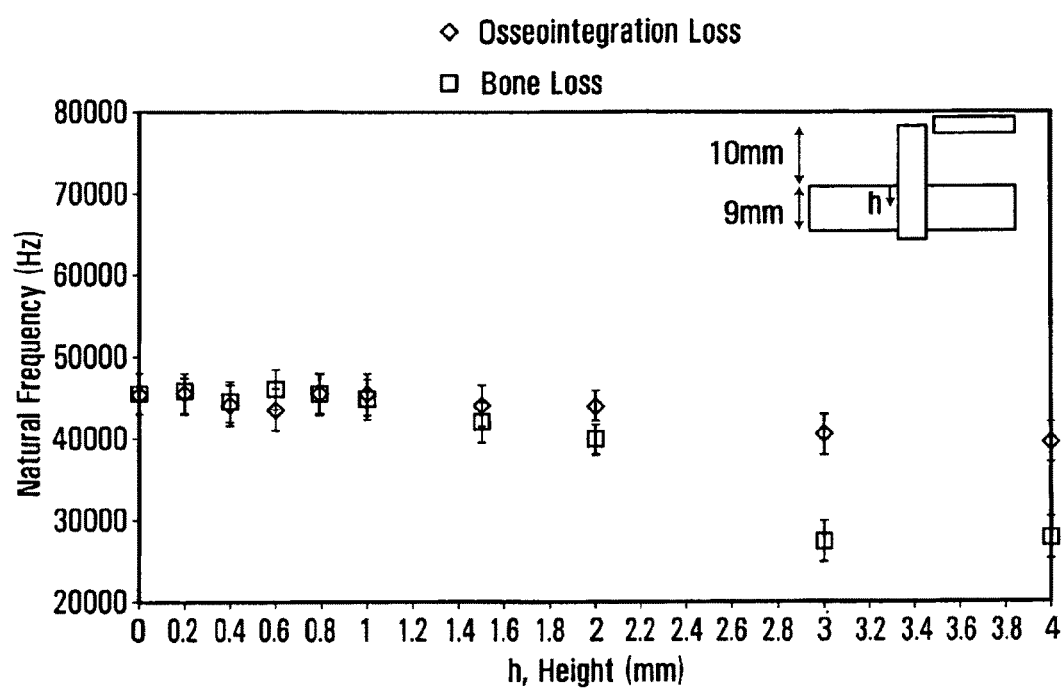
Figure 19C:
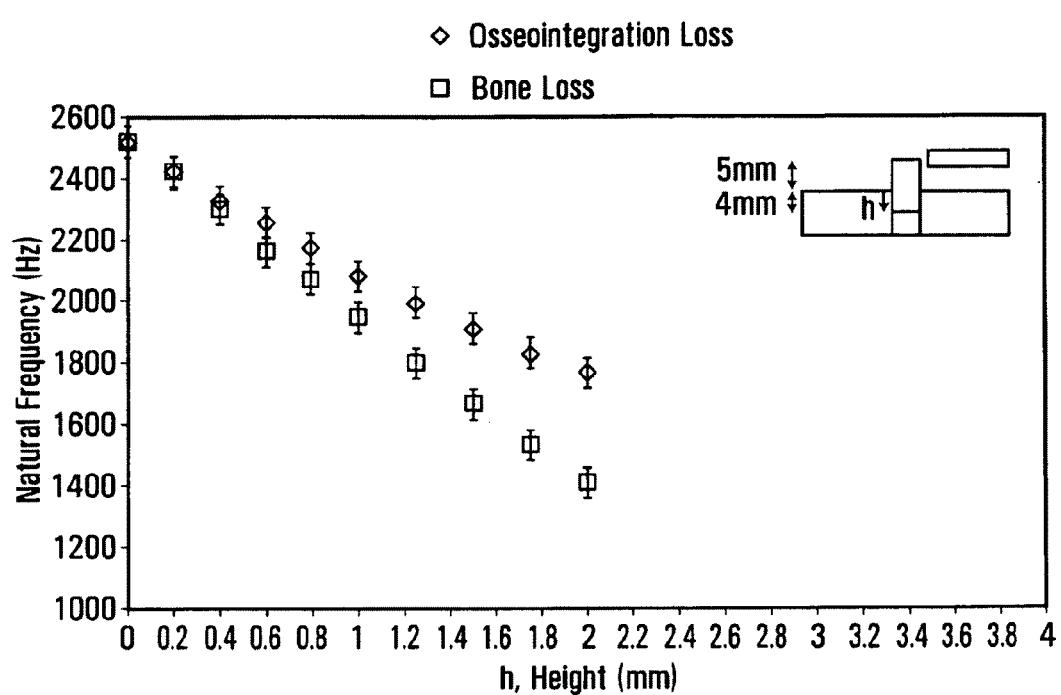
Figure 19D:
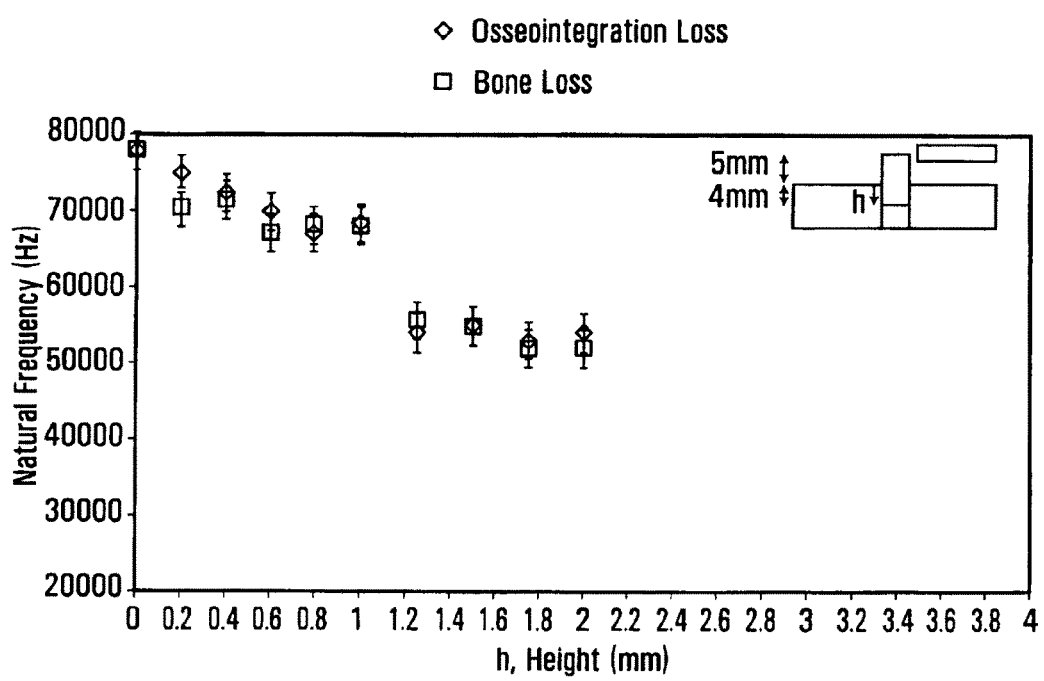

Referring now to FIGS. 19A through 19D, shown are graphs depicting changes in first and second natural frequencies of the implant abutment as a function of increasing loss of osseointegration and bone margin height. These results were obtained from the FEA model shown in FIG. 17. FIGS. 19A and 19B show graphs depicting changes in first and second natural frequencies of the implant abutment as a function of increasing loss of osseointegration and bone margin height for a 10 mm abutment (oral implant). FIGS. 19C and 19D show graphs depicting changes in first and second natural frequencies of the implant abutment as a function of increasing loss of osseointegration and bone margin height for a 5 mm abutment (extra-oral implant).

It has been assumed that the region of loss begins at the outer surface (skin side) of the hard tissue and propagates towards the base of the implant. The error bars for the first natural frequency plots represent the difference between to adjacent data points when calculating the contact time. For instance, there may not be a data point exactly on the zero displacement axis, thus it lies somewhere between the point before and after the axis crossing. The error bars for the second natural frequency plots represent the FFT resolution.

For the first (lowest) natural frequency (FIGS. 19A and 19C), both sizes of implant-abutments evaluated show measurable changes for relatively small regions of loss. As it has been reported that changes equivalent to 100 Hz are statistically significant, a loss of approximately 0.2 mm would be detectable for the shorter implants and 0.4 mm for the longer system. The difference in loss (osseointegration vs. bone loss) is not distinguishable until the height of loss has extended to approximately 0.8 mm for the shorter implant and to approximately 1.9 mm for the longer (depicted as "h" in FIGS. 19A-19D). While the second (higher) natural frequency (FIGS. 19B and 19D) show a similar trend as the length of the loss zone increases, the differences between loss of osseointegration and bone loss are not as evident.

Figure 20A:
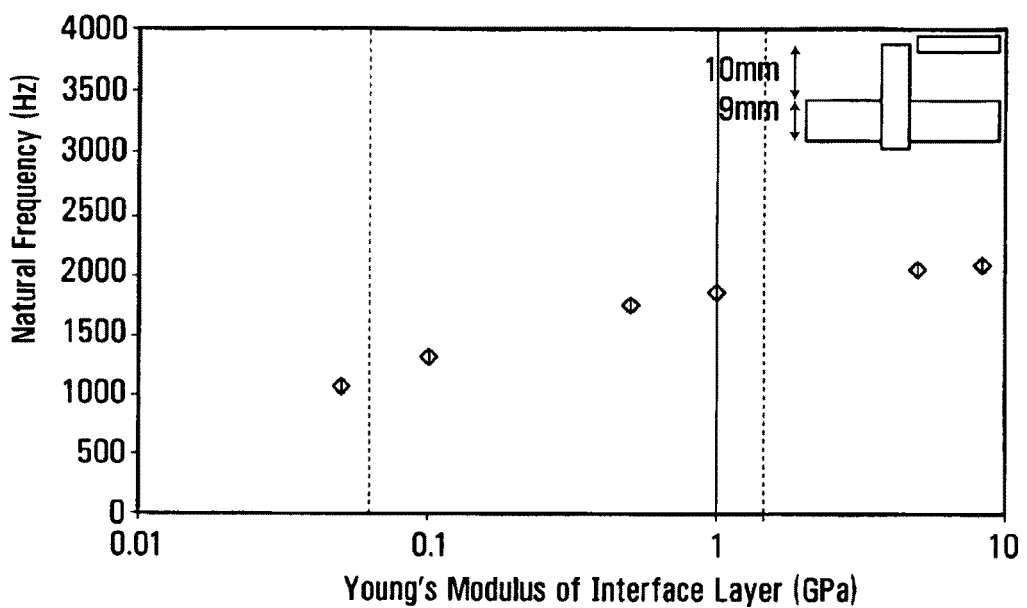
FIGS. 20A through 20D are graphs depicting changes in first and second natural frequencies of the implant abutment as a function of increasing interface layer stiffness.
Figure 20B:
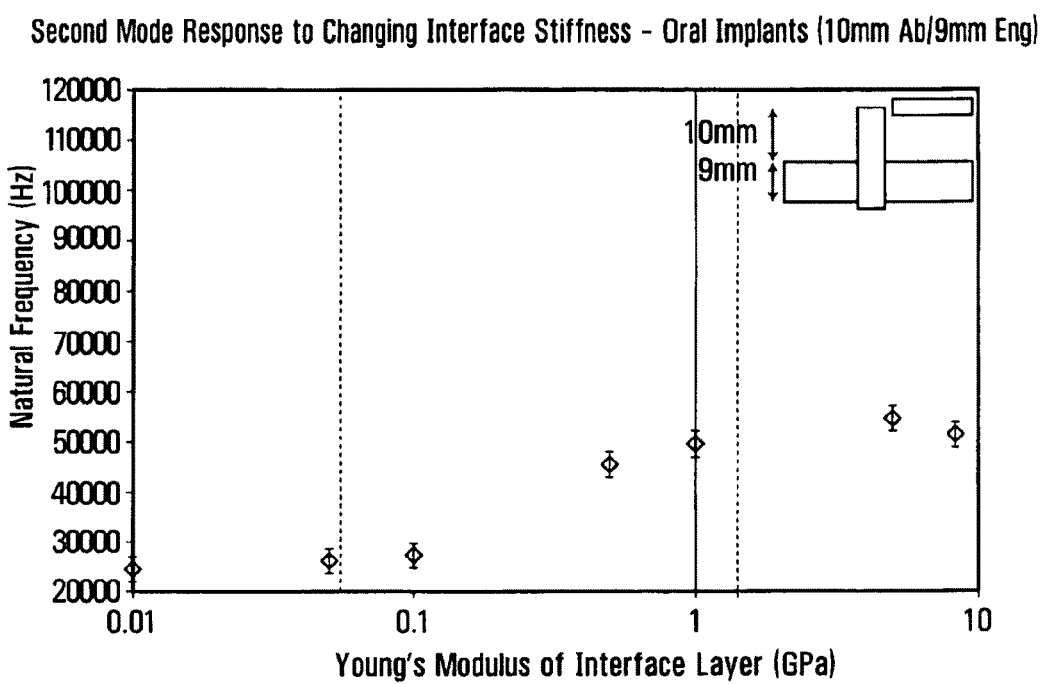
Figure 20C:
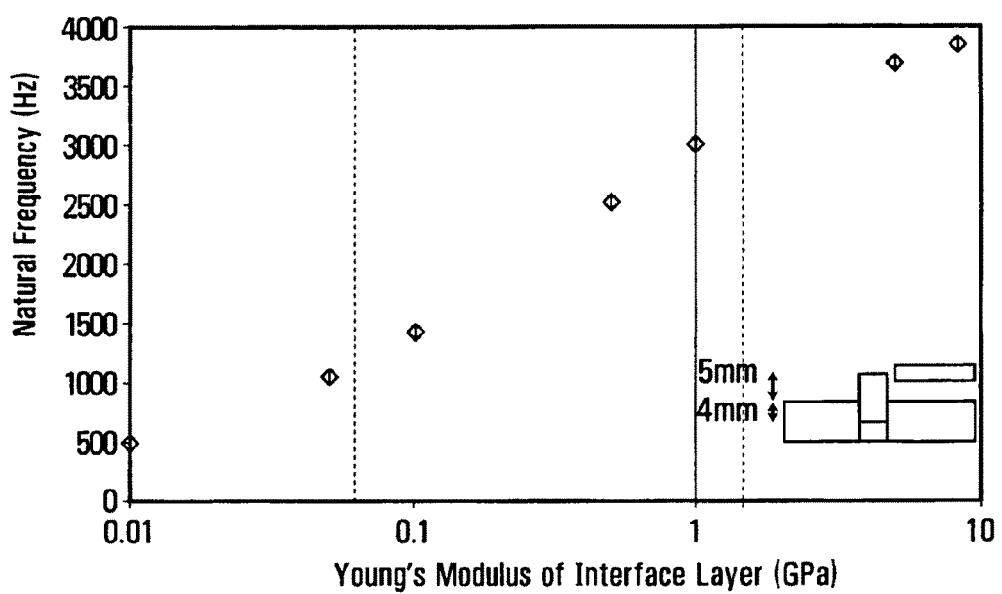
Figure 20D:
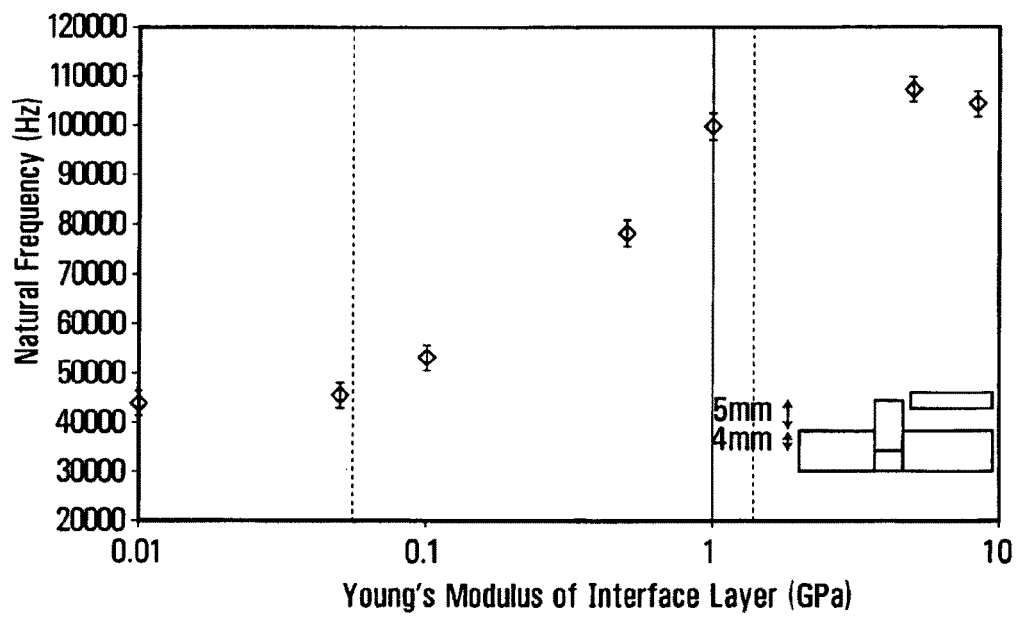

Referring now to FIGS. 20A through 20D, shown are graphs depicting changes in first and second natural frequencies of the implant abutment as a function of increasing interface layer stiffness. These results were obtained from the FEA model shown in FIG. 17. FIGS. 20A and 20B show graphs depicting changes in first and second natural frequencies of the implant abutment as a function of increasing interface layer stiffness, for a 10 mm abutment (oral implant). FIGS. 20C and 20D show graphs depicting changes in first and second natural frequencies of the implant abutment as a function of increasing interface layer stiffness, for a 5 mm abutment (extra-oral implant).

The simulations for the development of a softer interface layer, which could correspond to the development of connective soft tissue or reduced stiffness during healing, are given in FIGS. 20A-20D for the two sizes of implants with similar error bars to the previous plots. FIGS. 20A and 20C show the dramatic change in the lowest natural frequency as the stiffness (modulus of elasticity) of the interface layer changes. The region between the dashed lines is an estimated range of modulus of elasticity for soft connective tissue (scar tissue) to hard tissue (quality bone) and it is evident that the lowest natural frequency can change in the order of 50% and will therefore be easily detectable. The higher natural frequency also shows a similar dramatic change as the modulus changes. It should be remembered that for these simulations, the change in stiffness occurs over the entire interface simultaneously.

If the change in stiffness were only over a portion of the engagement length, then the change in the natural frequency would not be as large as shown. The situation depicted does simulate the change in overall stiffness, which is expected to occur during the healing after implant placement. After initial placement, the supporting hard tissue is believed to first "soften" as it begins to remodel. This is followed by a period in which the stiffness increases as osseointegration occurs. This would mean that the natural frequencies would fall slightly from their initial values then increase as osseointegration occurs. If it does not and the frequency does not increase this would be a signal that soft connective tissue is developing instead of the osseointegrated bond desired.

The interface model used for the simulations above was verified by comparison to the in vitro experiment as well as an analytical solution. The first and second natural frequencies predicted numerically were within 1% of the analytical result. The comparison to the in vitro results produced not only a close comparison in its frequency content, but indicated that the impacting rod remained in contact with the abutment and did not "bounce" as had been previously speculated. Instead, the higher frequency, which had been seen previously in similar tests, related to a predictable second mode of vibration of the implant-abutment system that was also excited by the impact.

The results of the simulation above indicate that clinical changes in the integrity of the interface should be detectable from the frequency response changes. The simulations indicate that with either a loss of osseointegration or bone margin height for the shorter implant of as little as 0.2 mm, the change in frequency response is sufficient to be clinically detectable. In addition, changes in the stiffness of the interface, such as might occur after initial implant placement or through the development of connective soft tissue, result in easily measurable frequency changes. All of the simulations indicate that the use of an impact test can produce clinically meaningful results using the lowest natural frequency excited by the impact.

Four-Degree of Freedom Model

A four-degree of freedom analytical model has been developed to interpret measurement results of an impact testing method based on the Periotest handpiece. Model results are compared to a variety of in vitro tests to verify model predictions and to gain an understanding of the parameters influencing the measurements. Model simulations are then used to predict how changes in the supporting stiffness properties, material loss around the neck of the implant and the presence of an implant flange will affect the measurements.

Analytical Model Development

Figure 21:
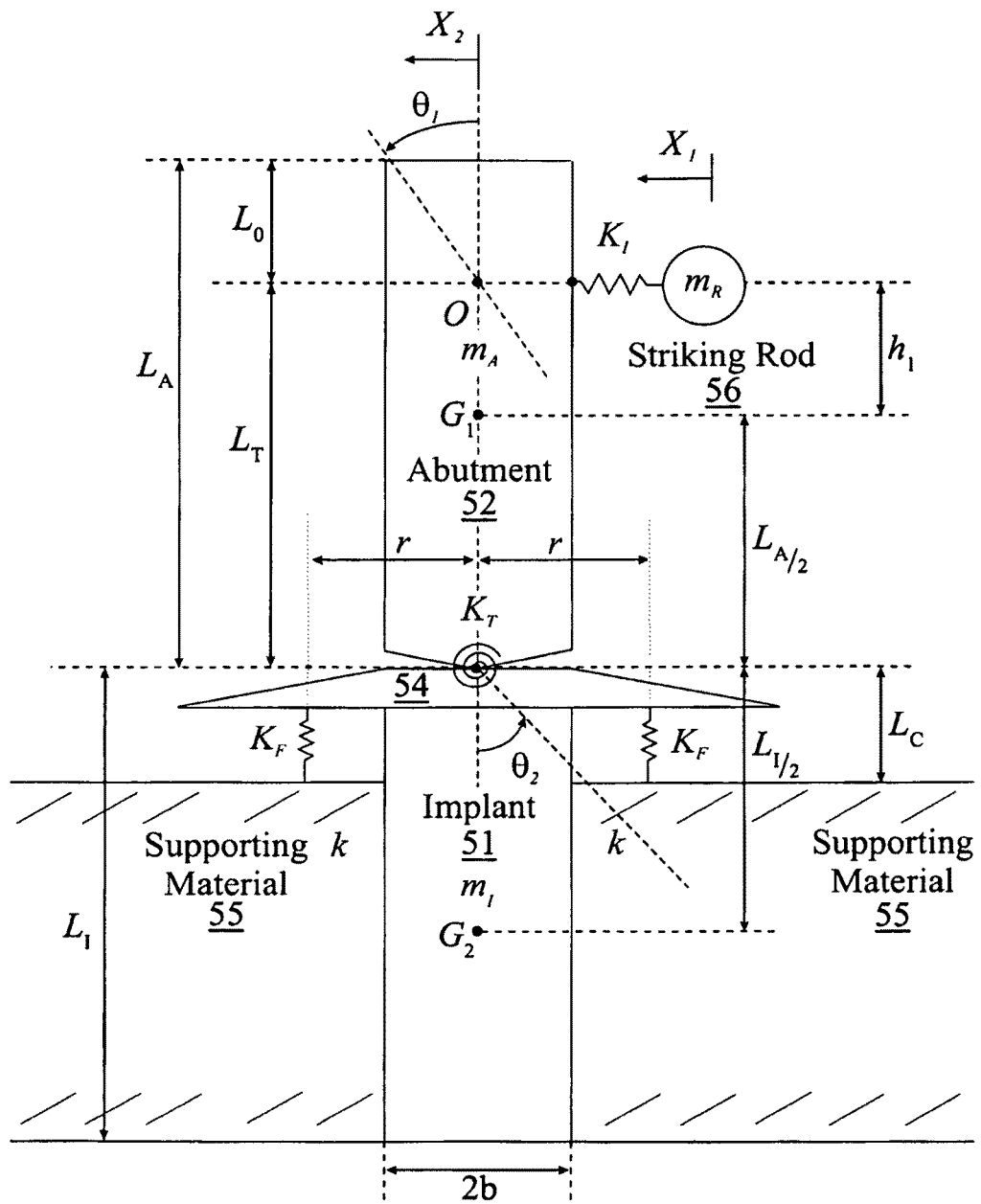
FIG. 21 is a schematic of a four-degree of freedom model for the impact system.

Referring now to FIG. 21, shown is a schematic of a four-degree of freedom model for the impact system. The model has an implant 51, partially embedded in a supporting material 55. An abutment 52 is affixed to the implant 51. A striking rod 56 is also present. The symbols used are shown in Table 3.

TABLE 3

Symbol Definitions

| Variable | Definition |
|---|---|
| $X_1$ | Coordinate describing horizontal position of impacting rod. |
| $X_2$ | Coordinate describing horizontal position of specific point on abutment. |
| $\theta_1$ | Coordinate describing angular rotation of the abutment. |
| $\theta_2$ | Coordinate describing angular rotation of the implant. |
| $K_I$ | Impact stiffness ($K_{SYS}$ and $K_{DEF}$ in series. |
| $K_T$ | Torsional stiffness at the implant-abutment joint. |
| k | Stiffness of bone-implant interface (per unit length). |
| O | Position along abutment longitudinal axis that crosses the line of impact. |
| $G_1$ | Location of abutment center of gravity. |
| $G_2$ | Location of implant centare of gravity. |
| $L_A$ | Length of the abutment. |
| $L_I$ | Length of the implant. |
| $L_O$ | Vertical distance from the top of the abutment to point O. |
| $h_1$ | Veritcal distance from O to $G_1$. |
| $L_C$ | Distance joint is above the supporting material surface. |
| h | Radius of implant-abutment system. |

In this model, both the implant 51 and the abutment 52 are treated as separate rigid bodies, while the impact rod 56 is treated as a point mass with mass $m_R$. The implant and abutment are assumed to be connected by a pin and torsional spring of stiffness $K_T$.

During the time that the abutment and impact rod are in contact, the dynamic response of the system is described using the coordinates $X_1$ (displacement of the impacting rod), $X_2$ (displacement of a point, ○, along the central axis of the abutment at the same height as the striking rod), $\theta_1$ (rotation of the abutment) and $\theta_2$ (rotation of the implant) as shown in FIG. 21. The stiffness, k, of the supporting material 55 is represented by a series of distributed horizontal and vertical springs along the length of the supporting material 55. This stiffness is assumed to be uniform and constant in both the vertical and horizontal directions. The supporting stiffness, k, is an equivalent stiffness. Although the impact rod and abutment are modeled as rigid bodies, there is in fact some deformation, which occurs during the impact. A spring of stiffness $K_I$ is introduced between the rod and the abutment to account for these deflections. Similarly, the torsional spring ($K_T$) is used to approximate bending or flexibility about the implant-abutment joint. Although the abutment is modeled as rigid, FEM studies have shown that bending can occur. To account for this, the torsional spring is used to attempt to account for the relative motion (bending) within the abutment. While simulating bending with two rigid bodies (the implant and abutment) and a torsional spring is quite simplistic, it does provide an estimation of the bending while minimizing the added complexity of the mathematical model.

To estimate the damping properties of the supporting bone, proportional damping was used in which the damping matrix is assumed to be proportional (proportionality coefficient $\beta$) to the stiffness matrix so that the equations of motion become $$[M]\{\ddot{x}\} + \beta[K]\{\dot{x}\} + [K]\{x\} = \{0\}.$$

Assuming proportional damping allows for normal mode analysis to be utilized and simplifies the analytical solution.

Some implants have a flange, which is modeled at 54. For the flanged extraoral implants an additional flange stiffness ($K_F$) was added. While the flange 54 may be providing support across its entire surface, $K_F$ is represented as a single equivalent stiffness at an effective distance r from the center of the implant 51 as shown in FIG. 21. The added spring $K_F$ provides forces in either tension or compression representing a flange osseointegrated to the supporting bone structure. Calculations including $K_F$ assume the flange is bonded to the supporting surface and represent a maximum contribution to the implant support. For implants without a flange, $K_F$ was set to zero.

The equations of motion for the four degree of freedom analytical model illustrated in FIG. 21 are detailed below.

$$[M]\begin{Bmatrix} \ddot{X}_1 \\ \ddot{X}_2 \\ \ddot{\Theta}_1 \\ \ddot{\Theta}_2 \end{Bmatrix} + \beta[K]\begin{Bmatrix} \dot{X}_1 \\ \dot{X}_2 \\ \dot{\Theta}_1 \\ \dot{\Theta}_2 \end{Bmatrix} + [K]\begin{Bmatrix} X_1 \\ X_2 \\ \Theta_1 \\ \Theta_2 \end{Bmatrix} = \{0\}$$

where [M] contains constants which describe the mass properties of each of the elements in the system and [K] contains constants which describe the stiffness or flexibility of the various components of the system. Both [M] and [K] are influenced by the geometry (lengths, etc.) of the various components in the system.

$$[M] = \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix}$$

with $[M_{11}] = m_R;$ $[M_{12}] = [M_{21}] = [M_{13}] = [M_{31}] = [M_{14}] = [M_{41}] = 0;$ $[M_{22}] = m_A + m_I;$ $[M_{23}] = [M_{32}] = -\left(m_A h_1 + m_I\left(\frac{L_A}{2} + h_1\right)\right);$ $[M_{24}] = [M_{42}] = -m_I \frac{L_I}{2};$ $[M_{24}] = [M_{42}] = -m_I \frac{L_I}{2};$ $[M_{33}] = J_A + m_A h_1^2 + m_I\left(\frac{L_A}{2} + h_1\right)^2;$ $[M_{34}] = [M_{43}] = m_I\left(\frac{L_A}{2} + h_1\right)\frac{L_I}{2};$ $[M_{44}] = J_I + m_I\left(\frac{L_I}{2}\right)^2:$ and $$[K] = \begin{bmatrix} K_{11} & K_{12} & K_{13} & K_{14} \\ K_{21} & K_{22} & K_{23} & K_{24} \\ K_{31} & K_{32} & K_{33} & K_{34} \\ K_{41} & K_{42} & K_{43} & K_{44} \end{bmatrix}$$

with $[K_{11}] = K_I;$ $[K_{12}] = [K_{21}] = -K_I;$ $[K_{13}] = [K_{31}] = [K_{14}] = [K_{41}] = 0;$ $[K_{22}] = K_I + 2k(L_I - L_C);$ $[K_{23}] = [K_{32}] = -2k(L_I - L_C)\left(\frac{L_A}{2} + h_1\right);$ $[K_{24}] = [K_{42}] = -k(L_I^2 - L_C^2);$ $[K_{33}] = 2k(L_I - L_C)\left(\frac{L_A}{2} + h_1\right)^2 + K_T;$ $[K_{34}] = [K_{43}] = k\left(\frac{L_A}{2} + h_1\right)(L_I^2 - L_C^2) - K_T;$ $[K_{44}] = \frac{2}{3}k(L_I^3 - L_C^3) + 2kb^2(L_I - L_C) + K_T + r^2 K_F.$ The implants and abutments were treated as solid cylinders with mass moments of inertia of $J_I$ and $J_A$ for the implants and abutments, respectively. Implant masses ($m_I$) were measured and found to be 0.1538 and 0.647 gm for the 4 mm and 10 mm implant The abutment masses ($m_A$), were measured as 0.228, 0.333, 0.448, 0.647 gm for the 4, 5.5, 7, 10 mm abutments. The lengths $L_A$ and $L_I$ refer to the length of the abutments and implants, with $L_c$ and $h_1$ referring to the implant height above the bone level (for cases of bone resorption) and the distance between the center of gravity of the abutment and the striking point, respectively. The radius of the implant and abutment is b and the effective radius of the flange support is r. Using the normal mode method, the equations of motion were uncoupled using the concept of the modal matrix. The general solution then takes on the form of the summation of each of the uncoupled solutions such that $$\begin{Bmatrix} X_1(t) \\ X_2(t) \\ \Theta_1(t) \\ \Theta_2(t) \end{Bmatrix} = \sum_{r=1}^{4} e^{-v_r p_r t} \left[ \frac{1}{p_r} \{\mu\}_r^T [M]\{\dot{x}(0)\} \sin\left(\sqrt{1-v_r^2}\, p_r t\right) \right] \{\mu\}_r. \quad (2)$$

where $v_r$ is the damping ratio for each mode, $p_r$ is the resonant frequency for each mode and $\{\mu\}_r$ is a column vector of the normalized modal matrix $[\mu]$ and $\dot{x}(0)$ is the initial velocity of the system before impact.

The damping ratio $v_r$ for each mode can be determined from $\beta$ as $$\beta = \frac{2(v_r)}{p_r}. \quad (3)$$

The value for $\beta$ was found by setting r=2 and choosing the damping ratio $v_2$ to match the in vitro measurements. Once $\beta$ is known, Equation (3) can be used to solve for v for each mode.

The acceleration response can be obtained by taking the second derivative of Equation (2) to give $$\begin{Bmatrix} \ddot{X}_1(t) \\ \ddot{X}_2(t) \\ \ddot{\Theta}_1(t) \\ \ddot{\Theta}_2(t) \end{Bmatrix} = \quad (4)$$

$$\sum_{r=1}^{4} (3v_r^2 - v_r^4 - 1) p_r e^{-v_r p_r t} \left[ \{\mu\}_r^T [M] \{\dot{x}(0)\} \sin\left(\sqrt{1-v_r^2}\, p_r t\right) \right] \{\mu\}_r.$$

Knowing that the initial velocity of the system is $$\{\dot{x}(0)\} = \begin{Bmatrix} v_0 \\ 0 \\ 0 \\ 0 \end{Bmatrix},$$

with $v_o$ assumed to be 0.2 m/s (according to the Periotest manufacturer), Equation (4) can be solved to determine the acceleration of the striking rod, $\ddot{X}_1(t)$, which can be compared to the measured accelerometer signal on the rod.

Due to the nature of these equations a fundamental aspect of the solution is that there will be four distinct frequencies associated with the motion of the system. The frequencies can alternatively be found by calculating the determinate of another matrix, $[K]-\omega^2[M]$ and solving for those values of $\omega$ that make the determinate zero.

$$\text{Determinate of} \begin{bmatrix} K_{11} & K_{12} & K_{13} & K_{14} \\ K_{21} & K_{22} & K_{23} & K_{24} \\ K_{31} & K_{32} & K_{33} & K_{34} \\ K_{41} & K_{42} & K_{43} & K_{44} \end{bmatrix} - \omega^2 \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix} = 0$$

This results in a (long) equation of the form $$A\omega^8 + B\omega^6 + C\omega^4 + D\omega^2 + E = 0 \quad (5)$$

which is used to determine the four values of $\omega$.

During the impact test, the lowest natural frequency of the system is determined from the accelerometer signal contact time. Equation (5) is then used to determine the interface stiffness k that would produce the same lowest natural frequency in the model. This is how the model is used, in conjunction with the accelerometer signal, to estimate the interface stiffness k.

The simulation of the impact response of this system is calculated from the initial value problem in which all the coordinates are initially zero with only the mass $m_R$ having an initial velocity $v_o$.

As the ultimate goal of this model is to understand how the impact response is related to the supporting bone properties (and changes in these properties), model stiffness ($K_T$ and $K_I$), and inertia properties were estimated prior to using the model.

Model results were obtained through the use of a custom Matlab program that solved the equations outlined above for the model of FIG. 21. There will be four resonant frequencies $p_1$ to $p_4$. The lowest (fundamental) frequency is represented as $p_1$ with $p_2$, $p_3$ and $p_4$ corresponding to the higher frequencies in increasing order. To avoid confusion, $\omega_1$ denotes the measured first mode resonant frequency determined from the impact responses. The governing equations for the system shown in FIG. 21 were used in one of two ways:

- the support stiffness k was specified and the Matlab model would determine the natural frequencies ($p_1$ to $p_4$) and the acceleration response of the impact in the time domain, and
- the measured first mode frequency ($\omega_1$) was given and the Matlab model would determine the support stiffness k and the acceleration response of the impact in the time domain.

The analytical model results were compared to measurements only during the contact time and in all cases the model was checked to ensure that only compressive forces existed between the impact rod and the abutment during this interval, as this is the only interval over which the model results are valid.

Analytical Model Parameters

To calculate the support stiffness and damping properties for the in vitro implants the appropriate stiffness values for the internal components in the system were first calculated. The internal stiffness of $K_I$, $K_T$ and $K_F$ were estimated through a combination of in vitro experimentation to directly determine stiffness values and comparison of model results to specific in vitro measurements. Once the internal stiffness components were determined the support stiffness and damping values for extraoral and intraoral implants could be estimated.

The impact stiffness, $K_I$, was estimated directly by clamping a steel block on one side of the abutment while impacting the opposite. The purpose of this is to attempt to isolate the abutment from the support at the implant. The Periotest handpiece was placed in the holding stand and a series of five measurements were taken on 10, 7, 5.5 and 4 mm abutments which were connected to the flanged 4 mm extraoral disk with 20 Ncm of torque. By assuming the steel backing is rigid, the impact stiffness could be calculated from the measured first mode frequency as $$K_I = (2\pi\omega_1)^2 m_R. \quad (6)$$

The results for the different abutment sizes are shown in the following Table 4.

TABLE 4

Calculated impact stiffness ($K_I$) for different length abutments.

| | $\omega_1$ (Hz) | $K_I$ (N/m) × $10^6$ |
|---|---|---|
| 10.0 mm Abutment | 2624 ± 22 | 2.51-2.60 (2.56) |
| 7.0 mm Abutment | 2542 ± 16 | 2.37-2.43 (2.40) |
| 5.5 mm Abutment | 2690 ± 7 | 2.67-2.70 (2.68) |
| 4.0 mm Abutment | 2836 ± 13 | 2.96-3.01 (2.98) |

The $\omega_1$ values reported in Table 4 are the average of the five readings with the standard deviation of the measurements for each abutment. The impact stiffness ($K_I$) is reported as a range to reflect the measurement variation, with the $K_I$ from the average $\omega_1$ value shown in brackets. Table 4 shows that for different length abutments there are variations in the measured $\omega_1$ values resulting in different values for $K_I$. These differences are likely due to geometric differences which exist between the abutments. While the outer diameter for the different length abutments are the same, the internal dimensions and the connecting screw details differ. Due to these differences, the $K_I$ value used with the analytical model was the average value shown in brackets and was specific to each abutment.

The torsional stiffness $K_T$ was initially estimated based on the assumption that the abutment behaves as a cantilever beam such that $$K_T = \frac{3EI}{L_T}. \quad (7)$$

The length of the cantilever, $L_T$, is determined by $L_T=L_A-L_O$ where $L_A$ is the length of the abutment and $L_O$ is the distance from the top of the abutment to where the Periotest rod strikes. Using E=110 GPa for titanium and approximating the abutments as solid cylinders allows for the calculation of $K_T$.

Equation (7) assumes a rigid, fixed connection at the implant/abutment joint. However, the screw connection between the implant and abutment will not provide an ideal fixed connection. As a result, the torsional stiffness ($K_T$) determined in Equation (7) will over-estimate the true torsional stiffness. Additionally, Equation (7) does not take into account any shear effects, which are likely to be important since the abutments are relatively short. To account for the effects of shear and a non-ideal joint connection between the implant and abutment the value of $K_T$ is adjusted empirically as discussed in the following section.

As a test of the developed model, the simulated un-damped acceleration response ($\beta=0$) was compared to one of the measured acceleration signals for the 10 mm implant with a 10 mm abutment. The 10 mm abutment was chosen as the amplitude of its second mode was found to be largest and would better illustrate model and measurement results. The results of the comparison can be seen in FIG. 22A, which shows the acceleration response of 16 impact measurements and the predicted acceleration response from the model using $K_I$ and $K_T$ as given above. A support stiffness k=1.8-2.1 (1.9) GPa was found by matching the model first mode frequency to the measured frequency $\omega_1$=1500±14 Hz determined from the impact tests. The range of k reflects the variation in measured $\omega_1$ with the k determined from the average measured $\omega_1$ in brackets. To directly compare the model acceleration response to the measurements, the model response was "normalized" by approximately matching the model acceleration amplitude with the measured accelerometer signal amplitude (this normalization was used since the calibration of the Periotest accelerometer was unknown and its magnitude depends on the initial speed of the Periotest rod which is also unknown for each individual strike).

Figure 22A:
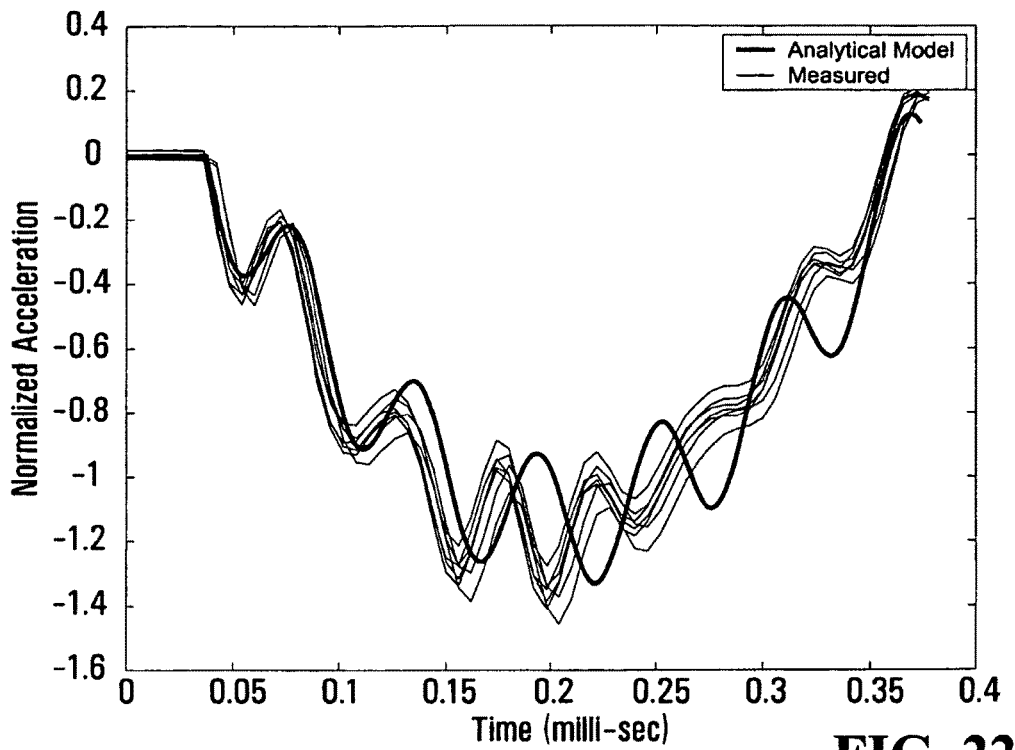
FIGS. 22A and 22B are graphs comparing measured acceleration response and predicted acceleration response.

While the relative amplitudes of the accelerations between the first and second modes are predicted well (the amplitudes of the peaks appear to match), there is a noticeable second mode frequency difference between the measured response and the model results shown in FIG. 22A. The model appears to under-predict the second mode frequency. To improve the predictions from the model, the value of $K_T$ estimated previously in Equation (7) was reduced to $$K_T = 0.26\left(\frac{3EI}{L_T}\right) \quad (8)$$

to account for any additional flexibility or shear effects as described previously.

Figure 22B:
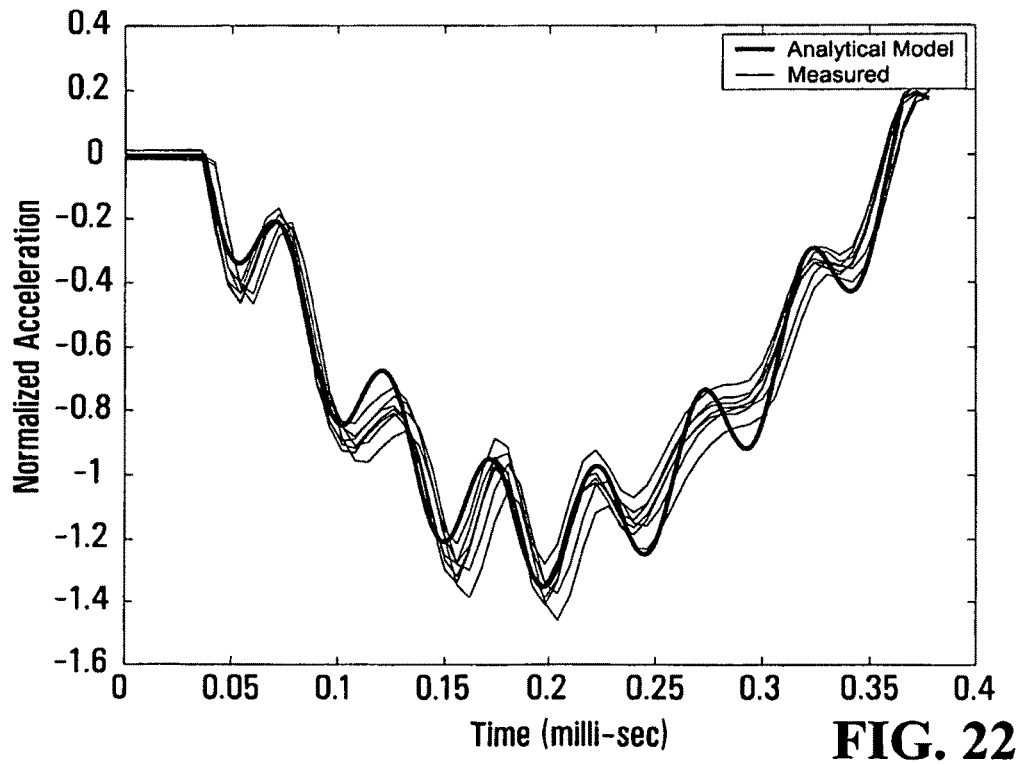

With the reduced $K_T$, a new support stiffness k=6.8-8.4 (7.5) GPa was determined for the 10 mm implant and 10 mm abutment. The resulting (un-damped) signal, shown in FIG. 22B, shows much better agreement with the measured signal. While the geometry of the supporting material will affect the relationship between k and the elastic modulus, the average determined k=7.5 GPa value compares well to the modulus of elasticity of FRB-10 which is 9.3 GPa. The 0.26 correction factor shown in Equation (8) was used throughout all subsequent simulations.

Model Damping Calculation

Figure 23:
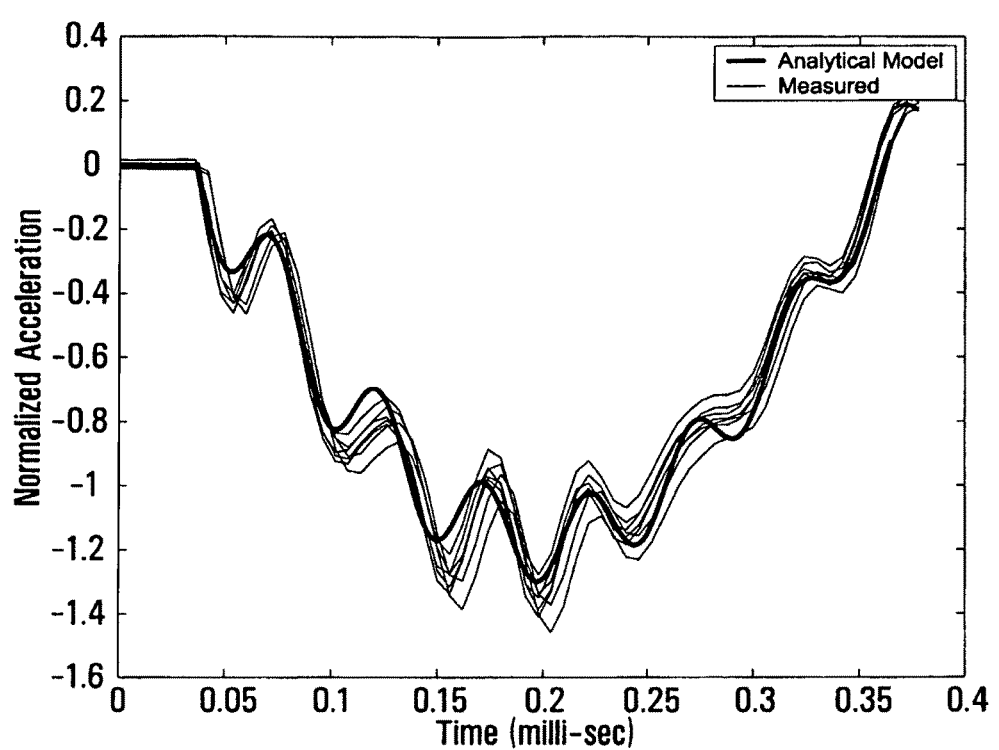
FIG. 23 is a graph comparing measured acceleration response with damped model acceleration response.

To estimate the damping coefficient, $\beta$, its value was increased in the model until the decay in the second mode amplitude approximately matched the measured response as shown in FIG. 23. Again, a 10 mm intraoral implant with a 10 mm abutment was used. As can be seen, the damped model response agrees very well with the measurements. The value of the damping coefficient found was $\beta=2.45\times10^{-7}$ sec in this case. This damping proportionality constant results in a damping ratio for each mode as shown in Table 5. The determined value of the damping coefficient ($\beta=2.45\times10^{-7}$ sec) is used for all subsequent model simulations of implants placed in FRB-10.

TABLE 5

Calculated damping ratio for each mode for implants placed in FRB-10

| Mode | Damping Ratio (%) |
|---|---|
| 1 | 0.1 |
| 2 | 1.5 |
| 3 | 4.8 |
| 4 | 6.3 |

Effect of Flange

Figure 24:
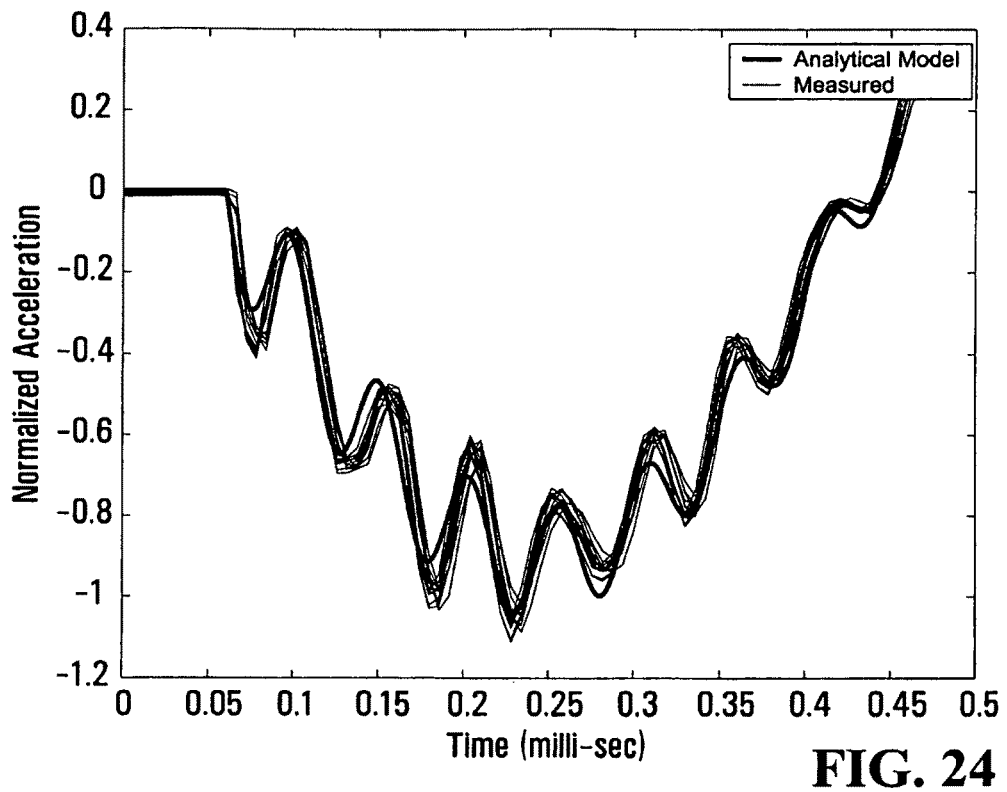
FIGS. 24 and 25 are graphs comparing measured acceleration response with damped model acceleration response with and without flange.

To test the effect a flange has on implant stability, impact measurements on a 3.75×4 mm flanged extraoral implant with a 10 mm abutment were performed. The flange on the implant was then removed with a lathe and the tests with the 10 mm abutment were repeated. The removal of the flange resulted in the average measured first mode frequency decreasing from $\omega_1$=1536±9 Hz to $\omega_1$=1337±12 Hz, indicating that the flange was providing extra support to the implant. The results are shown in FIG. 24 for the 4 mm flangeless extraoral implant and in FIG. 25 for the 4 mm flanged extraoral implant.

If the previously determined $K_I$ and $K_T$ values for a 10 mm abutment are used with the analytical model the supporting stiffness (k) for the flangeless 4 mm implant was 7.3-8.1 (7.7) GPa, which agrees well with the k=6.8-8.4 (7.5) GPa value found for the 10 mm implant previously. Since k is represented as a stiffness per unit length the two implants should have similar stiffness values, as they are supported by the same material. The results of 16 impact measurements with a 4 mm flangeless implant with a 10 mm abutment compared to the model results with k=7.7 GPa are shown in FIG. 25A. The predicted acceleration response shows excellent agreement with the flangeless implant measurement.

To determine the value of $K_F$ in the model, $K_T$ and $K_I$ were as determined for a 10 mm abutment and k was set to 7.7 GPa for the flanged implant case. The effective distance that $K_F$ was applied was taken as half the width of the 2 mm flange plus the radius of the implant (1.875 mm) to give r=2.875 mm. The value of $K_F$ in the model was then increased until the model first mode frequency matched the average measured first mode frequency of the flanged readings ($\omega_1$=1536 Hz) which occurred when $K_F$=3.65×10$^7$ N/m. A comparison between the flanged measured results and model results is shown in FIG. 25.

Figure 25:
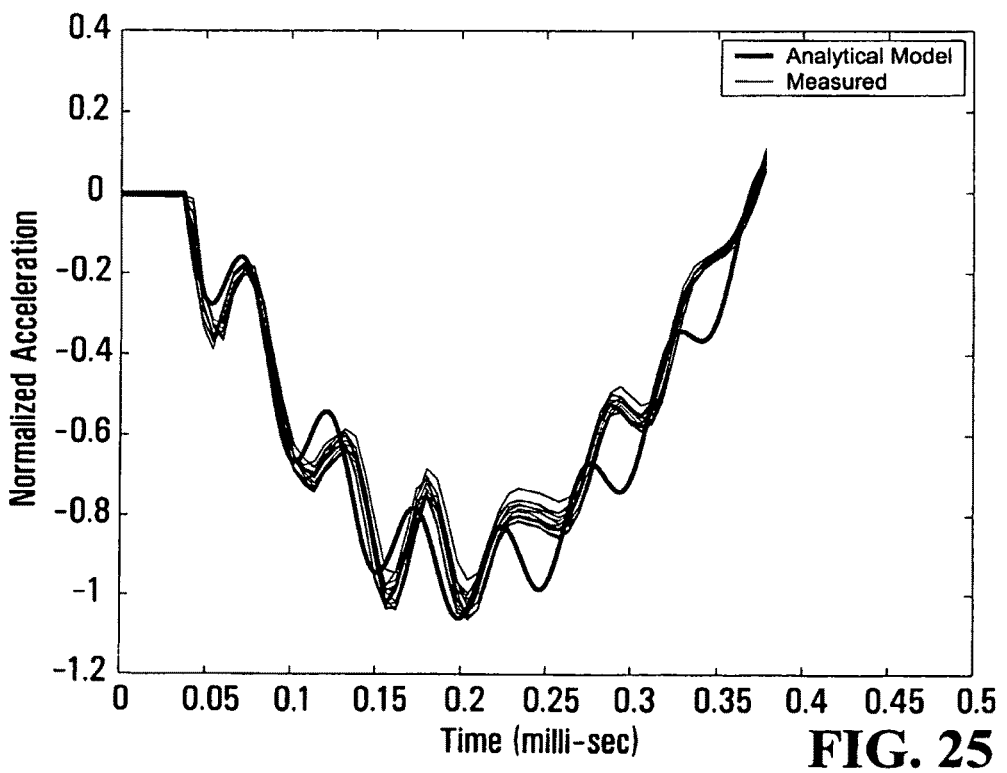
Figure 26A:
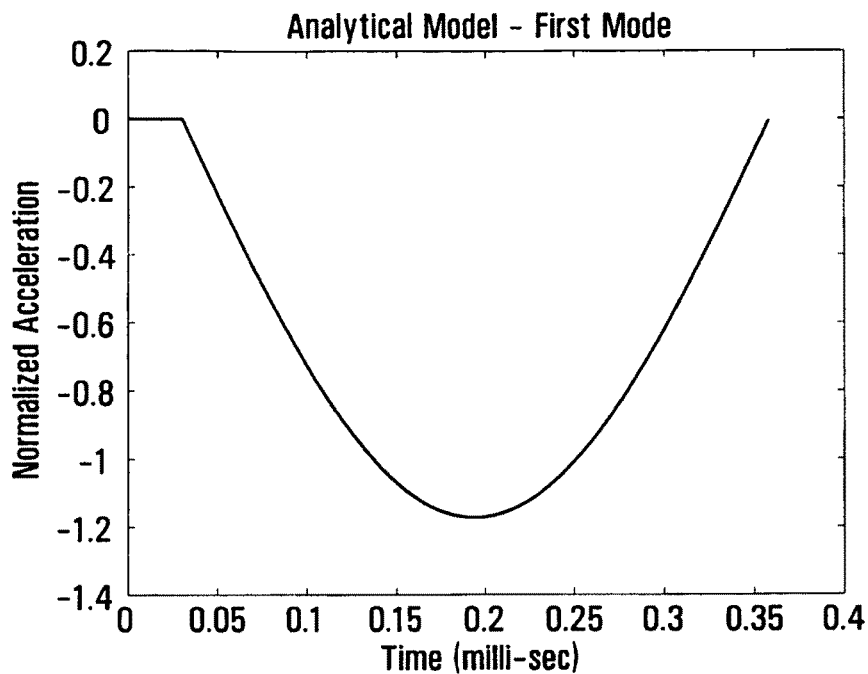
FIG. 26A to 26D are graphs depicting modal acceleration components.
Figure 26B:
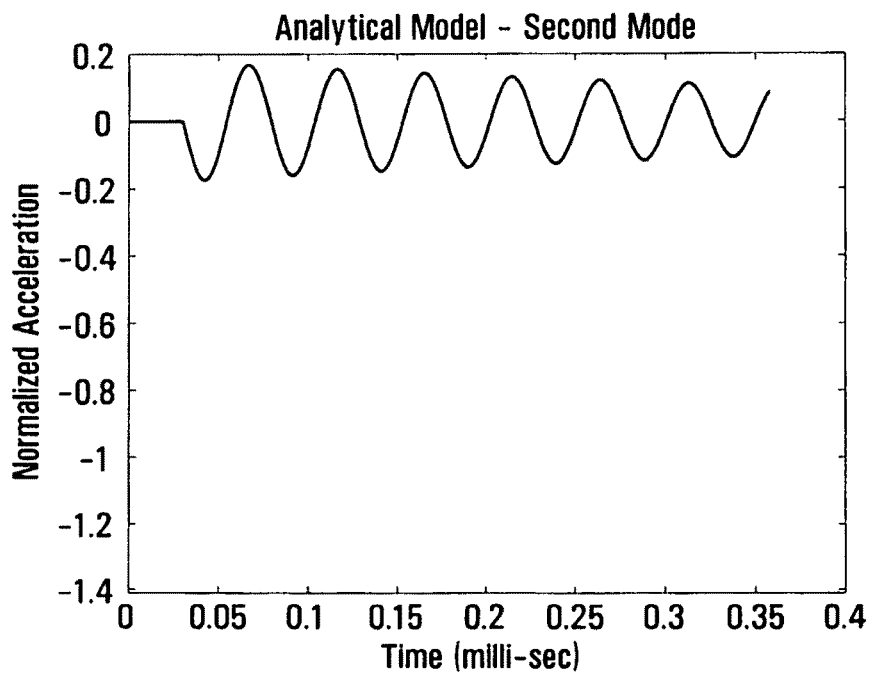
Figure 26C:
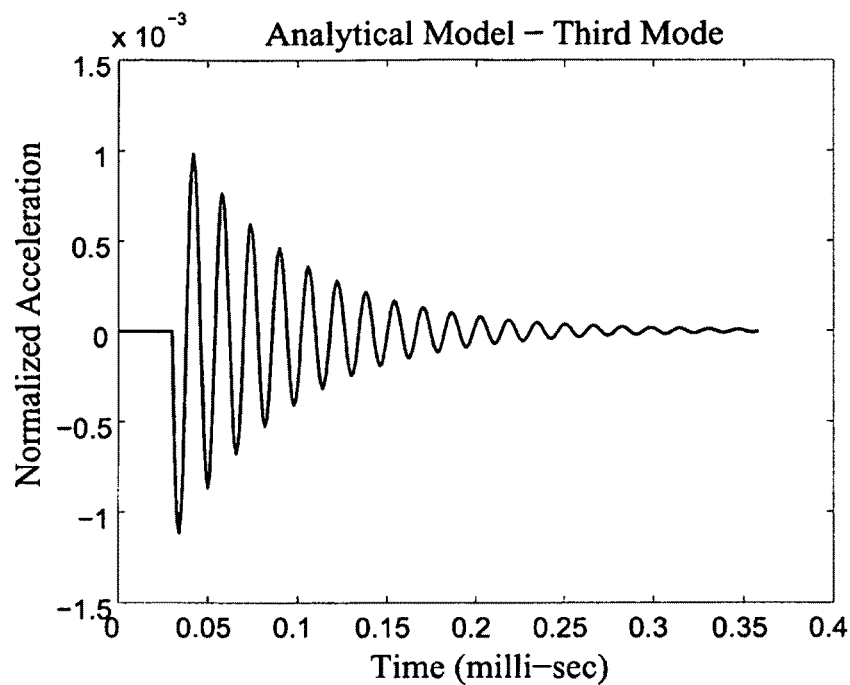
Figure 26D:
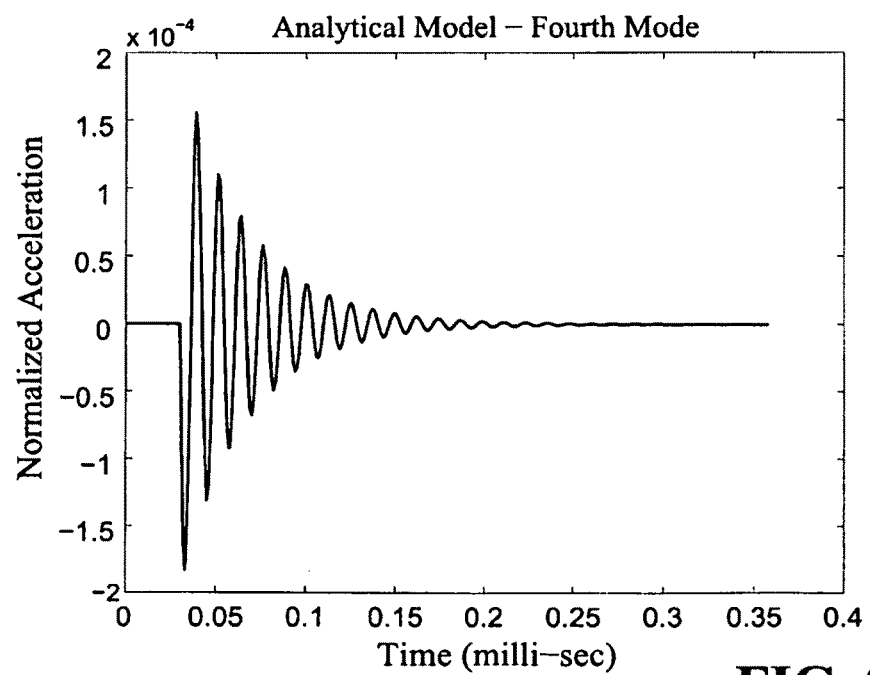

In FIG. 25 the model results do not match the measured signals as well as in previous tests. In particular, the predicted higher frequency component does not agree as well as for the flangeless implant. One possible explanation is that when the implant was placed in the FRB-10 some of the epoxy used to secure the implant ended up under the flange, bonding the flange to the FRB-10 surface providing not only vertical but horizontal support for the flange as well (which was not included in the model).

Model Acceleration Response

The damped model acceleration response shown in FIG. 23 is in actuality a superposition of four different acceleration responses, which are shown in FIG. 26. FIG. 26 shows four modal acceleration components for a 10 mm implant with a 10 mm abutment and k of 7.5 Gpa. Note that the third and fourth mode responses have been magnified for clarity. The maximum amplitude of the second mode response is approximately an order of magnitude smaller than the maximum amplitude of the first mode response. The maximum amplitude of the third and fourth modes is approximately three and four orders of magnitude smaller, respectively. Only the first and second modes make noticeable contributions to the overall response. Additionally, FIG. 26 also demonstrates the effects of damping in the model with the higher modes being damped out more quickly than the lower ones.

Model Validation

While the model simulations in previous sections indicate a very good agreement with the actual acceleration response, this was for a limited number of specific tests. In order for the model to be effective it should be able to accurately simulate a broad range clinical situations. To this end, the fundamental frequency results from measurements utilizing different implant-abutment parameters were compared to the model results. Tests with different striking heights, different length implants and with different abutment lengths were conducted to evaluate the suitability of the model under different geometric conditions while holding k constant for each disk used.

The analytical model frequency results were calculated using the previously determined stiffness values. For the FRB disk containing the 4 mm implant k was 7.7 GPa and for the disk with the 10 mm implant k was 7.5 GPa. These values were held constant for all the subsequent comparisons. Similarly, for all of the in vitro results, $K_I$ for each length abutment was as listed in Table 4, $K_T$ values were as calculated from Equation (8) and $K_F$, where appropriate, was 3.65×10$^7$ N/m.

Variations in Striking Height

One technique used to validate the model was to compare the model results with experimental results obtained from striking a 10 mm abutment at different heights above the surface of the FRB disk. Measurements were completed at different striking heights along a 10 mm abutment for the 3.75×4 mm flanged extraoral implant and 4×10 mm intraoral implant. The measurements were taken by striking the top corner of the abutment and then lowering the handpiece 1, 2, 3, and 4 mm. Five readings were taken at each height.

Figure 27A:
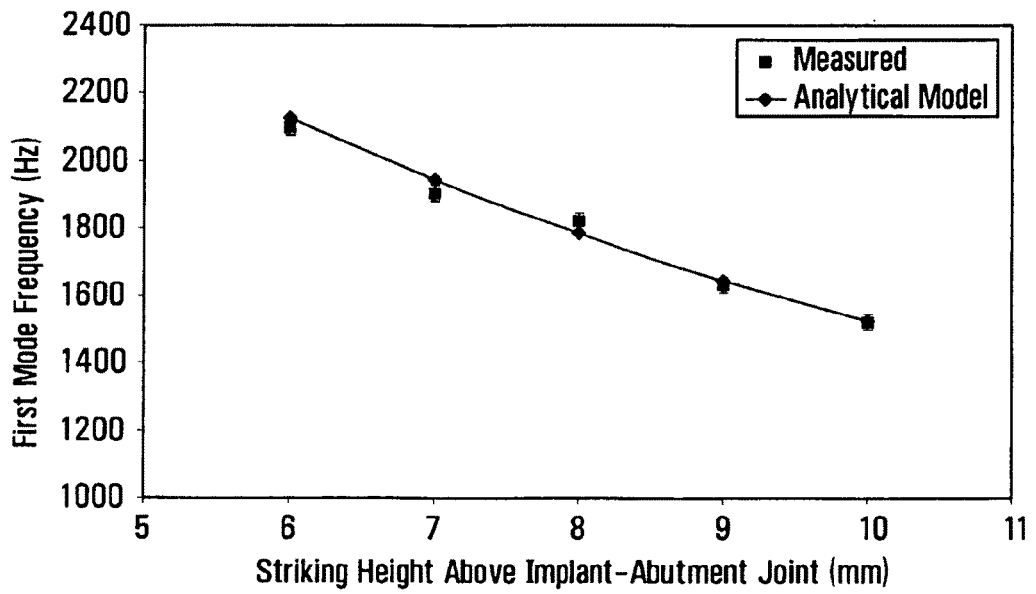
FIGS. 27A and 27B are graphs comparing model results with measurements for abutment strike at different heights.
Figure 27B:
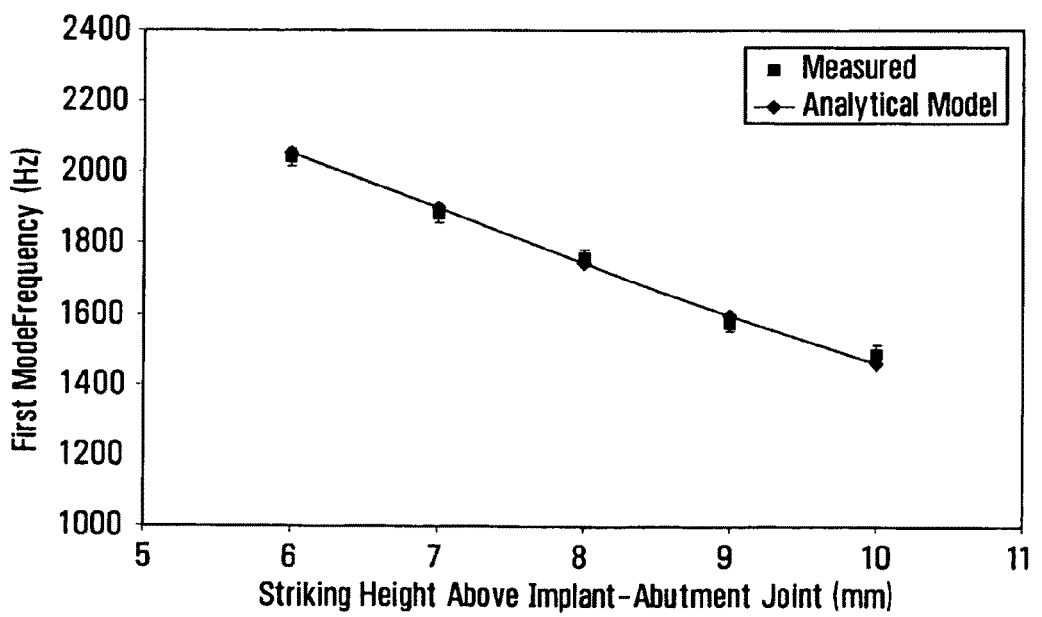
Figure 28A:
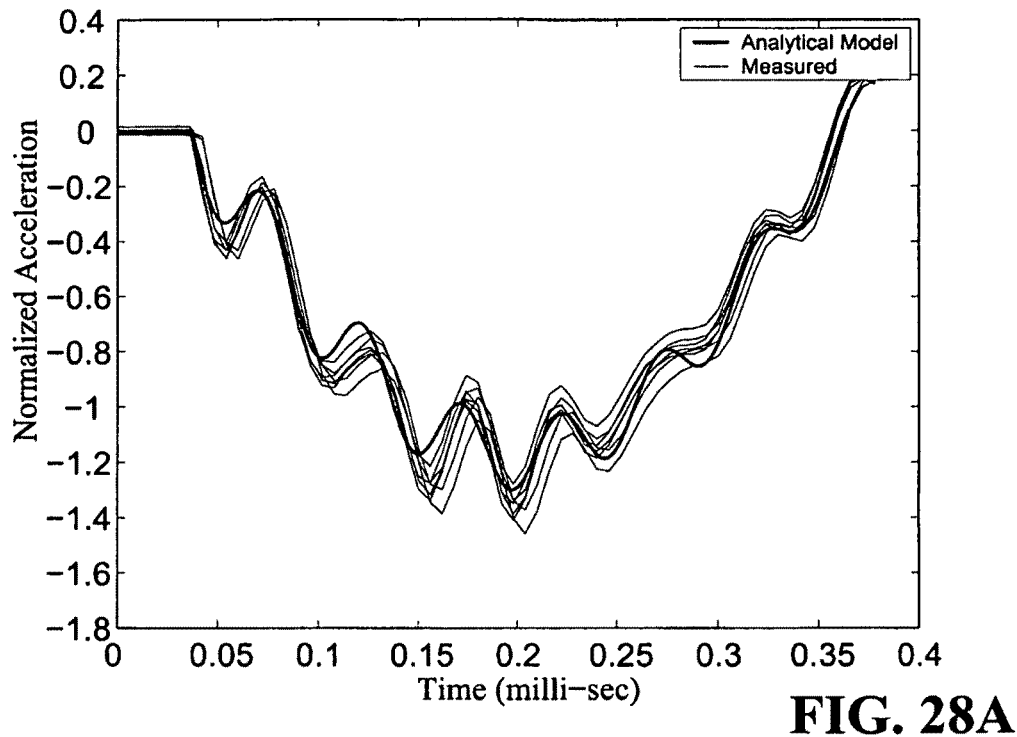
FIGS. 28A to 28D are graphs comparing model results with measurements for abutment strike at different points along the abutment.
Figure 28B:
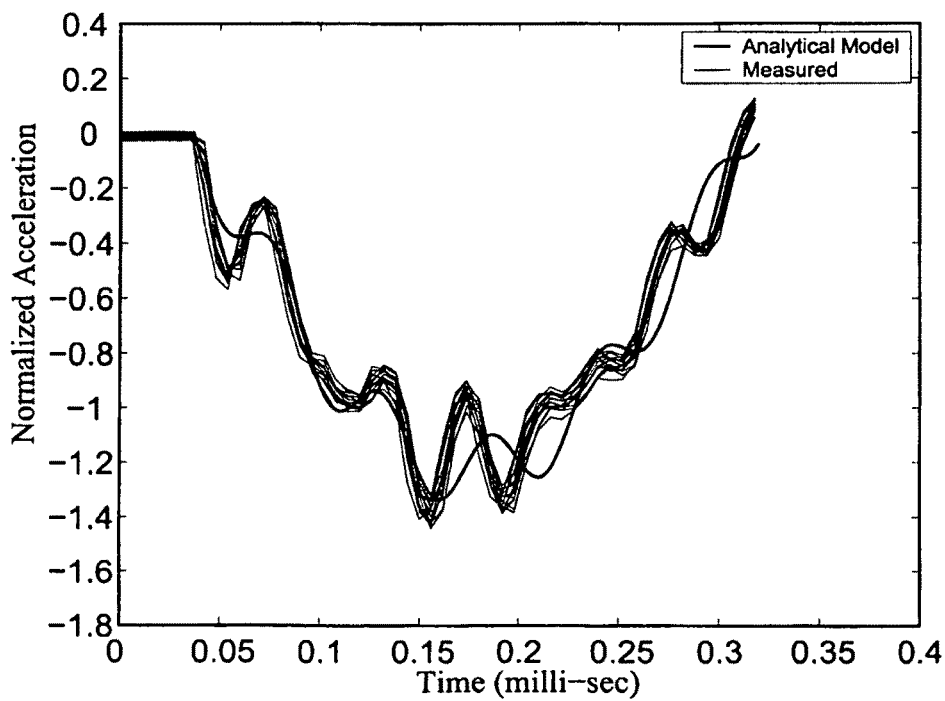
Figure 28C:
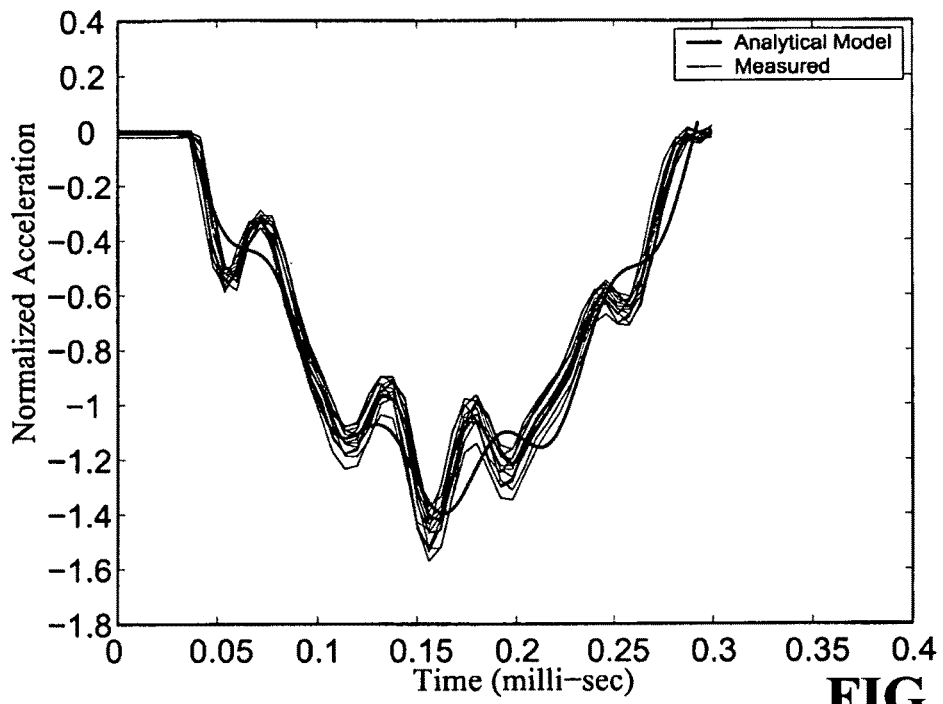
Figure 28D:
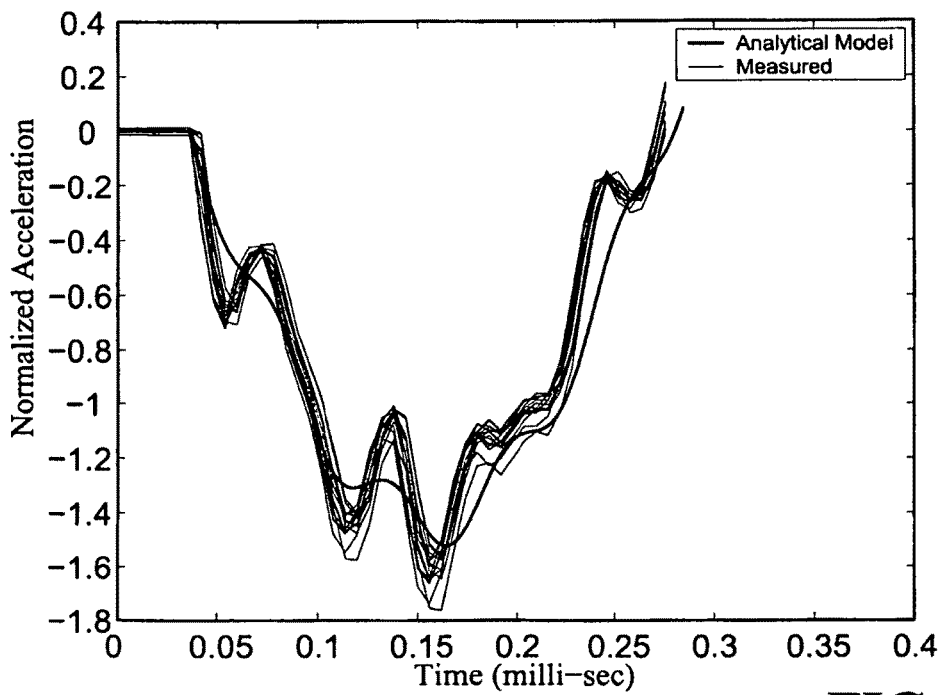

The measured first mode frequencies ($\omega_1$) are compared to the predicted model first mode frequencies ($p_1$) in FIGS. 27A and 27B. FIG. 27A shows the comparison using a 10 mm intraoral implant, while FIG. 27B shows the comparison using a 4 mm extraoral implant. In each graph, five measured frequency values are averaged and the error bars shown represent two standard deviations of the repeatability and reproducibility of the measurement system (±24 Hz). The model results agree very well with the measurements for both implants and demonstrate the sensitivity of the impact method to variations in striking height. To reduce measurement variation due to changes in striking height measurement protocols should ensure that impacts occur at an easily identifiable and repeatable position (such as the superior rim of the abutment).

To compare the second mode frequency to the model results at different striking heights, the model predicted acceleration response for the 10 mm implant case was directly compared to measurements as shown in FIG. 28. In FIGS. 28A through 28D, the abutment is struck at the top of the abutment, 2 mm from the top of the abutment, 3 mm from the top of the abutment, and 4 mm from the top of the abutment, respectively. The measured second mode frequency appears to match the model frequency quite well for the different striking heights, with the exception of FIG. 28B where the model under-predicts the second mode frequency. The model predicted amplitude of the second mode frequency appears to be smaller than the measurements in all but FIG. 28A.

While the first mode frequency in both the measurements and model match very well, there is some discrepancy between the model results and the measurements when comparing the second mode frequency and amplitude. These differences may be due to assumptions made to take into account the deformation of the abutment. At different striking positions along the abutment $K_I$ may have different values, as the rim of the abutment will likely be less stiff than the wall of the abutment. There may also be some errors introduced by the manner the model handles bending. Modeling bending with a torsional spring in Equation (8) may be too simplistic to provide a higher level of agreement. Although the level of agreement in FIG. 28 is not as good as in previous measurements, the level of agreement is still reasonable considering the simplifying assumptions made in the model. While there is some discrepancy between the predicted higher frequency components in the accelerometer signal and measurements the lower frequency or "contact time" shows excellent agreement in all cases. It should be noted that clinically, only impacts at the top are relevant.

Variation in Abutment Length

Figure 29A:
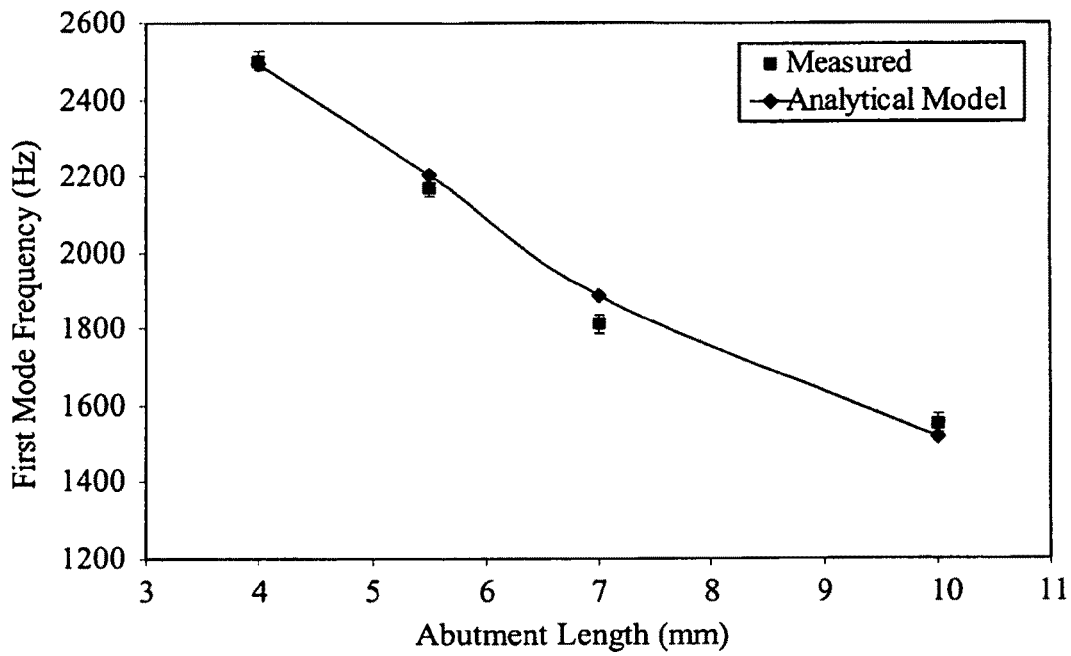
FIGS. 29A and 29B are graphs comparing model results with measurements for implants of different length.
Figure 29B:
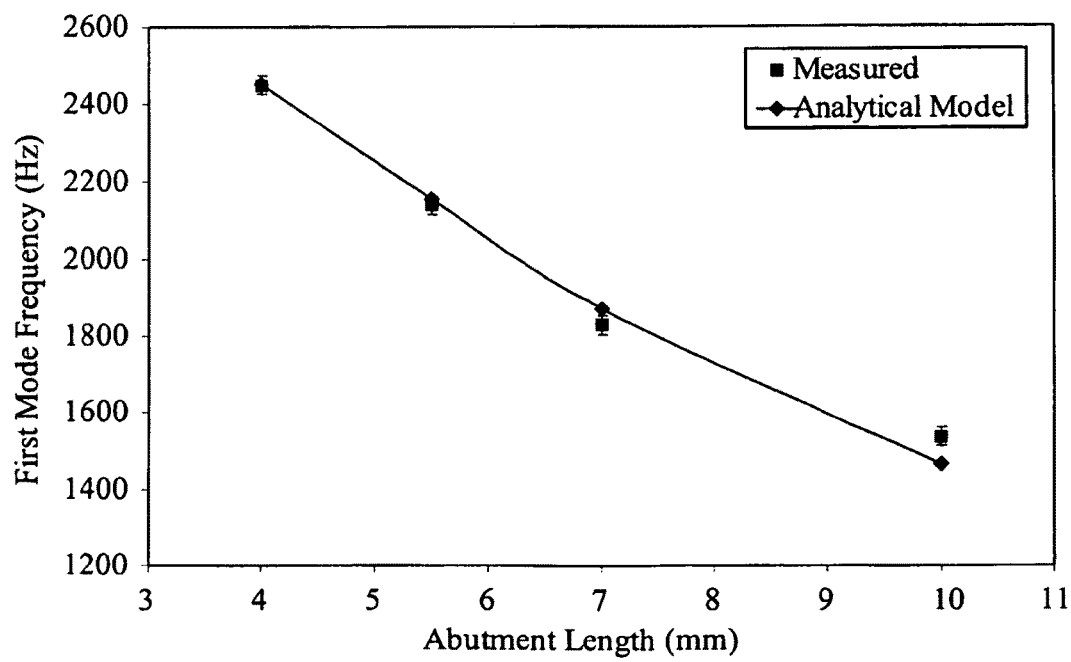
Figure 30A:
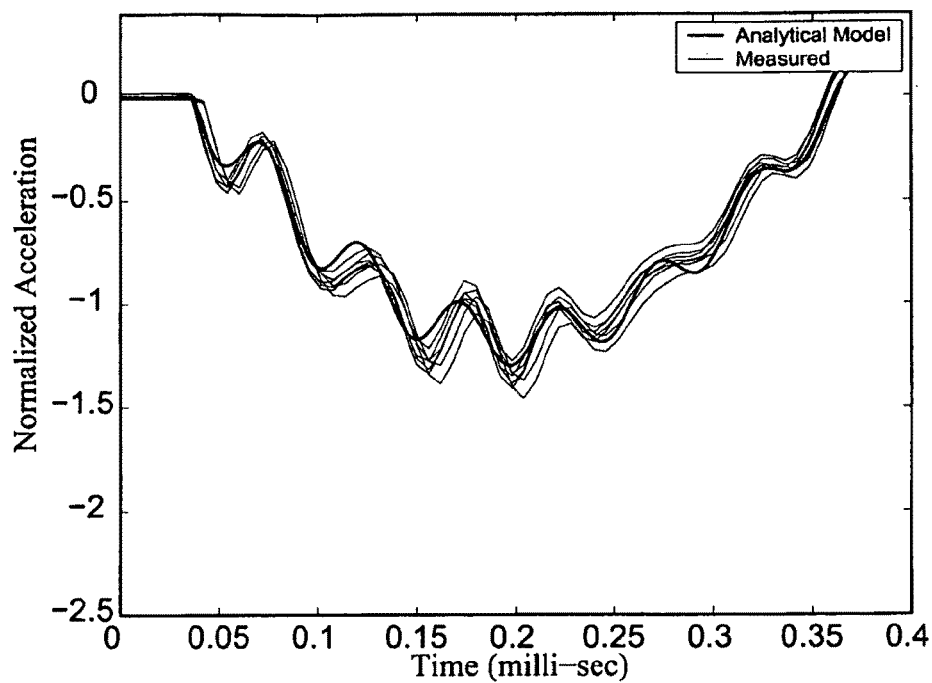
FIGS. 30A to 30D are graphs comparing model results with measurements for abutments of different length.
Figure 30B:
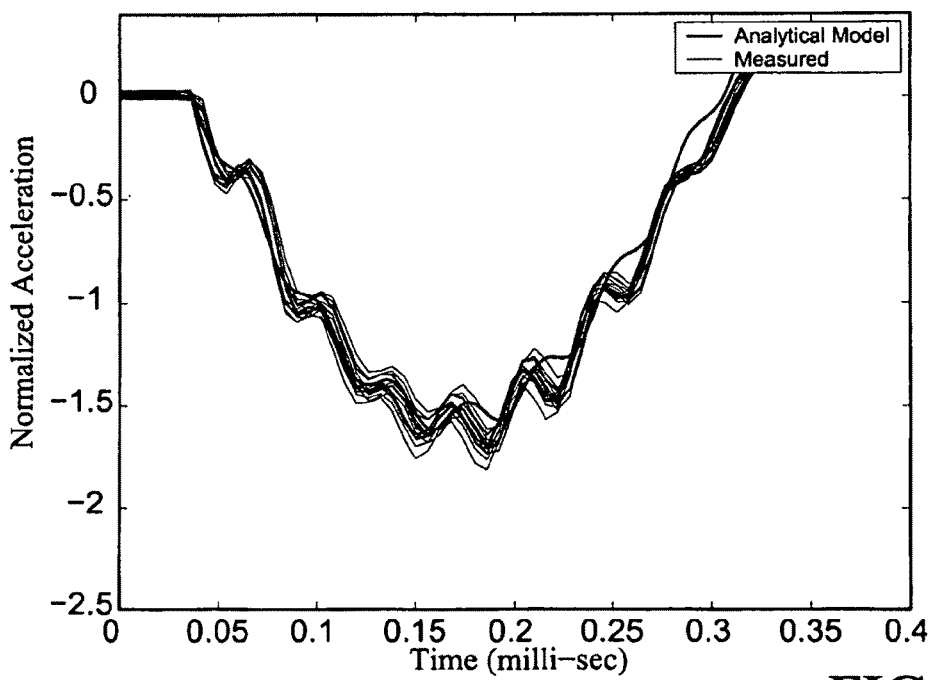
Figure 30C:
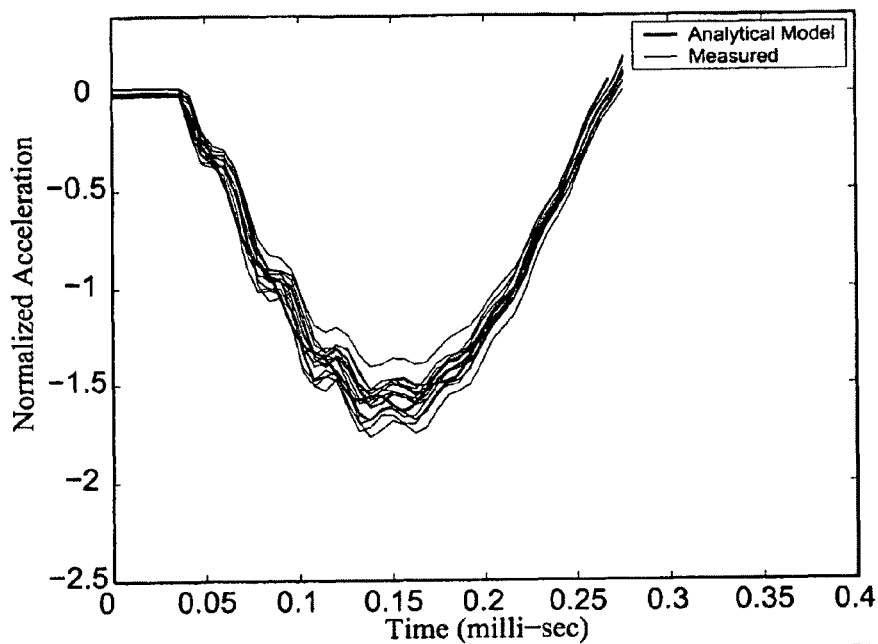
Figure 30D:
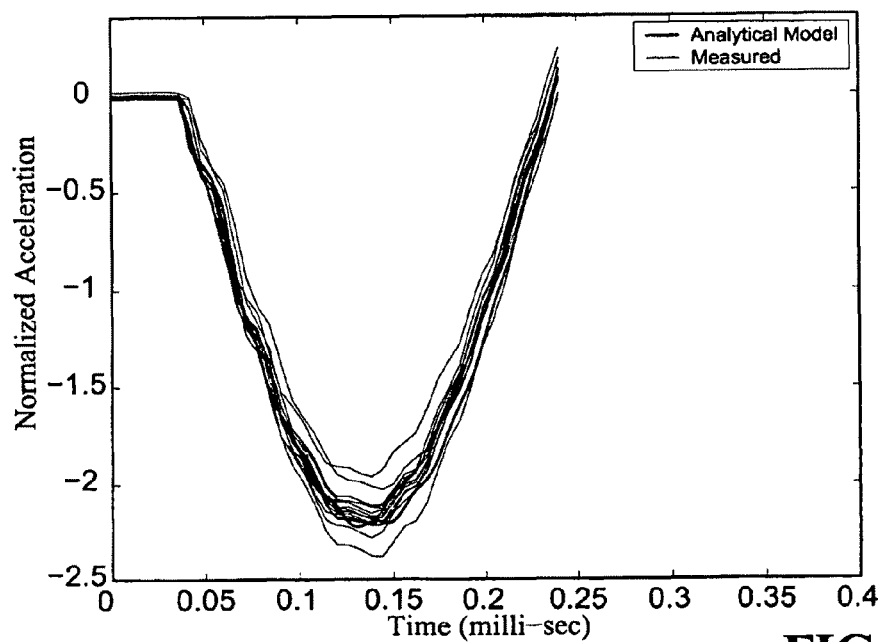

Since different abutment sizes are commonly used with implants, it is important to compare the model results with different sized abutments. Both the 3.75×4 mm flanged extraoral implant and the 4×10 mm intraoral implant had 4, 5.5, 7 and 10 mm abutments connected with a torque of 20 Ncm. Each implant was tested five times on the top rim of each abutment. As in the previous section, model first mode frequencies ($p_i$) were compared to the measured fundamental frequencies ($\omega_1$). The results of this comparison can be found in FIG. 29. FIG. 29A shows the comparison for a 10 mm intraoral implant, while FIG. 29B shows the comparison for a 4 mm extraoral implant. The measurement results in the figure are the average of the five readings and the error bars are two standard deviations of the repeatability and reproducibility of the measurement setup. The results in FIG. 29 again show good agreement between the model predicted fundamental frequency and the measured values for the abutments tested. The agreement between the predicted values and measurements provides evidence that the model correctly accounts for the effect different length abutments have on the fundamental frequency.

The predicted model acceleration response for the different abutment sizes with a 10 mm implant are compared to the measured results in FIG. 30. FIGS. 30A through 30D show the comparison using a 10 mm abutment, a 7 mm abutment, a 5.5 mm abutment, and a 4 mm abutment, respectively. The second mode amplitude and frequencies match the measured values quite well in all of the cases shown.

Analytical Model Simulations

One use of the developed analytical model is to investigate expected changes in the first mode resonant frequencies of Branemark implant-abutment systems due to simulated changes in bone properties. Three changes in bone structure were investigated with the analytical model; changes in the supporting bone stiffness, changes to the damping properties of the bone and marginal bone height losses around the neck of the implant. The model was then used to determine if it would be possible to predict the effect a flange has on implant stability in vivo. The flange stiffness determined previously represents a flange bonded to the support surface (such as might occur when the flange was osseointegrated with the bone surface). Simulations with this flange stiffness will provide simulations for cases in which the flange is providing a maximum amount of support.

Simulation of Changes to Supporting Stiffness

Changes in the supporting stiffness can be modeled by changing the stiffness of the horizontal and vertical springs (k) in the analytical model. The simulations of changes in k were done over a range of implant-abutment geometries, a 4 mm extraoral implant with 5.5 mm and 7 mm standard abutments and a 10 mm intraoral implant with 5.5 mm and 7 mm standard abutments. For the simulations, all impacts occur at the top rim of the abutments. The stiffness k was varied from 0.75 to 15.0 GPa for each implant with each different abutment. The variations in k between 0.75-15.0 GPa represents the range of supporting stiffness used to produce first mode frequencies equivalent to those measured in vivo in patients.

Figure 31A:
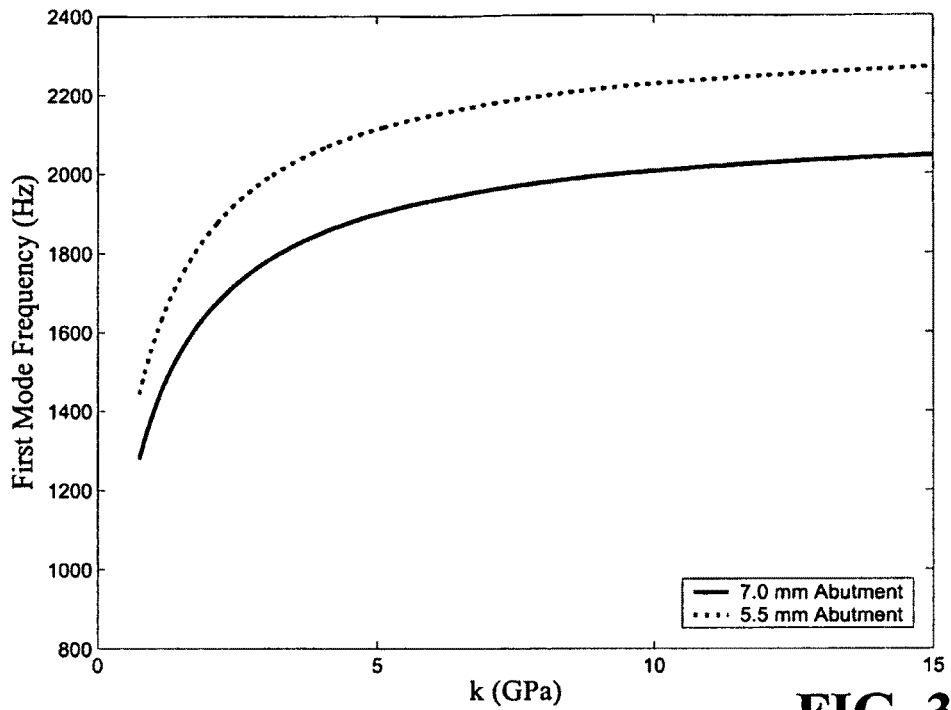
FIGS. 31A and 31B are graphs depicting effects of varying support stiffness on the first mode frequency for two abutment lengths.
Figure 31B:
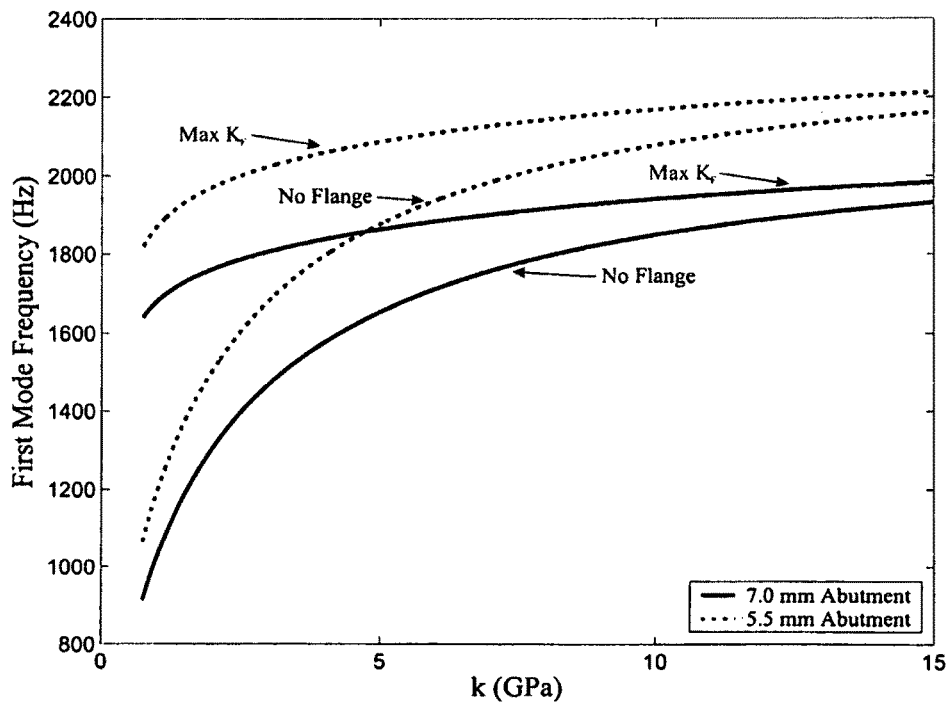

The effects of varying k on the first mode frequency are shown in FIGS. 31A and 31B. FIG. 31A shows the effect using a 10 mm intraoral implant, while FIG. 31B shows the effects of using a 4 mm extraoral flanged implant. For both implants, the effect of increasing the abutment length from 5.5 to 7 mm lowered the resonant frequency. For the flanged 4 mm implant two separate simulations were done for each abutment, one simulation without a flange and one with the flange value determined from the in vitro simulations as described previously. The $K_F$ value determined was for a flange with a thin epoxy layer bonding it to the FRB disk surface, and was taken as a maximum possible flange contribution. In FIG. 31B the upper curve for each abutment represents the maximum flange effect and the lower curve shows the effect without a flange. In a clinical situation the flange stiffness would produce an effect between the maximum and minimum curves shown. From FIG. 31, the 5.5 mm abutment has a slightly greater change in frequency over the range of k than the 7 mm abutment for both implants.

FIG. 31B also shows that the curves without a flange have a greater frequency range than with a fully integrated flange. The inclusion of a flange has the effect of reducing the sensitivity of the resonant frequency to changes in the support stiffness k.

In FIGS. 31A and 31B, a steeper slope indicates a greater frequency sensitivity to changes in k. For both implants the curves start to plateau after approximately 5 GPa. This indicates that as the supporting bone stiffness (k) continues to increase the resonant frequency becomes less sensitive to these changes. For cases in which the supporting bone stiffness is high, the measurement system may be unable to quantify changes occurring in the bone properties. However, for values of k in this upper range, the implant is generally considered well integrated and not in immediate danger of failing, so the changes which may occur in k are less important. Fortunately, the impact test is much more sensitive to changes in supporting bone properties for a poorly integrated implant that may be in danger of failing.

Simulation of Changes in Damping Properties

Many studies utilizing the Periotest often erroneously refer to the device as measuring the damping characteristics of the interface. To estimate the effects due to changes in damping the damping coefficient ($\beta=2.45\times10^{-7}$ sec) used in the model was doubled, then quadrupled for a 10 mm intraoral implant with a 10 mm abutment as shown in FIG. 32.

Figure 32:
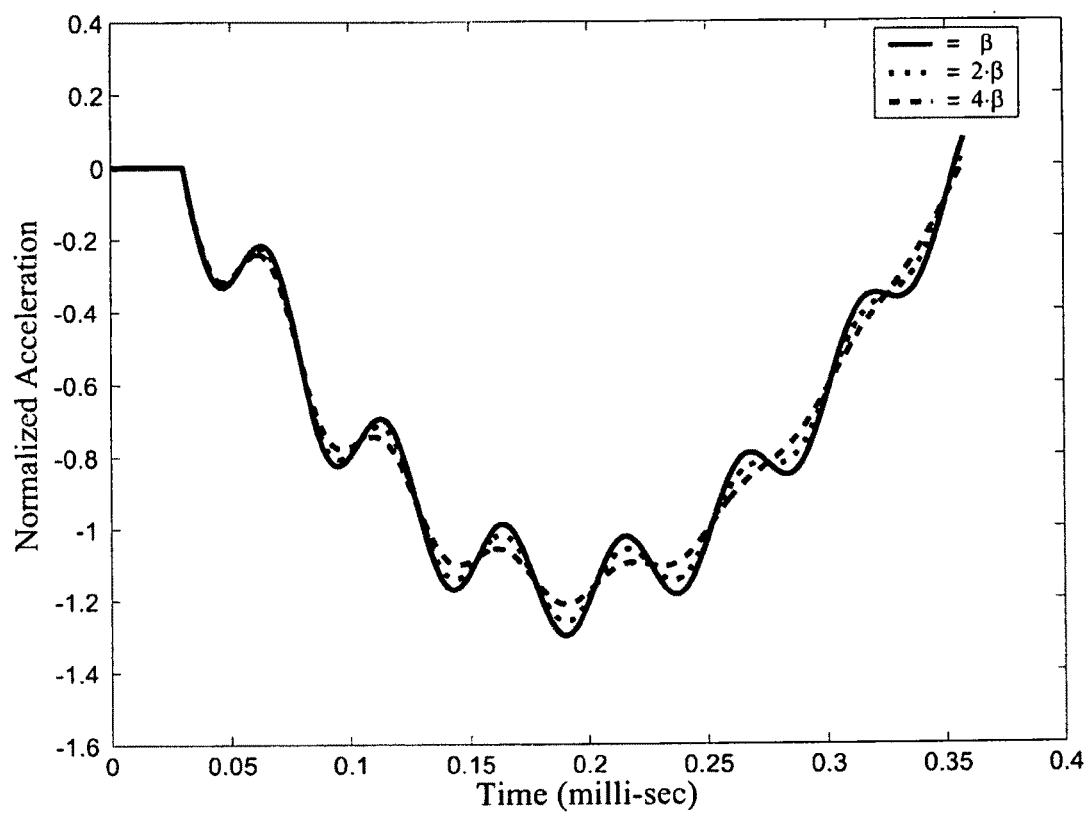
FIG. 32 is a graph depicting effects of changing the damping coefficient on the model acceleration response.

FIG. 32 demonstrates that as the damping coefficient is increased the amplitude of the second mode frequency is affected, however, there is virtually no change in the contact time. Devices that utilize contact time or resonant frequency measurements (such as the Periotest and Osstell) are therefore very insensitive to changes in damping when implant systems are considered.

Simulation of Bone Loss

One of the mechanisms with which an implant can fail is from crestal bone loss around the head of the implant. It has been suggested that, in some cases, implant failure may be the result of a "positive feedback" loop in which bone loss at the top of the implant leads to more bone loss and this continues until implant failure. If implants can be identified as having bone loss early enough, preventative measures may save the implant. As such, the ability to measure implant bone loss would be of clinical value. To this end, the model was used in a number of simulations to help determine how bone loss may manifest itself in the impact measurements.

For the simulations, bone loss starts at the top of the implant and progresses toward the base. For the bone loss calculations, two implant-abutment geometries were used, a 4 mm extraoral implant with a 5.5 mm abutment and a 10 mm intraoral implant with a 5.5 mm abutment. In the simulations the engagement length was reduced 5 mm in 0.5 mm increments for the 10 mm implant, and 2 mm in 0.5 mm increments for the 4 mm implant. This was done for k values of 1, 5, and 10 GPa.

Figure 33A:
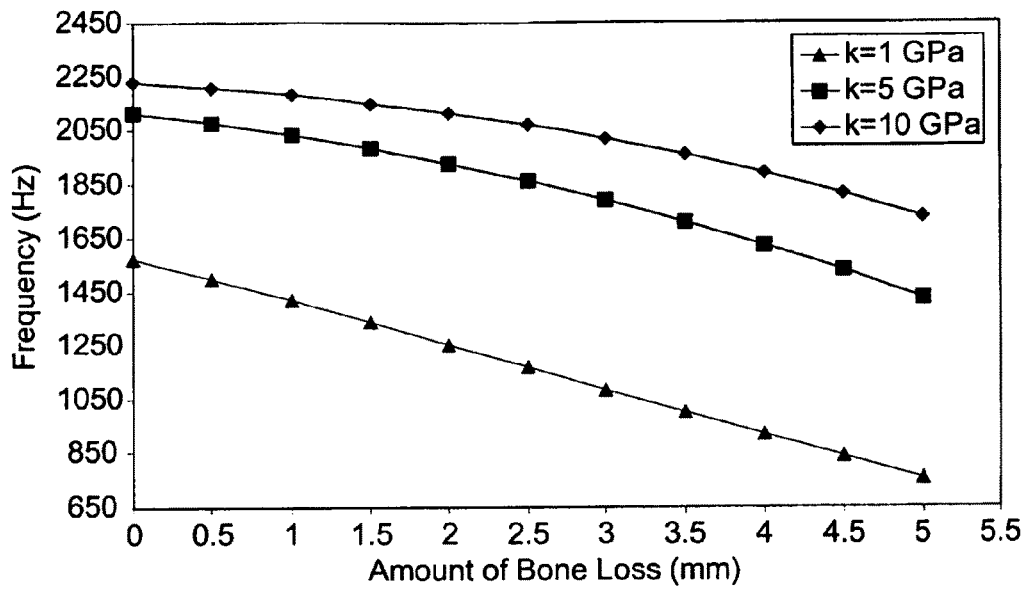
FIGS. 33A and 33B are graphs depicting effects of bone loss from the top of the implant towards the base on the first mode resonant frequency.
Figure 33B:
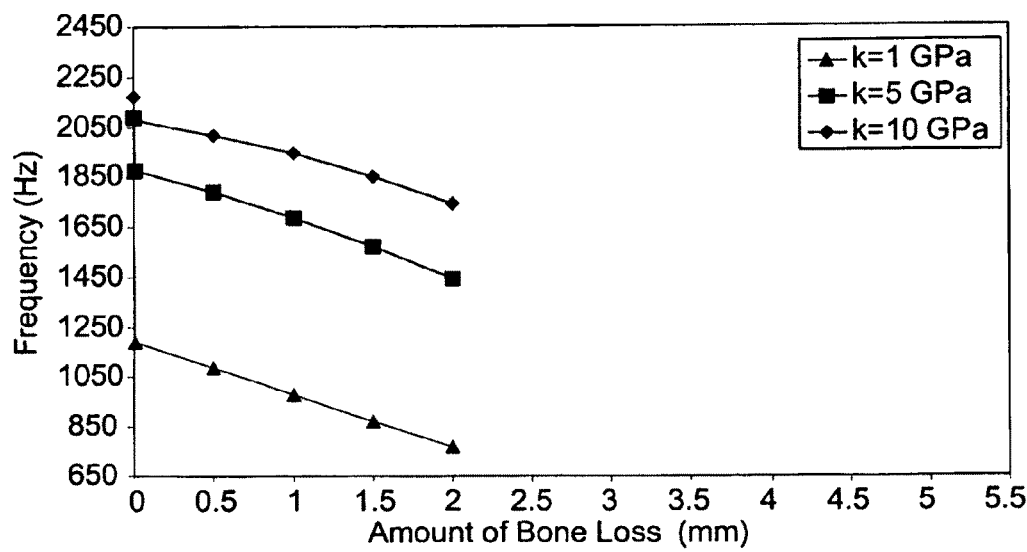

The simulations of the changes in the first mode frequency due to bone loss around a 10 mm intraoral implant is shown in FIG. 33A and for a 4 mm extraoral flanged implant in FIG. 33B. The k=1 GPa curve in FIG. 33A shows substantially a linear relationship between bone loss and first mode frequency. At higher support stiffness values the relationship between the amount of bone loss and first mode frequency is nonlinear and there is a smaller overall change in frequency corresponding to the bone loss. For k=1 GPa the first mode frequency changes by approximately 800 Hz (amounting to a change of about 80 Hz per half-millimeter of bone loss) while for k=10 GPa the change is approximately 500 Hz. The 4 mm implant curves shown in FIG. 33B are substantially linear, however, there is an initial rapid decrease in stability during the first 0.5 mm of bone loss. This decrease in the first 0.5 mm was caused by the removal of the flange stiffness $K_F$ as material is removed from under it. This is more extreme than what likely occurs in practice, as the $K_F$ value used was larger than would be expected clinically. The removal of the flange was less significant in the 10 GPa case than when k=1 GPa. This is due to the underlying stiffness k being higher in the 10 GPa case, thus $K_F$ provides proportionally less stability than it does for the 1 GPa case. This indicates that as the supporting bone becomes stiffer, the effect of $K_F$ becomes less significant.

After the initial loss of $K_F$, the first mode sensitivity to bone loss shown in FIG. 33B decreases as the supporting stiffness increases. There is a change of about 100 Hz per half-millimeter of bone loss for the k of 1 GPa and 75 Hz per half-millimeter of bone loss for a k of 10 GPa. The 4 mm extraoral implants have a greater change in frequency per half-millimeter of bone loss as compared to the longer intraoral implants (100 Hz compared to 80 Hz in the first mode for a k of 1 GPa). This is not entirely unexpected, as it indicates that shorter implants are more sensitive to the loss of bone along their lengths than a longer implant.

Simulation of Flange Loss

Figure 34A:
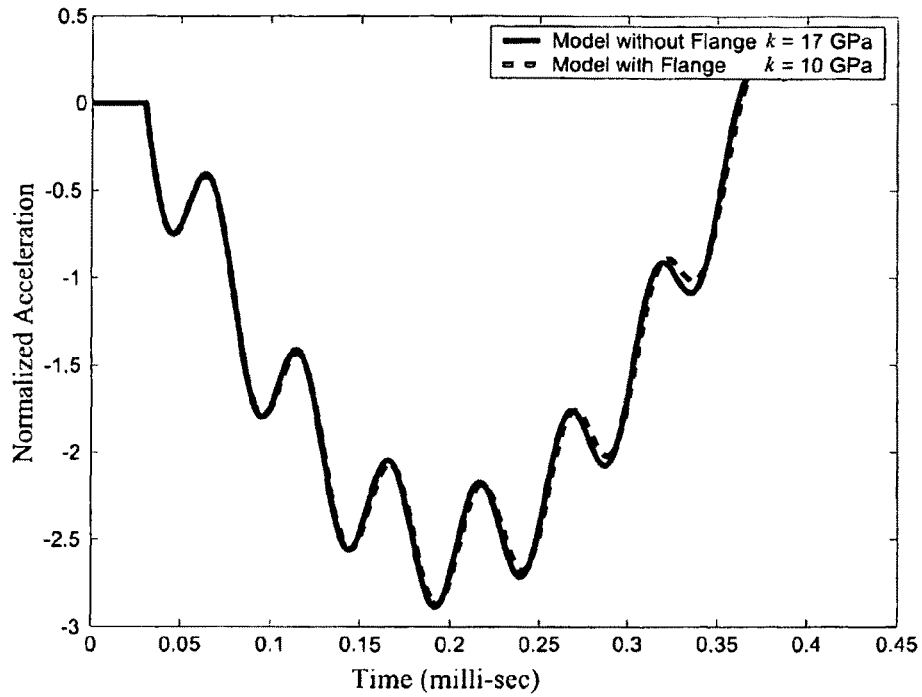
FIGS. 34A and 34B are graphs depicting model results with and without a flange at two different first mode frequencies.
Figure 34B:
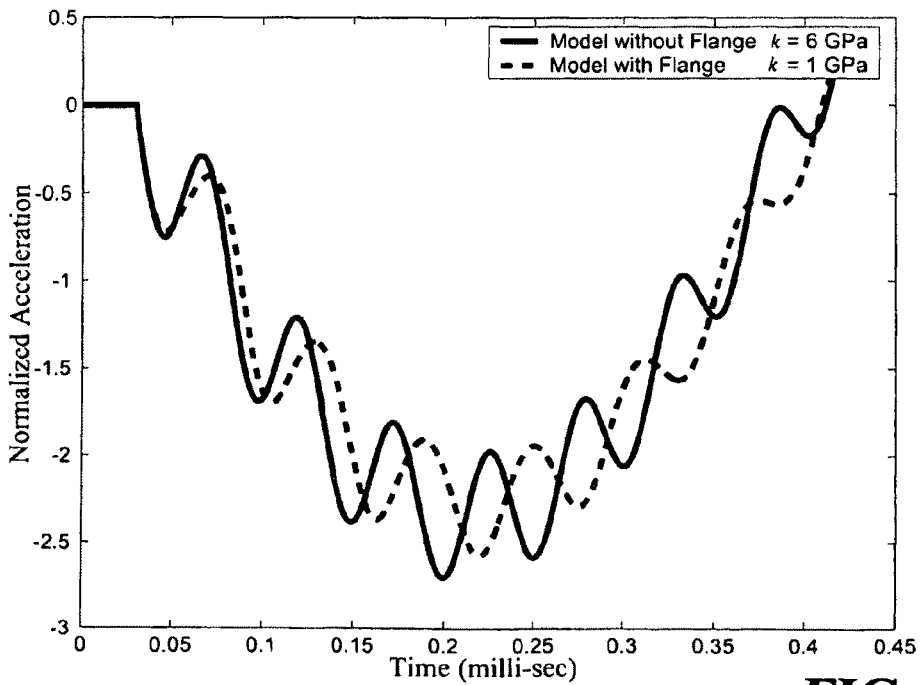

In the previous section, it was shown that the loss of the flange reduces the stability of the 4 mm extraoral flanged implant. It would be useful if the model could predict the effect of a flange in vivo based on the measured impact accelerometer response. The flange value used was $K_F$=3.65× $10^7$ N/m as determined in the model verification section. As discussed previously, this $K_F$ value represents a maximum flange contribution case with the flange fully bonded to the supporting surface. Clinically, the value of $K_F$ would likely fall between either no flange support or the maximum $K_F$ value. To this end, the model acceleration response for a 4 mm extraoral implant with a 10 mm abutment was compared with and without a flange at two different first mode frequencies as shown in FIG. 34. The two frequencies were chosen to represent a stable implant measurement (1500 Hz) and a less stable implant measurement (1300 Hz). FIG. 34A shows the model predictions for stable implants which have higher measured first mode frequencies (1500 Hz). There is substantially no difference between the results with and without a flange, indicating that for more stable implants, the inclusion of a flange has a negligible effect on the model output response. However, for less stable implants (1300 Hz), as shown in FIG. 34B, there is a noticeable difference between the higher frequency component in the response for the flange and no-flange signals. This suggests that by comparing the measured results to the model predictions, it may be possible to determine the degree to which a flange is contributing to the overall stiffness of the system for less stable implants.

Conclusions

An analytical four-degree of freedom model was developed to aid in interpreting the response of different implant-abutment geometries during impact measurements. The model relates the resonant frequencies of the system to the supporting bone stiffness which was represented as a stiffness per unit length k (GPa). The analytical model includes a number of internal stiffness components to represent local deformations during impact and bending/flexibility about the implant-abutment joint. However, a correction factor of 0.26 was applied to the bending/joint flexibility equation. The correction factor is a likely result of the combination of the simplifying assumptions made to incorporate bending into the model, a non-idealized joint, and the complete absence of shear effects in the current analysis. While the 0.26 value was determined from matching model results to measurements for one specific geometry, it was held constant throughout all subsequent simulations on different length implants, different striking heights, and different abutment lengths. With this one modification a very high level of agreement with the measurements was obtained over a variety of geometric conditions.

Once validated, the model could evaluate the supporting material properties for implants based on un-filtered (raw) accelerometer impact measurements. Model estimates of the supporting stiffness in vitro found the average support stiffness of FRB-10. modeling material to be 7.5-7.7 GPa which is comparable to the 9.3 GPa modulus of elasticity.

Model results were compared to measured in vitro cases over a range of implant-abutment geometries. The predicted response showed good agreement with a number of in vitro measurements demonstrating that the internal stiffness components in the system could not be ignored and had to be included to accurately reflect the system dynamics. The model internal stiffness parameters were determined based on tests on a limited number of Nobel Biocare implant/abutment systems. As there are presently a large number of different implant/abutment designs available, these parameters may have to be evaluated for these different implant systems. The agreement between the analytical model acceleration response and the in vitro testing indicated that the high frequency component found in the accelerometer signal was a second mode of vibration of the system.

Model simulations were then used to predict the effect of changes in the stiffness (k) on the first mode resonant frequency measurements. The model simulations demonstrated that for support stiffness values greater than approximately 5 GPa the first mode frequency becomes less sensitive to changes in the supporting stiffness. This indicates that due to the stiffness inherent in the implant/abutment system, there is an upper limit to the support stiffness that the impact measurement can effectively distinguish. However, for these values the implant is generally considered healthy, so the changes which may occur in k are of lesser importance. Model simulations were then used to show that damping changes affect the amplitude of the accelerometer signal, particularly the second mode, while having little influence on the implant system's resonant frequencies. Current dynamic mechanical testing methods that measure contact time or resonant frequency (such as the Osstell and Periotest) are relatively insensitive to changes in the damping properties. The effects of bone loss from the top of the implant were modeled. Both the 10 mm intraoral implant and 4 mm extraoral flanged implant were found to be sensitive to bone loss. The sensitivity to bone loss decreased for both implants as the support stiffness increased. The 4 mm extraoral flanged implant was also shown to be more sensitive to bone loss than the longer 10 mm intraoral implant.

Finally, the model was used to predict the effect the flange has on implant stability and to determine if it would be possible to use the model as a diagnostic tool in evaluating the effect of the flange in vivo. For implant systems with higher first mode frequencies, where the implant is considered healthy, the model was not able to distinguish between the flange and no-flange condition. However, if the implant is less stable the model does show significant differences in the predicted measurement responses between the flange and no-flange conditions. For these "less stiff" cases it may be possible to estimate how much stability is being provided by the flange and how much is due to the supporting bone.

The developed analytical model, in conjunction with the impact measurements, can allow direct estimation of the bone properties that support implants. Model simulations show the impact testing technique to be sensitive to bone loss and stiffness changes that would correspond to poorly integrated implants (ones that may be in danger of failing). Similarly, for implants with very stiff support, little useful quantitative data can be obtained about the bone supporting the implant, as the stiffness of the other components of the system dominate the response. However, such implants are generally considered healthy.

Note that simpler models (e.g. three-degree of freedom model) can easily be derived from the four-degree of freedom model. For instance, in the event that the abutment 52 and the implant 51 are part of the same rigid component (i.e. they are not separate components), then a simpler model could be derived by assuming $K_T$ to be infinite. In practical implementations, $K_T$ can be given a very large value instead of an infinite value. Other derivatives of the four-degree of freedom model are possible.

Section III: Impacting Particulars

Introduction

Adherence to a strict clinical protocol is used to yield reproducible results. One of the advantages of the use of an impact technique—its flexibility—is also a disadvantage in that used incorrectly it may give inconsistent or spurious results that have no clinical value. This is believed to be one of the reasons for the large variations in results reported in the literature. It appears that one of the major factors causing inconsistent results is uncontrolled clinical variables.

The repeatability and reproducibility of the current measurement scheme when measuring the same implant/abutment system were discussed earlier with reference to FIG. 13. This figure also highlights the fact that the results are even more consistent for an individual test (small error bars for any given column), and suggests that when the impacting rod is re-aligned even in a controlled laboratory setting, variability is added to the results (difference between columns). This highlights the importance of a strict protocol to maximise the precision of the measurement.

Method of Conducting an Impact Test

Figure 35:
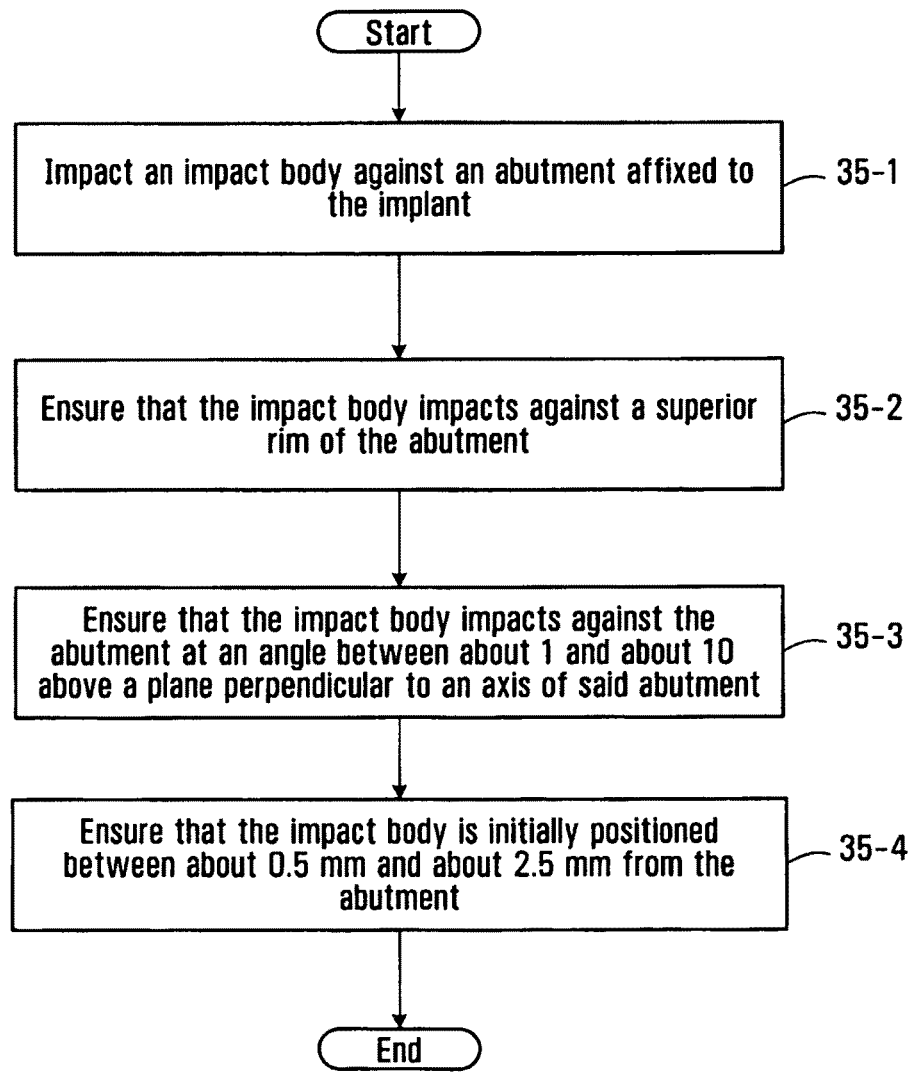
FIG. 35 is a flowchart of an example method of conducting an impact test.

Referring now to FIG. 35, shown is a flowchart of an example method of conducting an impact test. This method includes steps carried out by a person, such as a dentist or a clinician, for using the impact test for example on a patient. Note that this method can be applied to a plurality of different implant/abutment systems, or to a single implant/abutment system to assess the integrity of the implant interface over time.

At step 35-1, the person impacts an impact body against an abutment affixed to the implant. According to an embodiment of the invention, at step 35-2 the person ensures that the impact body impacts against a superior rim of the abutment. If the person always impacts the impact body against the superior rim of the abutment, then there is consistency in using the impact test. Note that the superior rim of the abutment is typically easy to identify and therefore the person can achieve success in consistently impacting against this portion. Alternatively, the person ensures that the impact body impacts against another portion of the abutment, provided that the person consistently impacts against the same portion.

For any given implant system, impact test readings will by meaningful (and comparable) if that implant system is consistently struck at the same spot. That way impact test results over time can be compared to see how the interface is changing/progressing. Note that the "same spot" does not need to be the same for different implant systems (but when abutments are involved the superior rim is a logical choice). For different artificial teeth systems, the consistent spot may be slightly different among these systems, depending on the details of each system. However, within a given implant system, in order to compare results over time the same consistent spot should be used.

In some implementations, as indicated at step 35-3, the person ensures that the impact body impacts against the abutment at an angle between about 1° and about 5° above a plane perpendicular to an axis of said abutment. In some implementations, as indicated at step 35-4, the person ensures that the impact body is initially positioned between about 0.5 mm and about 2.5 mm from the abutment.

Note that the method described above assumes that each implant is at least partially embedded in a medium and has an abutment connected thereto. It is to be understood that the "each implant . . . having an abutment connected thereto" does not necessarily mean that the abutment and the implant are formed of separate members. In some implementations, the abutment and the implant are formed of a same continuous member. In this manner, although the abutment and the implant are referred to separately, they are still part of the same continuous member. In other implementations, the abutment and the implant are formed of separate members.

In some implementations, when the abutment and the implant are formed of separate members, they are threaded attached. There are many ways that the abutment and the implant can be threaded attached. In some implementations, they are threadedly attached with a torque applied to the abutment that exceeds about 10 Ncm. Other implementations are possible.

The present invention "ensures" that the impact test is performed in a manner that can yield accurate results. Previous approaches do not ensure that the impact body impacts against a superior rim of the abutment. Rather, they typically provide no guideline, which can result in inaccurate results. The present invention includes specific guidelines for adherence in order to achieve acceptable results. These specific guidelines come from results of experimentation, details of which are provided below.

Experimentation

An experimental apparatus was used to evaluate several clinical variables that potentially could affect the readings. These variables include:

handpiece distance from abutment,
abutment torque,
striking height (position along the abutment where contact is made), and
angulation of handpiece.

To evaluate the effect of these variables, one variable was changed while attempting to hold all other variables constant. Measurements were done by striking the top rim of the abutment in each of these cases.

Handpiece Distance from Abutment

Figure 36:
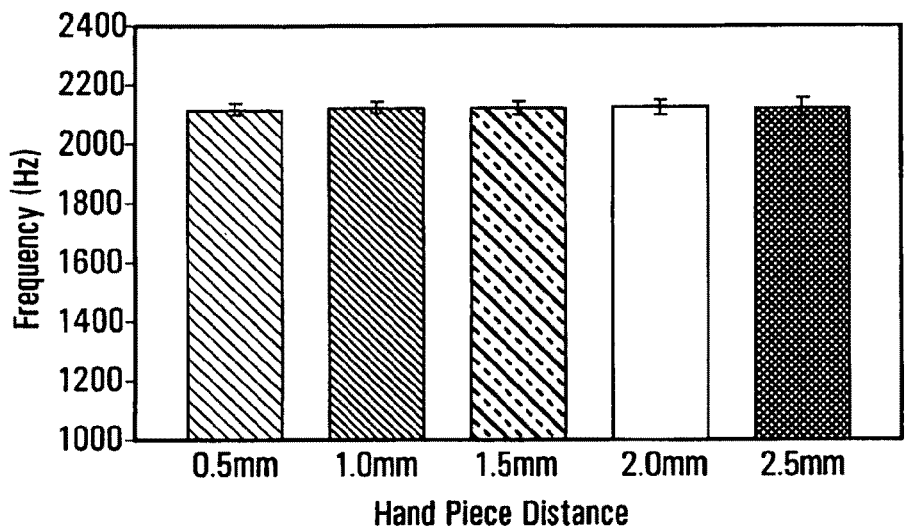
FIG. 36 is a chart depicting natural frequency as a function of the distance of the Periotest handpiece from the abutment.

Referring now to FIG. 36, shown is a chart depicting natural frequency as a function of the distance of the Periotest handpiece from the abutment. For these readings, measurements were taken at distances of 0.5, 1.0, 1.5, 2.0, and 2.5 mm from the 4 mm implant/5.5 mm abutment system. Five readings were taken at each of these distances then the handpiece was re-aligned and the readings were repeated for a total of three separate trials.

The mean value for the 0.5 mm distance was 2121±25 Hz while the reading at 2.5 mm was 2116±36 Hz. It should be noted that for the 2.5 mm readings the Periotest did not produce a PTV value, however a resonant frequency was obtained from the moving average filtered acceleration data. The Periotest instructions recommend that the handpiece be held a distance of 0.5 to 2.0 mm from the object being measured. The distance of the handpiece from the abutment was shown to have little influence on the resonant frequency. As long as the initial distance from the handpiece tip to the abutment tip was between 0.5 and 2.5 mm there were practically no differences noted.

Abutment Torque

Figure 37:
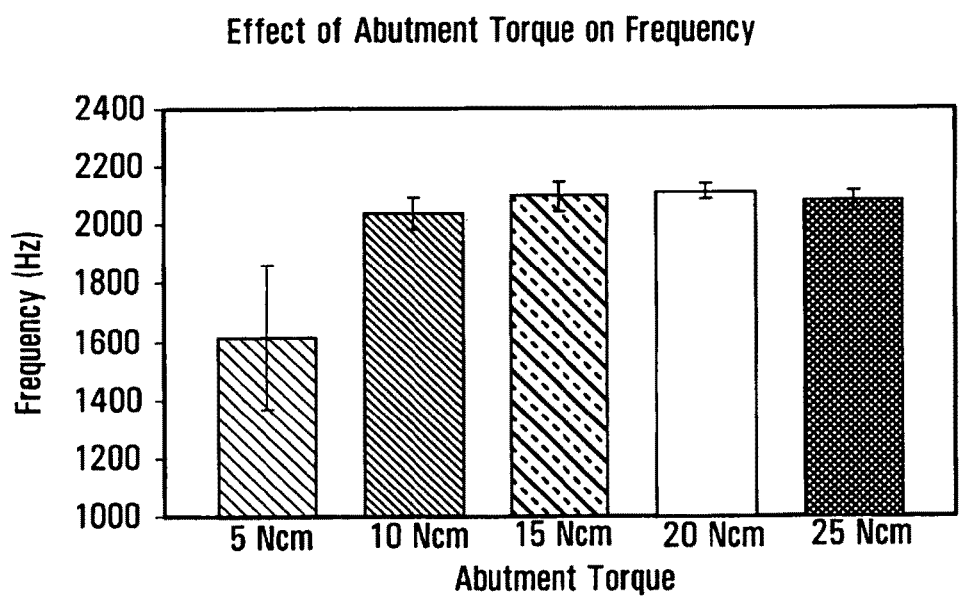
FIG. 37 is a chart depicting natural frequency as a function of abutment torque.

Referring now to FIG. 37, shown is a chart depicting natural frequency as a function of abutment torque. For these readings, a 5.5 mm abutment was torqued to the 4 mm implant system at 5, 10, 15, 20, and 25 Ncm. Five consecutive measurements were done at each of these values. Torque values were measured with a TorsionMaster Testing System (MTS Systems Corp, Eden Prairie, Minn., USA). Three separate trials at each of the torque values were conducted.

The 5 Ncm torque (which was noticeably loose) had the lowest resonant frequency reading of 1615 Hz and the largest standard deviation of 248 Hz. The torque applied when mounting a standard 5.5 mm abutment has little effect on the resonant frequency for torques above 10 Ncm. The torque applied to the abutment when mounted to the fixture had a large effect on the resonant frequency until the torque exceeded approximately 10 Ncm. For torques below this value, which are rarely encountered clinically, the reduced stiffness of the joint caused a large reduction in the resonant frequency of the system. This effect has been reported previously based on PTV values. For torques greater than 10 Ncm, the resonant frequency remained substantially unchanged. The most consistent results (lowest standard deviation in the readings) occurred at a torque of 20 Ncm. It should be noted that this threshold torque (over which no change occurred) was for an Entific system implant and standard 5.5 mm abutment. The effect of varying torque on other implant/abutment systems could vary depending on the details of the thread surfaces and length of the abutment (length of threaded screw).

Vertical Striking Height

Figure 38:
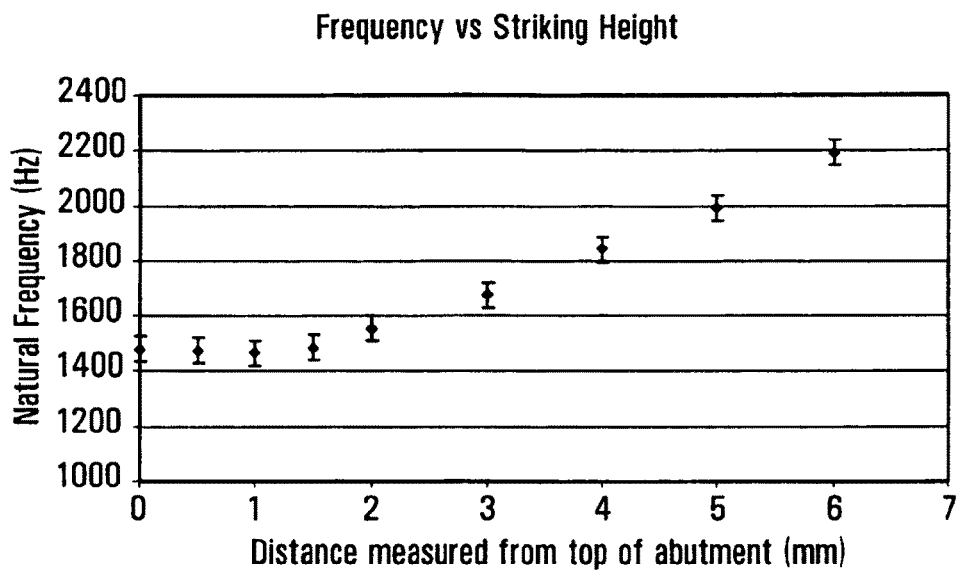
FIG. 38 is a chart depicting natural frequency as a function of striking height.

Referring now to FIG. 38, shown is a chart depicting natural frequency as a function of striking height. This shows a very significant effect that striking height has on the resonant frequency. While there was very little change in the frequencies when the handpiece was moved up to 1.5 mm from its initial position, there was a noticeable difference between the 1.5 mm and 2 mm positions, and beyond.

For these readings, a 10 mm abutment replaced the 5.5 mm abutment used in previous measurements, since a 10 mm abutment allowed for a greater variation of the striking height. Measurements were taken striking the top of the abutment and then lowering the handpiece distances of 0.5, 1, 1.5, 2, 3, 4, 5, and 6 mm. Five readings were taken at each height. The handpiece was re-aligned and the readings were repeated for three separate trials.

The position at which the impacting rod strikes the abutment (striking height) can have a very pronounced effect on the resonant frequency. FIG. 38 shows that a 3 mm variation results in a change to the resonant frequency of 194 Hz (13%). However, FIG. 38 also shows that there was effectively no change in the resonant frequency when the rod is moved up to 1.5-2.0 mm from its initial position. This is due to the fact that the impacting rod is 2 mm in diameter, and since it was hitting the rim of the abutment in its original position, it could move up to 2 mm (depending on its exact initial position) before it started striking a point below the top rim of the abutment. As long as some portion of the Periotest rod struck the rim of the abutment little variation in the results occurred.

As the effect of striking height on the resonant frequency is considerable, it is recommended that the impacting rod always strike the superior rim of the abutment, a point that is clinically easy to identify and a point that allows a ±1 mm variation when centred, without significantly changing the results.

Angulation of Handpiece

Figure 39:
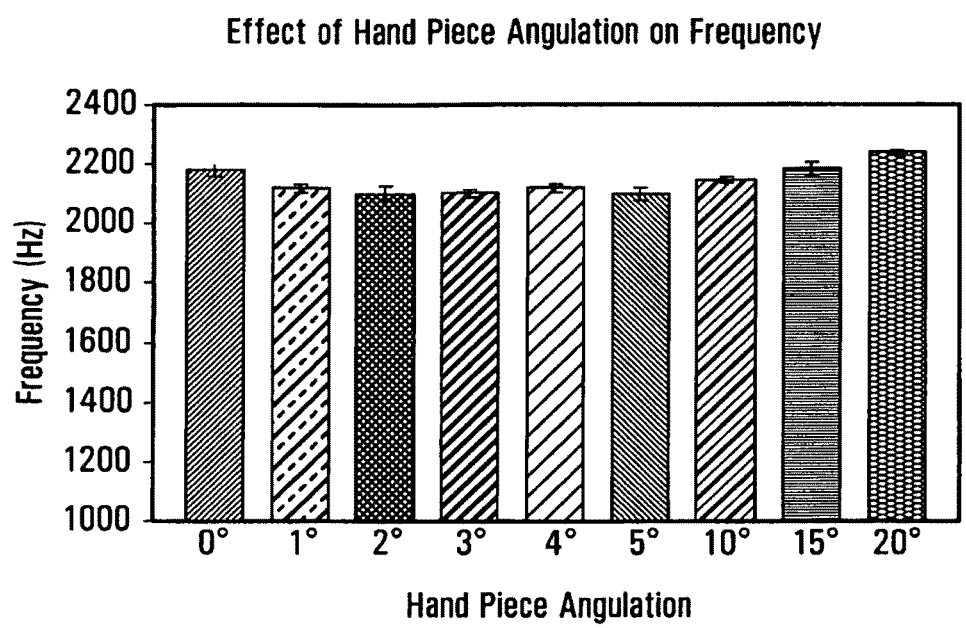
FIG. 39 is a chart depicting natural frequency as a function of handpiece angulation.

Referring now to FIG. 39, shown is a chart depicting natural frequency as a function of handpiece angulation. For these readings, five consecutive readings were done at 0°, 1°, 2°, 3°, 4°, 5°, 10°, 15°, and 20° such that 0° corresponds to when the handpiece is perpendicular to the abutment. Measurements were done on the 4 mm implant with the 5.5 mm abutment. This process was then repeated for three separate trials.

A handpiece angulation from 0°-20° caused the resonant frequency of the system to change from 2178±19 Hz to 2236±10 Hz. The results at 0° are noticeably different from the 1° readings, while the results are more consistent between 1° and 5°. Note that the Periotest instructions recommend an angulation of ±20° from the horizontal. This range is significantly greater than 1° to 5°.

When kept within a 1° to 5° range, no substantial differences were evident. There was, however, a noticeable difference between the 0° and 1° measurements. This difference is likely due to the fact that when the handpiece is nominally perpendicular to the striking surface it is not certain which part of the 2 mm diameter rod is striking the abutment. If the lower edge of the rod strikes the abutment this results in a higher frequency reading than if the top part of the rod strikes (effectively there is a change in striking height as the rim of the abutment is not being contacted). To eliminate this, a slight angulation of the handpiece is advisable. As angulation increases to 10° and beyond there is a trend of increasing resonant frequency.

Thus, the inconsistent and insensitive results reported when using the Periotest for measuring implants may result from both the techniques used to analyse the accelerometer signal and from clinical variations that occur during measurements. Utilising a moving average filtered signal and a stricter measurement protocol, it is believed that the impact technique can provide a reliable and sensitive diagnostic means to monitor implant stability.

Section IV: Patient Study

Introduction

In vivo testing was done in conjunction with the Craniofacial Osseointegration and Maxillofacial Prosthetic Rehabilitation Unit (COMPRU), located at the Misericordia Community Hospital, Edmonton, Alberta, Canada. All testing was approved by the University of Alberta Health Research Ethics Board and patients signed an informed consent form prior to taking part in the study.

The patient study group included 12 patients (8 males and 4 females) with a mean patient age at time of implant placement of 53 years (range 27-75 years). Patients enrolled in the study were treated with bone anchored hearing aid (Baha) implants which were left to heal for 3 months before the patients received their hearing processors. To have been considered for the study the patients:

had to be 18 years of age or older, had to meet audiological criteria for selection into the Baha program, had to be able to maintain a skin penetrating abutment, could not have any condition that could jeopardise osseointegration (e.g. malignancy in the temporal region, radiation therapy of the temporal region, undergoing chemotherapy), and had to be able to understand and read English.

Following a one-stage procedure, 12 flanged extraoral implants (3.75 mm, SEC 002-0, Entific Medical Systems, Toronto, Ontario, Canada) were placed (one per patient). The implants for 11 of the patients were 4 mm in length while one patient received a 3 mm implant. Implants were installed on either the right or left side, based on the audiological recommendation.

Clinical Protocol

An in vivo protocol was developed prior to patient measurements based on previously completed in vitro measurements (submitted for publication, Swain, R. et al., International Journal of Oral & Maxillofacial Implants, 2006):

The handpiece would be aligned so that the impacting rod would strike the superior rim of the abutment.

The handpiece should be held with a slight angulation (1 to 5 degrees) from a line perpendicular to the longitudinal abutment axis.

To ensure the measurements were taken in a consistent azimuthal direction, the handpiece was oriented parallel to the longitudinal axis of the patient (i.e. handpiece pointed towards the patient's feet when lying flat).

Use of Calibration Block

Figure 40:
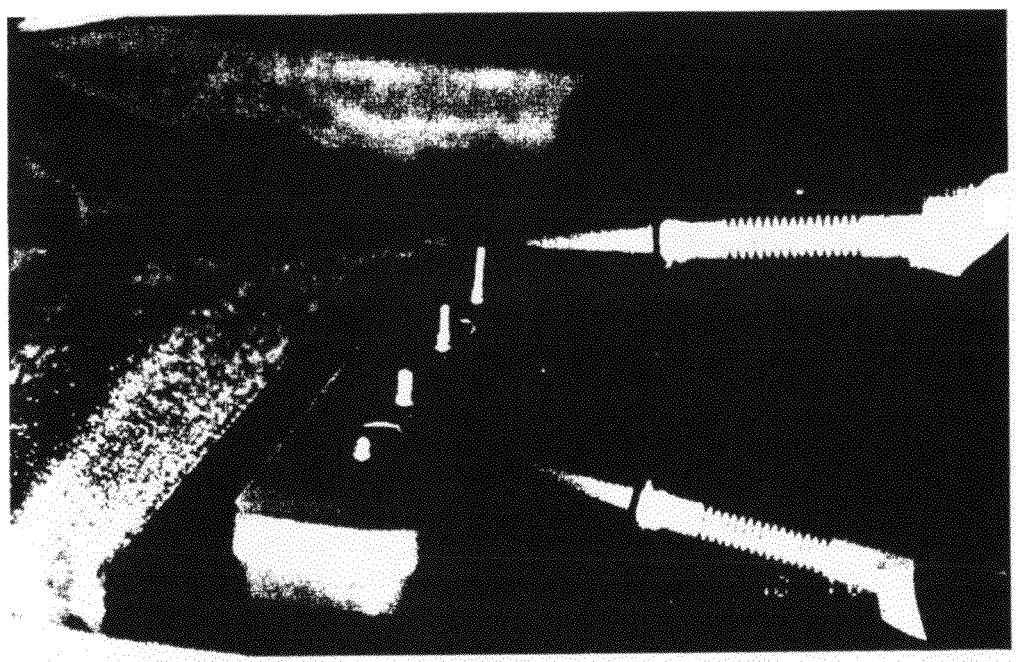
FIG. 40 is a photograph of a calibration block used during in vivo measurements.

Referring now to FIG. 40, shown is a photograph of a calibration block used during in vivo measurements. To ensure that the in vivo measurement values were as precise as possible, the calibration block was used. The block includes four aluminum posts with lengths of 4, 6, 8 and 10 mm threaded 4 mm into a rectangular piece of Photoelastic FRB-10 plastic (Measurements Group Inc, Raleigh N.C., USA). Epoxy was applied to the post threads during installation to provide a uniform interface and to prevent any loosening of the posts over time. The FRB-10 block was then mounted in a stainless steel base. For each aluminium post, there is a known natural frequency or other system property for the impact test.

Measurements were taken by the clinician on each of the four posts prior to the patient measurements as shown in FIG. 40. The clinician was instructed to align the impacting rod so that it would strike the superior rim of the post and with an angulation between 1 to 5 degrees. The calibration measurements included at least one impact measurement per post, with the measurement values being compared to the values engraved on the calibration block. The calibration block served two important purposes, it provided a method for evaluating if any longitudinal changes occurred in handpiece output, and it focused the operator on the proper measuring technique prior to the patient measurements.

In Vivo Measurements

In vivo measurements involved impact measurements with different abutment geometries at one patient visit as well as longitudinal patient readings over the course of one year after initial installation. To reduce any measurement inter-operator variability only one clinician conducted the measurements at all but implant installation. Due to the scheduling of the surgeries it was not always possible for the same clinician to be present during implant installation. In these cases, either another experienced clinician or the surgeon performed the calibration and measurements.

Measurements on Different Length Abutments

Two different length abutments were utilised in the study to test the consistency of the proposed measurement method and analytical model results for different implant-abutment geometries. Measurements were completed using standard 7 and 5.5 mm abutments (Nobel Biocare, Toronto, Ontario, Canada) for 10 of the twelve patients at the one year patient visit (the multiple abutment measurement was missed for 2 patients). Three impact measurements were completed on each of the abutments, which were affixed to the implant with a torque of 20 Ncm. After 3 impact measurements on the 5.5 mm abutment the 7 mm was connected to the implant and three additional measurements were taken.

Longitudinal Impact Measurements

The in vivo longitudinal study involved three impact measurements for each patient at implant installation and then at 1, 2, 3, 6 and 12 month scheduled patient visits. The measurements were completed during the patient's regularly scheduled visits to minimise additional time commitments. The impact measurements were taken using 5.5 mm standard abutments (Nobel Biocare, Toronto, Ontario, Canada) coupled to the implants with a torque of 20 Ncm.

Impact Accelerometer Signal Analysis

The impact signals utilised were from the Periotest handpiece, which had been modified to permit improved signal processing to be used with the accelerometer signal. Each separate impact measurement consisted of a series of 16 impacts (therefore 3 measurements would consist of 48 total impact events). The accelerometer signals were collected with an Instrunet analog/digital model 100 sampling system with a sampling rate of 167 kHz connected to a Toshiba Satellite A10 laptop computer.

The impact signals were used in conjunction with an analytical model to determine the interface stiffness and damping properties in vivo. The interface stiffness value, k, is calculated for each measurement and is reported in units of GPa. Damping properties are represented as a damping ratio. To examine the support an implant flange provides in vivo, measurement results (which included the flange) were compared to analytical model results with and without a flange for each of the patients.

The in vivo impact measurements collected in this study are interpreted using an analytical model, which provides a quantitative measure of the bone/implant interface stiffness and damping. In addition, the analytical model provides a means of evaluating the support the implant flange provides.

Impact Signal Analysis With and Without a Flange

Figure 41A:
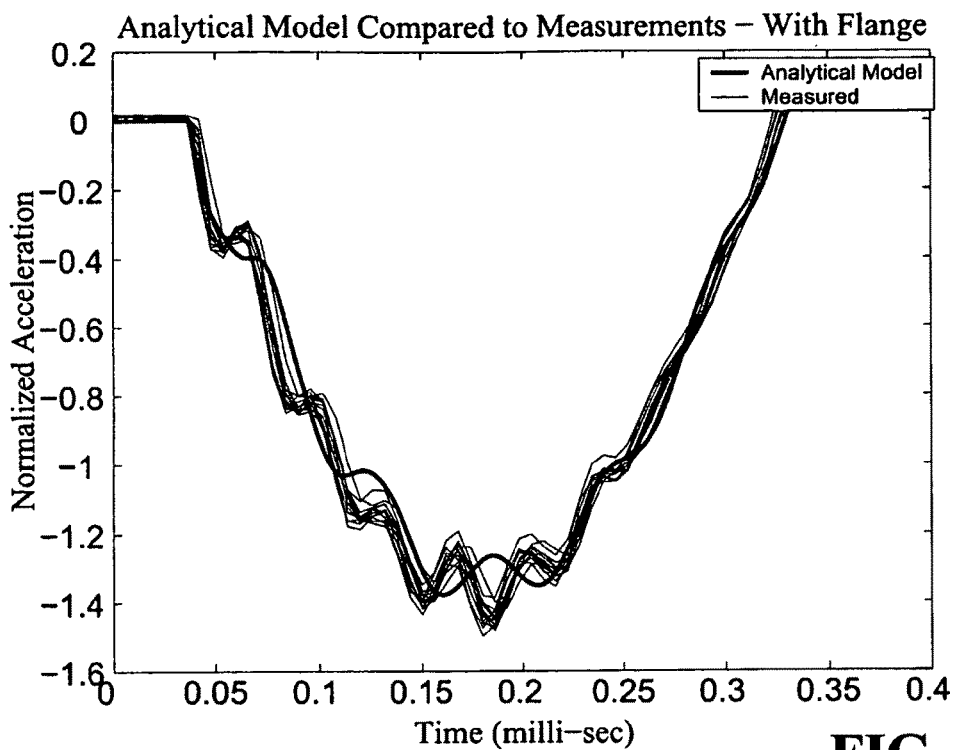
Figure 41B:
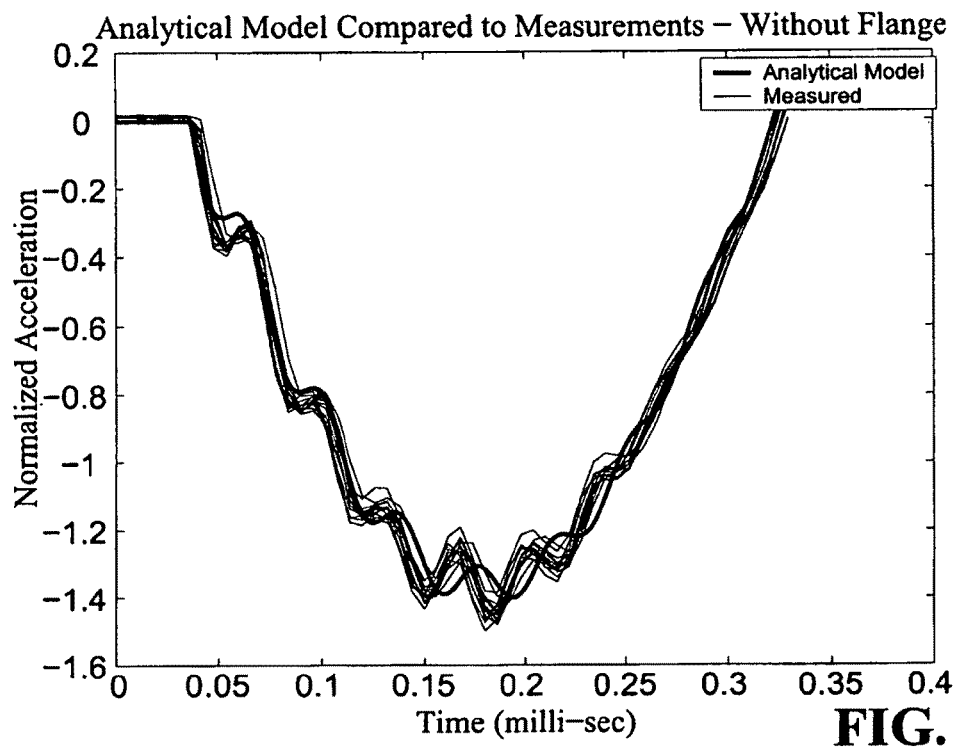

While the theoretical impact response with and without a flange was compared to the measured impact response for all patients, a representative example of this comparison for 16 measured impact responses (as each measurement consists of 16 impacts) is shown in FIGS. 41A and 41B. FIG. 41A shows the comparison with a flange, while FIG. 41B shows the comparison without a flange. If the number of peaks in the measured impact signal are compared to the simulations with a flange (FIG. 41A) and without (FIG. 41B), the predicted response without a flange can be seen to more closely resemble the measurements.

Figure 42:
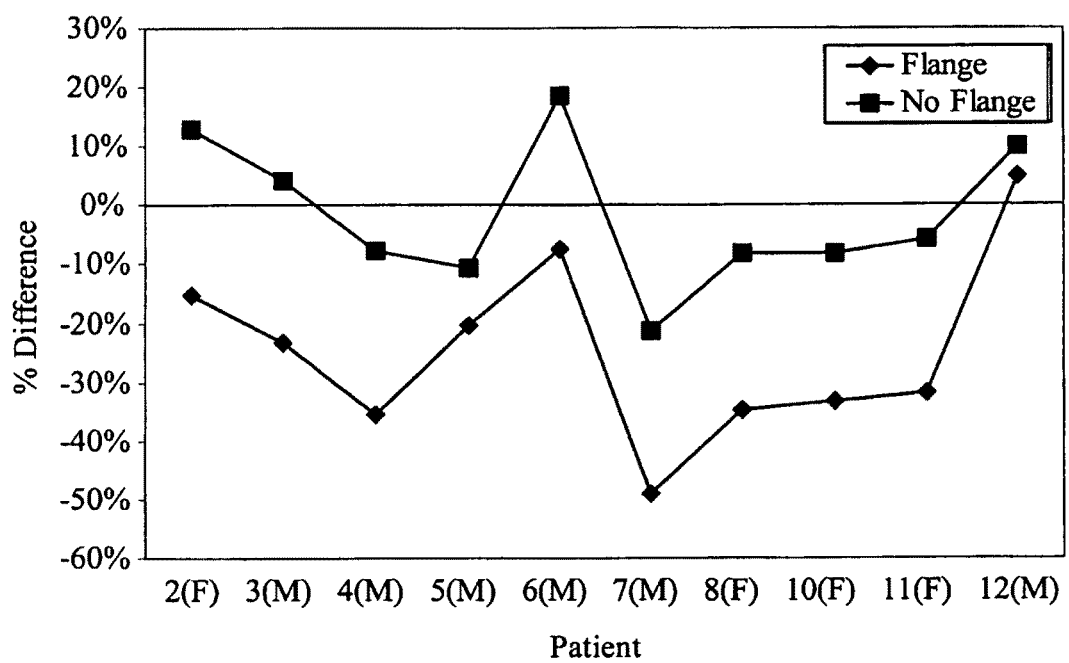
FIG. 42 is a graph depicting percent difference in predicted interface stiffness for two different abutment geometry measurements with and without a flange for 10 patients.

The interface stiffness, k, was calculated with and without a flange providing support for the measurements on the different abutment geometries. The percent differences between the stiffness values calculated for the 5.5 and 7 mm abutments with and without a flange for 10 of the patients are shown in FIG. 42. Note that multiple abutment measurements were missed on patients 1 and 9 and therefore data for these patients has been omitted. The percent difference is defined as the difference between the interface stiffness for the 7 and 5.5 mm abutments divided by the interface stiffness determined using the 5.5 mm abutment. As shown the model estimations with a flange tended to have larger differences in interface stiffness for the different abutment geometries. In addition, the differences for the flanged case are generally biased while the no flange results yield both positive and negative differences.

The calculated interface stiffness without the effects of a flange for the two different length abutments for each patient are shown in Table 6. The patient number and gender is included in the first column. The interface stiffness is shown in the table as a range, with the stiffness value corresponding to the average measurement shown in parenthesis after the range. The percent difference between the interface stiffness for the two abutments is shown in the last column.

TABLE 6

In Vivo interface stiffness values for a 5.5 mm and 7 mm abutment on the same patient

| Patient | 5.5 mm Abutment k (GPa) | 7.0 mm Abutment k (GPa) | % Difference |
|---|---|---|---|
| 1 (F) | — | — | — |
| 2 (F) | 3.7-4.0 (3.8) | 4.1-4.5 (4.3) | 13% |
| 3 (M) | 2.1-2.5 (2.3) | 2.2-2.7 (2.4) | 4% |
| 4 (M) | 4.5-5.0 (4.7) | 3.5-5.6 (4.4) | −8% |
| 5 (M) | 9.2-56.8 (16.1) | 12.4-17.1 (14.4) | −11% |

TABLE 6-continued

In Vivo interface stiffness values for a 5.5 mm and 7 mm abutment on the same patient

| Patient | 5.5 mm Abutment k (GPa) | 7.0 mm Abutment k (GPa) | % Difference |
|---|---|---|---|
| 6 (M) | 2.1-3.0 (2.5) | 2.5-3.5 (2.9) | 19% |
| 7 (M) | 8.8-13.1 (10.6) | 5.4-14.8 (8.3) | −21% |
| 8 (F) | 6.3-7.1 (6.7) | 5.7-6.5 (6.1) | −8% |
| 9 (M) | — | — | — |
| 10 (M) | 6.0-8.9 (7.2) | 6.2-7.1 (6.0) | −8% |
| 11 (F) | 5.5-6.1 (5.8) | 5.1-5.9 (5.5) | −6% |
| 12 (M) | 5.7-8.9 (7.0) | 7.4-8.1 (7.7) | 10% |

Figure 43A:
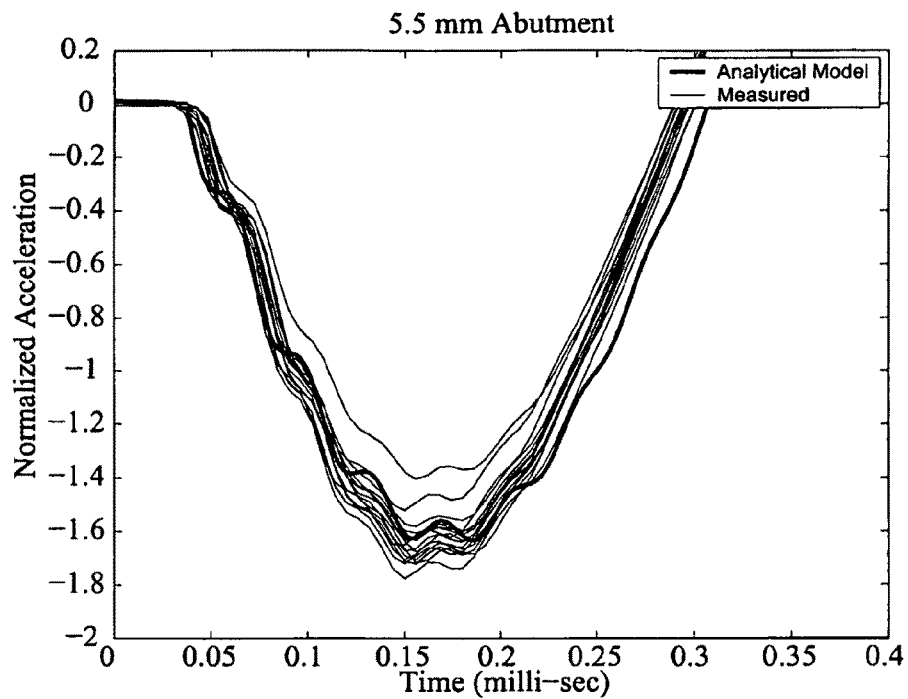
FIGS. 43A and 43B are graphs comparing impact measurements with predicted model response at the 12 month measurement with two different abutment lengths and no flange support.
Figure 43B:
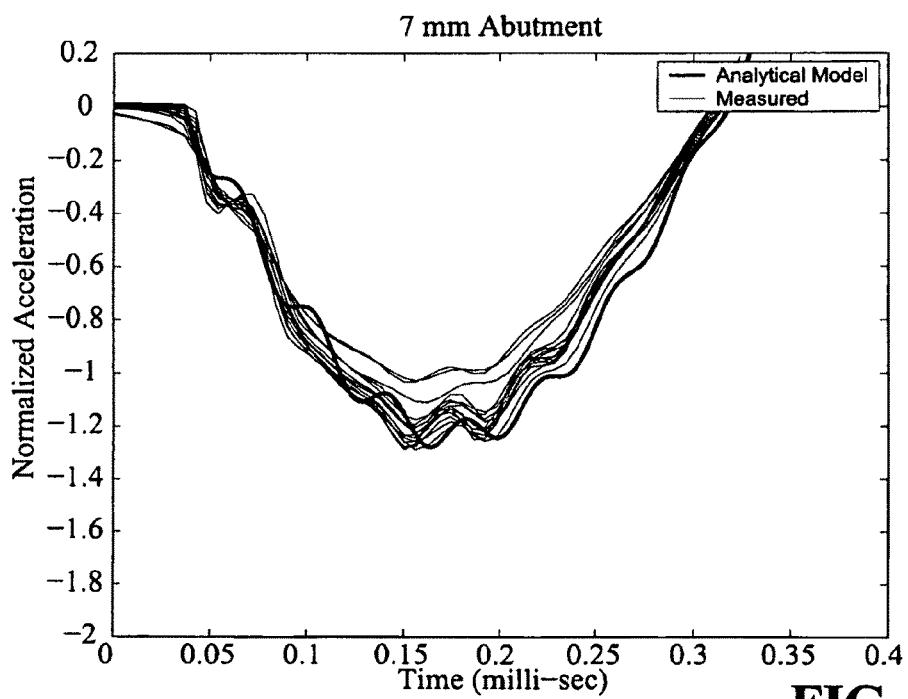

The theoretical impact response is compared to the measured impact responses for a representative patient (Patient 4) in FIGS. 43A and 43B. FIG. 43A shows the comparison using a 5.5 mm abutment, while FIG. 43B shows the comparison using a 7 mm abutment. The predicted impact response can be seen to match the measured responses quite well for both abutment geometries.

Longitudinal Changes in Interface Stiffness

Figure 44:
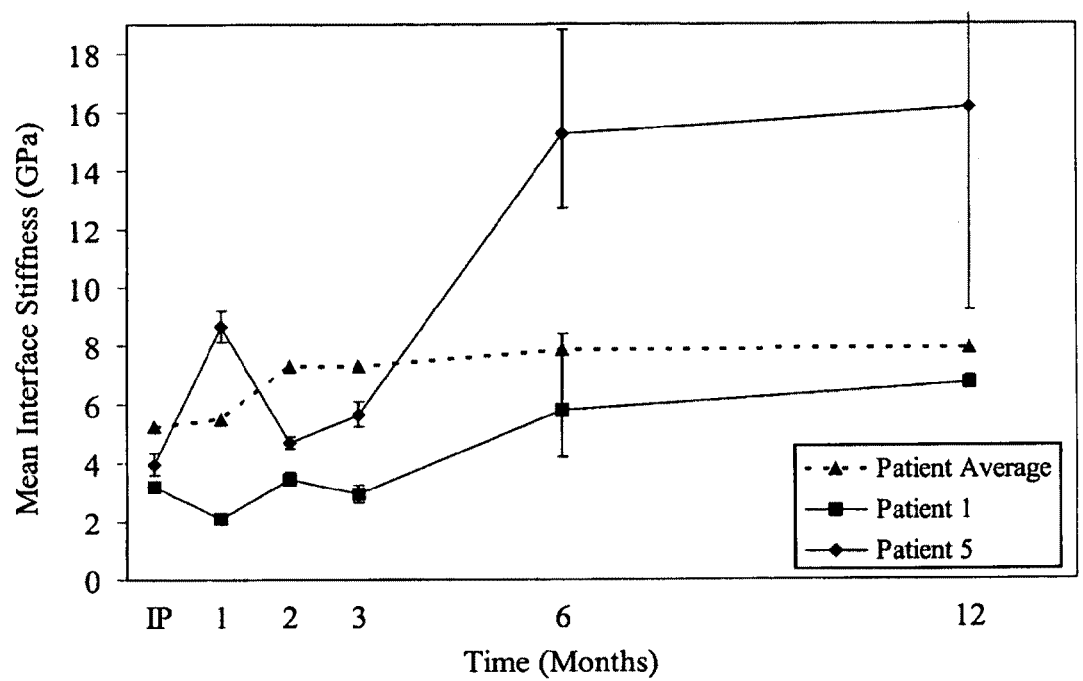
FIG. 44 is a graph depicting average longitudinal interface stiffness based on all patients compared to individual interface stiffness results.
Figure 45A:
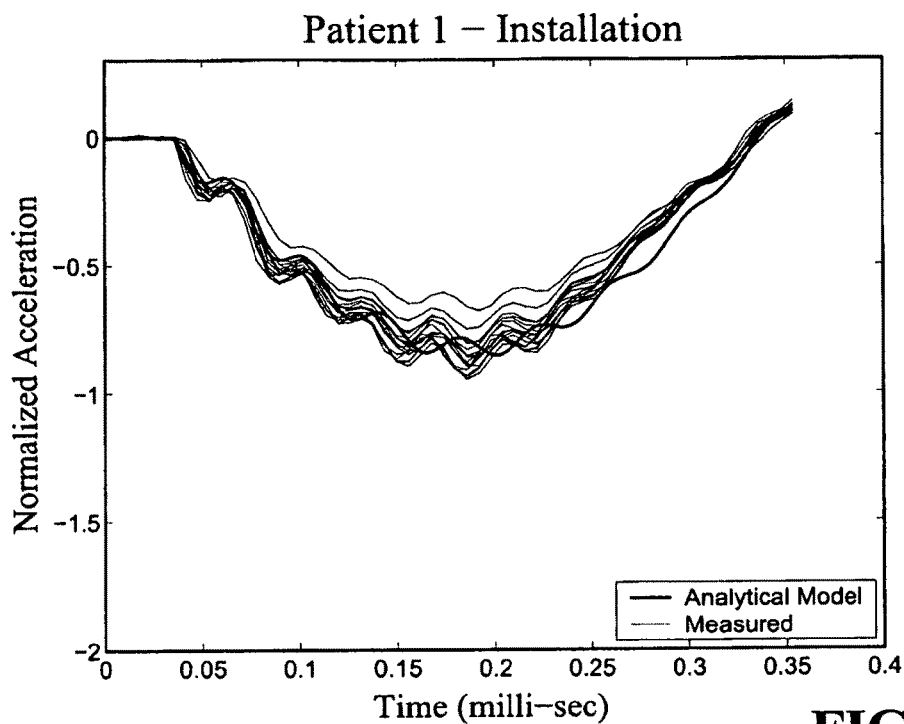
FIGS. 45A to 45F are graphs comparing acceleration measurement to predicted model response at different,patient visits for a patient.
Figure 45B:
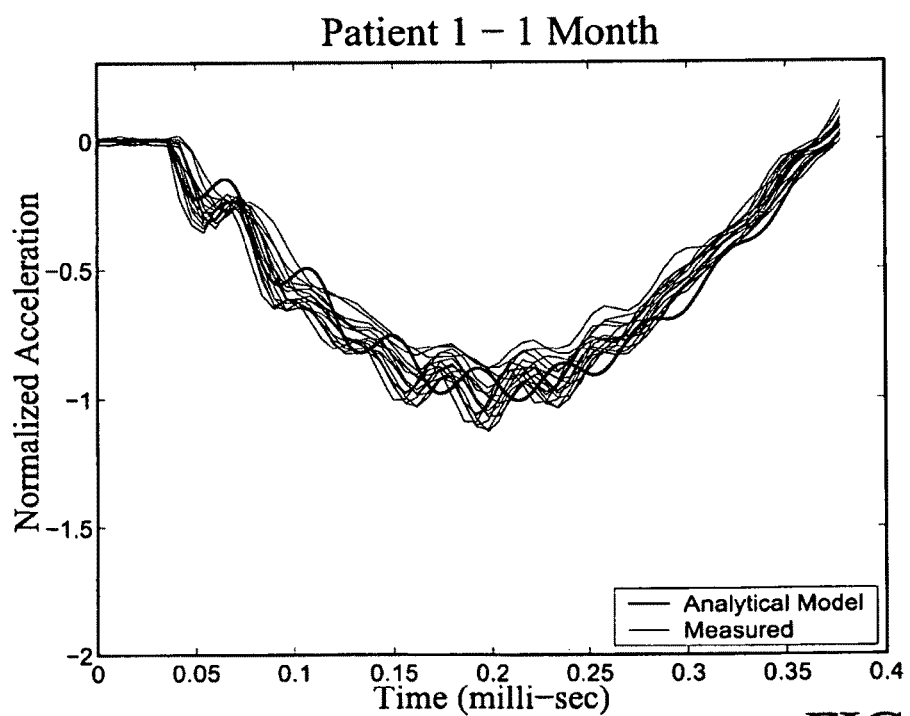
Figure 45C:
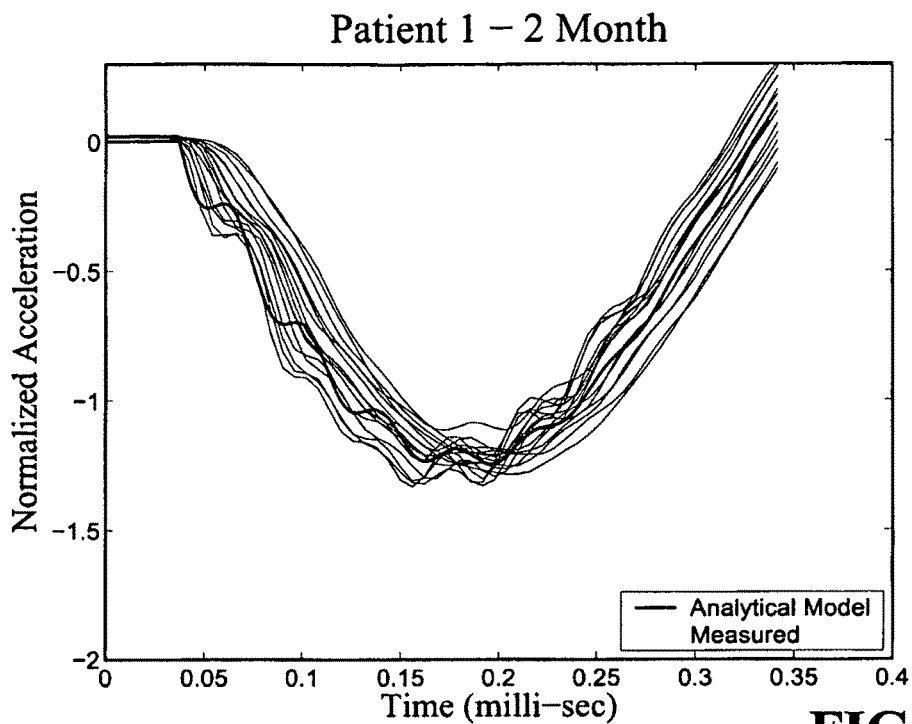
Figure 45D:
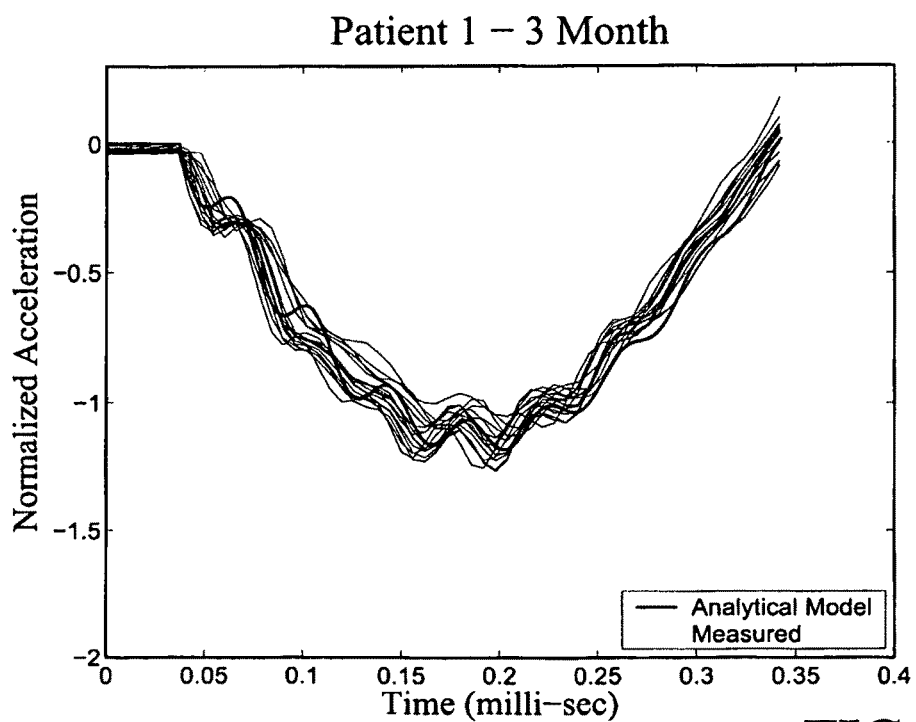
Figure 45E:
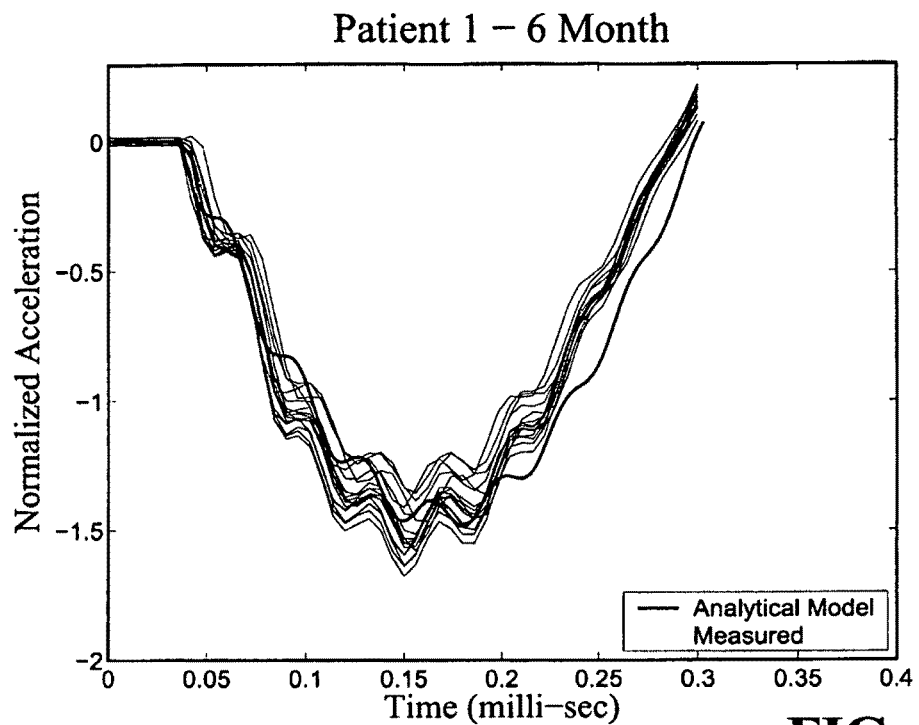
Figure 45F:
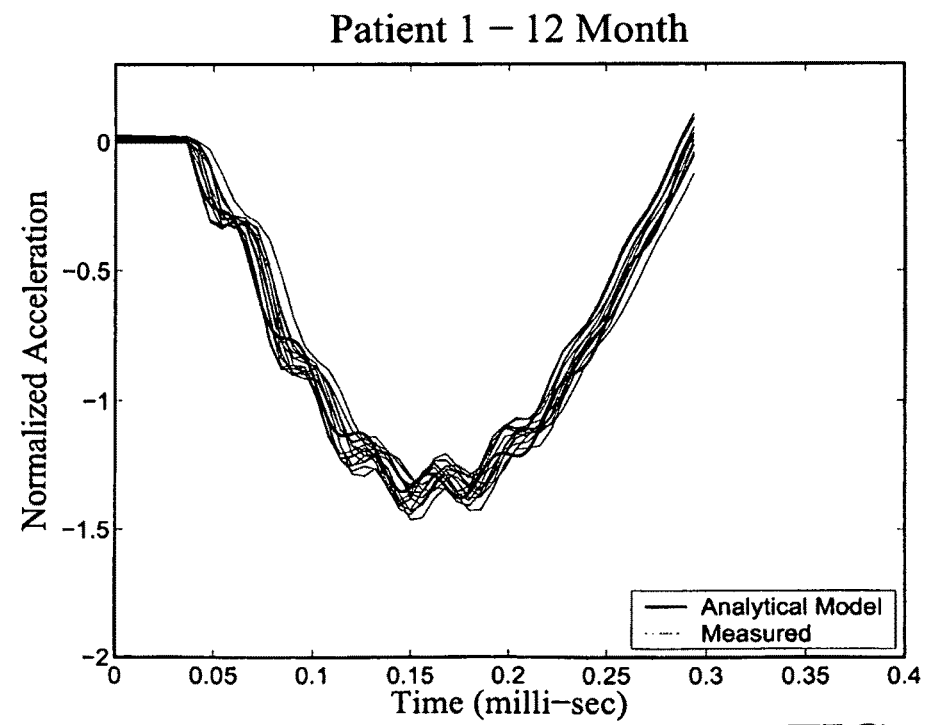
Figure 46A:
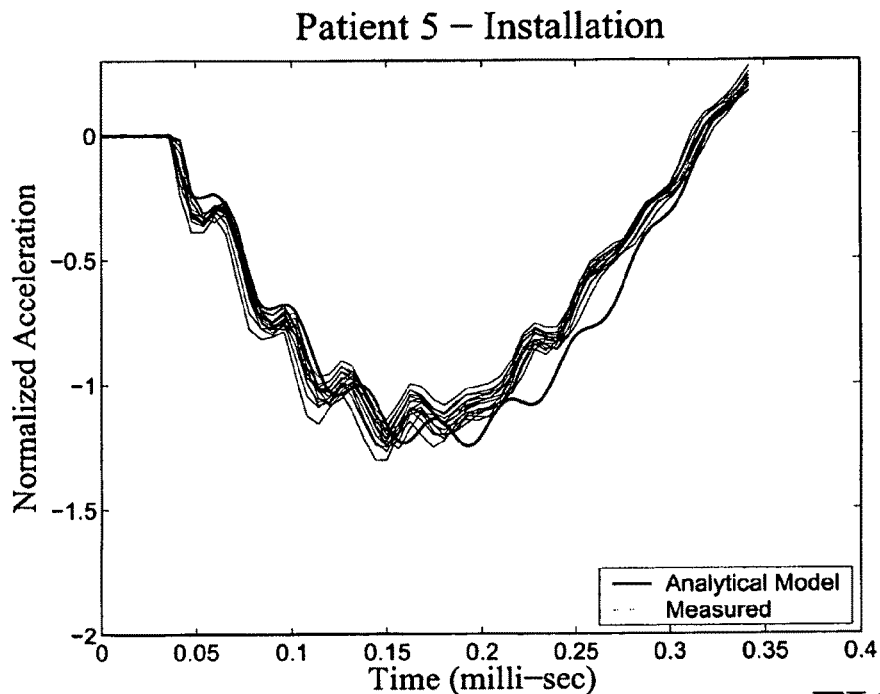
FIGS. 46A to 46F are graphs comparing acceleration measurement to predicted model response at different patient visits for another patient.
Figure 46B:
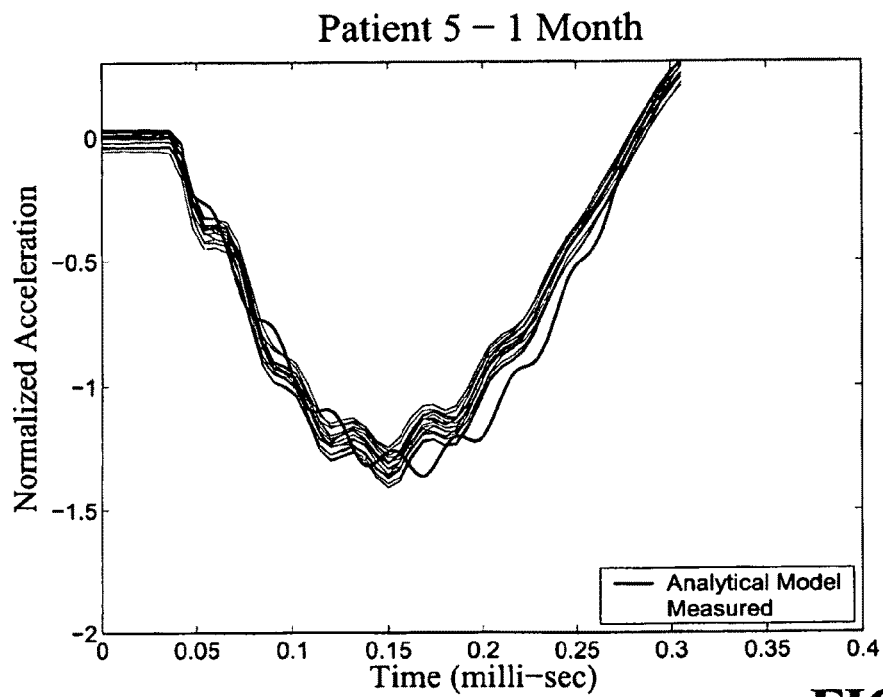
Figure 46C:
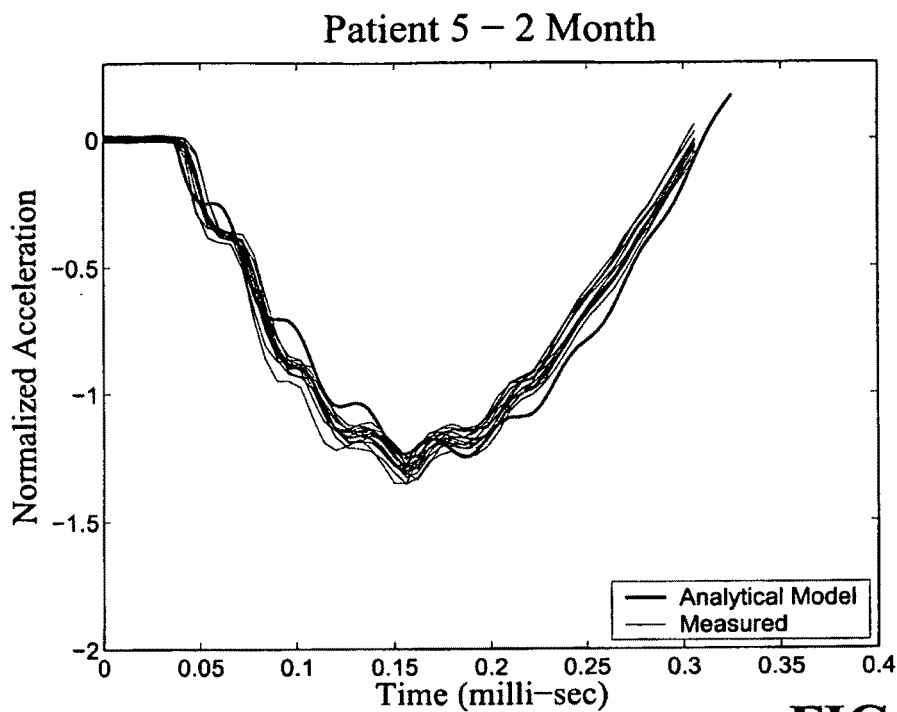
Figure 46D:
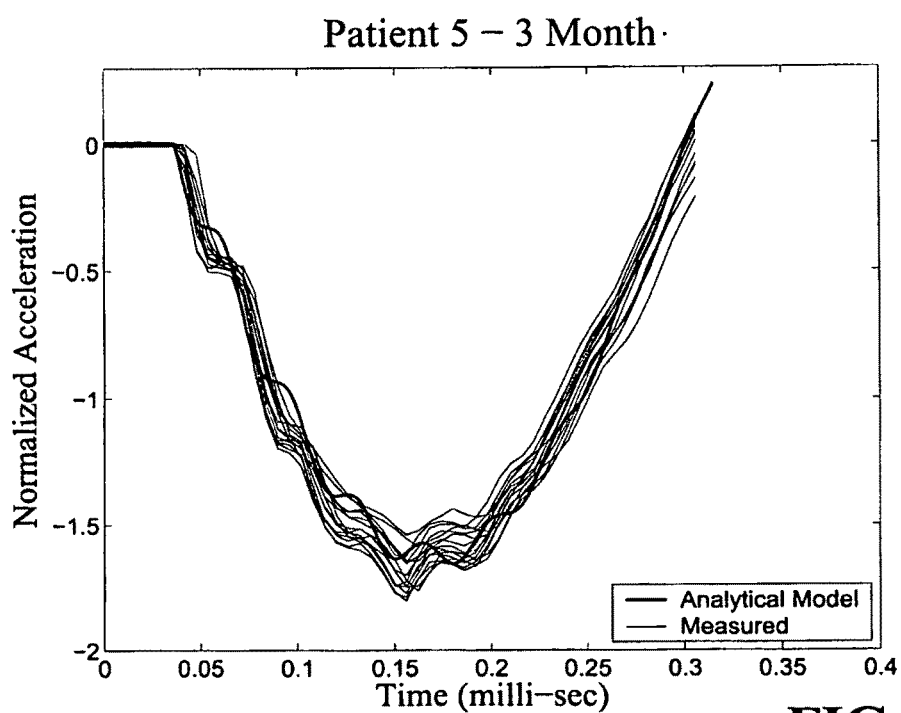
Figure 46E:
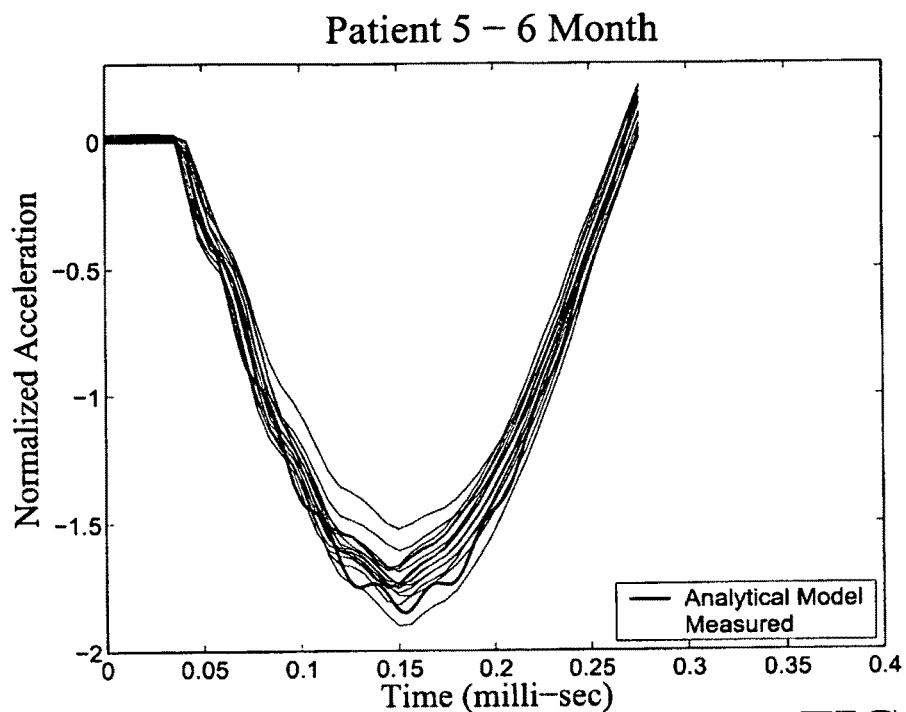
Figure 46F:
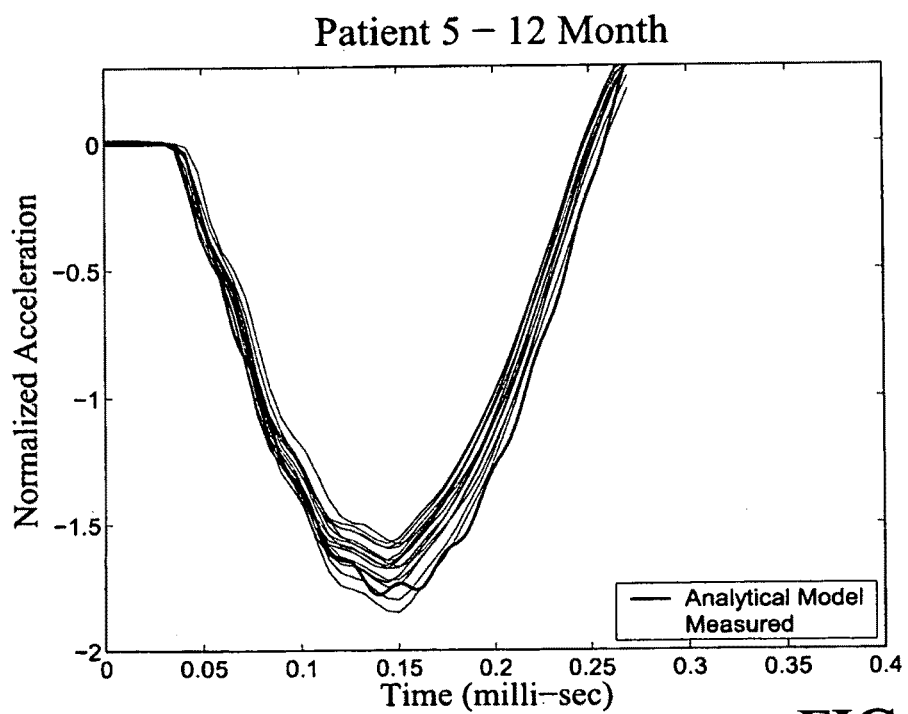

As shown in FIG. 44, the mean interface stiffness for all patients at time of implant placement was 5.2 GPa with a similar measurement of 5.5 GPa after one month. The mean stiffness increased to 7.3 GPa between the one month and two month measurements before stabilising for the remaining measurements. No implants failed during the course of the study. Individual patients showed distinctly different patterns from the mean as demonstrated by the results for Patients 1 and 5 (see FIG. 44). While the initial interface stiffness for the two patients are similar, the stiffness decreased in the first month for Patient 1 while it increased in the first month for Patient 5. The stiffness then decreases at the second month measurement for Patient 5 while increasing in the second month for Patient 1. Both patients see an increase in interface stiffness between 3-6 months and end at significantly different stiffness values at 12 months (16.1 GPa for Patient 5 compared to 6.7 GPa for Patient 1).

The longitudinal interface stiffness estimated by the model for all 12 patients are shown in Table 7. As the analytical model takes into account changes in system geometry, the stiffness values shown for Patient 2 can be directly compared to the other patients although the implant length was different (i.e. 3 mm implant as compared to 4 mm implant for the other patients).

TABLE 7

Interface stiffness values (GPa) based on impact measurements at installation, 1 month and 2 months for 12 patients fitted with Baha implants

| Patient | Installation | 1 Month | 2 Month | 3 Month | 6 Month | 12 Month |
|---|---|---|---|---|---|---|
| 1 (F) | 3.1-3.3 (3.2) | 2.0-2.2 (2.1) | 3.3-3.7 (3.5) | 2.7-3.3 (3.0) | 4.2-8.4 (5.8) | 6.5-6.9 (6.7) |
| 2*(F) | 4.8-5.2 (5.0) | 1.8-1.9 (1.9) | 3.1-3.9 (3.5) | 3.2-3.4 (3.3) | 4.0-4.1 (4.1) | 3.7-4.0 (3.8) |
| 3 (M) | 1.5-2.2 (1.8) | 2.0-2.2 (2.1) | 2.7-3.2 (2.9) | 3.8-4.6 (4.2) | 3.7-3.9 (3.8) | 2.1-2.5 (2.3) |
| 4 (M) | 3.1-5.7 (4.1) | 4.5-5.2 (4.8) | 4.9-5.6 (5.3) | 3.0-3.7 (3.3) | 6.5-6.6 (6.5) | 4.5-5.0 (4.7) |
| 5 (M) | 3.6-4.4 (4.0) | 8.1-9.2 (8.6) | 4.5-4.9 (4.7) | 5.2-6.1 (5.7) | 12.7-18.8 (15.2) | 9.2-56.8 (16.1) |
| 6 (M) | 7.6-11.1 (9.1) | 1.6-1.8 (1.7) | 2.1-2.4 (2.2) | 1.5-1.6 (1.5) | 3.1-3.4 (3.3) | 2.1-3.0 (2.5) |
| 7 (M) | 6.5-11.8 (8.6) | 10.8-14.1 (12.3) | 10.0-13.7 (11.6) | 28.6-29.1 (28.8) | 12.7-20.0 (15.6) | 8.8-13.1 (10.6) |
| 8 (F) | 2.5-3.2 (2.8) | 2.3-2.7 (2.5) | 2.9-3.1 (3.0) | 3.6-3.7 (3.7) | 4.2-4.4 (4.3) | 6.3-7.1 (6.7) |
| 9 (M) | 8.7-11.2 (9.9) | 4.6-13.1 (7.2) | 30.6-38.9 (313) | 10.8-20.1 (14.3) | 6.6-7.5 (7.1) | 18.5-25.9 (21.6) |
| 10 (M) | 6.6-9.4 (7.8) | 11.8-12.4 (12.1) | 6.5-6.7 (6.6) | 6.3-11.8 (8.4) | 11.1-17.8 (13.8) | 6.0-8.9 (7.2) |
| 11 (F) | 2.6-4.0 (3.2) | 3.6-4.6 (4.1) | 3.3-3.5 (3.4) | 4.2-4.3 (4.3) | 7.3-8.2 (7.7) | 5.5-6.1 (5.8) |
| 12 (M) | 3.4-3.6 (3.5) | 5.6-7.6 (6.5) | 6.1-6.9 (6.5) | 6.9-7.2 (7.1) | 6.0-8.6 (7.1) | 5.7-8.9 (7.0) |

*Patient with a 3 mm implant (all other patients have 4 mm implants)

Examples of the model predicted impact responses compared to the measured impacts over the one year time period for Patient 1 are shown in FIGS. 45A to 45F. Results for Patient 5 are shown in FIGS. 46A to 46F.

Longitudinal Changes in Interface Damping In addition to the stiffness properties the damping of the supporting bone was estimated for each patient at each scheduled visit by utilising the analytical model to interpret the impact responses. Across all Baha patient measurements the amount of damping present in the supporting bone was found to vary longitudinally, however, the amount of change and overall magnitude of the damping was very low, with the damping ratio for the first mode ranging between 0.04-0.43%.

Discussion

While in vitro measurements with a flange bonded to the supporting materials surface provided support for the implant the results displayed in FIGS. 41 and 42 indicate that the model simulations including flange support do not provide as consistent interface stiffness results as those which assume the flange offers no support. When model results were compared to measurements across all the patients (as was done for one patient shown in FIG. 41) the results without the flange tended to be in much better agreement with the measurements. These results are reinforced in FIG. 42 where the differences in the model estimations for the same implant with different abutment geometries tended to be larger when a flange stiffness was included in the simulations. Further to this, the differences for the simulations without a flange oscillate between positive and negative values while the differences with a flange appear to have a bias. This bias appears systematic when the flange is assumed to offer stability to the implant and indicates that the flange may not be providing significant support in vivo. Since the underlying interface stiffness doesn't change when the different abutments are placed on the implant the differences plotted ideally should be zero. While the results without a flange in FIG. 42 match the ideal case better than the results including the effects of a flange, some differences do exist. From the data shown in Table 6, the largest percent difference was 21% across the patients and the smallest was 4%. For all but one patient (Patient 2) the difference in the estimated interface stiffness values for the different abutment geometries could be explained by the measurement variation (the range of stiffness values for the two abutment geometries overlap). This indicates that, overall, the analytical model provides an effective means of removing apparent changes in measurements due to changes in geometry.

As the results from FIGS. 41 and 42 indicate that the flange does not appear to provide significant support to the implant in patients, the following discussion will concentrate on model results without any flange contribution to the implant stability. The validity of this assumption is further demonstrated when the predicted impact response is compared directly to measurements such as those shown in FIG. 43. The magnitudes and frequency components of the signals are relatively well predicted, providing evidence that the interface stiffness values estimated from the model are realistic.

The longitudinal results shown in FIG. 44 indicate that while an average interface stiffness can be determined across all the patients at each time interval, the bone response due to implant placement can vary significantly between different individuals. Considering specifically Patients 1 and 5, while both start with similar interface stiffness, and while the average stiffness across all the patients only shows a 5% increase from installation to one month (5.2-5.5 GPa), the interface stiffness for Patient 1 decreased 34% and the interface stiffness increased for Patient 5 by 118%. The changes in interface stiffness for all the patients is summarised in Table 7. The difference between the one month response between patients may be due to differences in individual healing rates and the corresponding rate of bone modelling/remodelling at the implant interface. Additionally the longitudinal implant stability may be sensitive to the implant installation procedure. Slight differences in the drilling and tapping procedures may change how the bone responds to implant placement (this may be especially important in the short term).

Between the one month and two month measurements the average patient interface stiffness shown in FIG. 44 shows the largest increase (33%) then appears to stabilise for the remaining measurements. This contrasts sharply with the individual patient results shown, where the largest change in interface stiffness between measurements occurred between the three and six month measurements (with Patients 1 and 5 having a 97% and a 169% increases in this time interval). Seven of the twelve patients tested had more than a 20% increase in the interface stiffness between the three and six month patient measurements. The remaining patients either had little change or more than a 40% decrease in interface stiffness. The magnitude of interface stiffness changes indicates that for many patients the bone-implant interface may still be undergoing significant physiological changes between the three and six month time interval. Increases in stability may be the result of increased mineralization of new bone and increased direct bone contact at the interface. Changes occurring at the interface during this time period are further complicated by implant loading. Patients received their processors at the three month visit. In addition to any changes already in progress, the stresses caused from the load applied to the implant may have triggered an adaptive response in the bone around the implant.

Between the six and twelve month patient measurements there was a 16% and 6% increase in the bone-implant interface stiffness for Patients 1 and 5. The difference between six and twelve month stiffness for these two patients is considerably less than that found between the three and six month values. The difference between the installation and six month interval measurements is greater than the difference between the six month and twelve month values for ten of the twelve patients tested (as shown in Table 7). This may indicate that for these patients the majority of the stiffness changes at the implant interface occurred within the first six months. This falls in the 4-12 month interval cited by Roberts in which secondary mineralization of new bone and increased direct bone contact at the interface occurs and the remodelling of the non-vital interface and supporting bone is completed.

When the predicted model impact response is compared directly to patient measurements as in FIGS. 45 and 46, the response appears similar to the measurements. The longitudinal changes in the impact signal reflects changes in the bone properties occurring at the implant interface. Agreement between the predicted impact results and measurements demonstrates the analytical model's ability to accurately evaluate the interface properties. While overall agreement between measurements and predicted responses is quite good, the patient measurements occurring at the twelve month intervals tended to have better agreement with model predictions than earlier measurements. This is likely due to the assumption in the model that the interface stiffness is uniform along its length. At implant placement the interface may differ along the length of the implant depending on the gaps between the implant threads and the surrounding bone. The greater levels of agreement at later stages seems to indicate that the interface becomes more uniform over time.

Although the total number of patients included in the study is not large, there are some trends in the interface stiffness data that are noteworthy. The average stiffness at the twelve month measurement for the male patients was 9.0 GPa and 5.8 GPa for the females, with the top five twelve month stiffness values belonging to male patients. These interface stiffness values compare well to the Young's modulus of 13.4 GPa for cortical bone and 7.7 GPa for trabecular bone used in finite element simulations of the human skull. Overall, 67% of the patients had their lowest interface stiffness within the first month. Five of the patients had their lowest interface stiffness value at implant installation, with another three at the one month mark. By the third month, all but one patient had recorded their lowest interface stiffness value. From the stiffness values determined, the initial three month healing period appears to be when the implants are least stable. It has been suggested that the woven bone lattice that forms at the implant interface occurs within the first 0.5 months and that the woven bone cavities then fill with high quality lamellae gaining strength for load bearing within the first 0.5-1.5 months. The lower interface stiffness values during this time frame may correspond to the less stiff woven bone lattice and increases in stiffness after this point indicating the placement of the high quality lamellae.

Based on the tests completed, the current practice of processor connection and implant loading after three months appears reasonable. Loading implants during the period of initial instability may have negative consequences. There is a transition from primary mechanical stability (stability of old bone) to biologic stability (stability of newly formed bone). During this transition, there is a period of healing in which the initial mechanical stability has decreased but the formation of new bone has not yet occurred to the level suitable to maintain implant stability. It has been suggested that, at this point, a loaded implant would be at greatest risk of relative motion and would be (at least theoretically) most susceptible to failure of osseointegration.

Along with changes in the stiffness, it is believed that the damping properties of the bone changes as the implant osseointegrates. Some studies completed with the Periotest refer to the device as measuring the damping characteristics of the interface. While damping appears to be present in the measurements, the largest damping ratio across all patients during the testing was 0.43% (with damping ratios ranging from 0.04-0.43%). Damping ratio measurements below 0.43% indicate that there is very little damping present in bone supporting the Baha implants. There is such a small amount of damping present that if the damping is neglected entirely in the model it would have a negligible effect on the interface stiffness results presented. The low damping ratios calculated emphasise that the longitudinal changes in the measured impact response of the in vivo implants tested are caused primarily from changes in the interface stiffness and not from changes in the damping properties of the supporting bone.

Conclusions

The in vivo tests utilising the impact test and the analytical model provided longitudinal interface stiffness and damping values for twelve patients fitted with Baha implants. In vivo testing with two different abutment geometries demonstrated that the impact technique and analytical model can account for changes in implant system geometry. Model simulations with and without a flange indicated that for the patients in the in vivo study, the implant flange does not appear to significantly contribute to the implant stability.

Longitudinal model results show good overall agreement with the measured impact responses for the patients and provide a direct measure of the bone-implant interface stiffness and damping properties. The changes in interface stiffness values longitudinally varied significantly between patients, indicating that the bone response to implant placement is highly individualistic. Further research could be completed to investigate some of the possible causes for this variation. While the longitudinal changes in the supporting stiffness varied significantly between the patients, the male patients tended to have higher interface stiffness. The average bone-implant interface stiffness determined at the twelve month measurement was 9.0 GPa for the male patients and 5.8 GPa for the females. Additionally, the initial three month period appears to be when the implants have the lowest interface stiffness. The minimum interface stiffness values for 11 of the 12 patients occurred during this interval.

The interface damping properties were determined to be quite low, with the highest estimate being 0.43%. While the damping ratio for healthy Baha implants placed in the mastoid appears quite low, a failing implant may have considerably different damping properties particularly if scar tissue develops at the interface. For this reason, further study on the damping ratio in failing implants would be useful.

While the above discussion of the preferred embodiment of the invention was made in the context of tests conducted using a Periotest device, it is to be understood that the invention may be utilised with other impact-type implant integrity testing devices, as will be understood by persons skilled in the art. For example, the impact rod of the Periotest device may be replaced by other impact bodies such as bars or hammers. The means of accelerating the impact rod towards the implant may use electromagnets, springs, or other means.

The method of conducting the impact test is described as using a Periotest device on an abutment threadedly attached to an implant. It is to be understood that the test can be conducted on an abutment which is attached to the implant by other means, by being integral with the implant for example, as would be the case for natural dentition.

Numerous modifications and variations of the present invention are possible in light of the above teachings. It is therefore to be understood that within the scope of the appended claims, the invention may be practised otherwise than as specifically described herein.

We claim:

1. An apparatus for determining a property of an interface between a medium and an implant is at least partially embedded therein, the apparatus comprising:
   an input for receiving a signal generated from a motion of an impact body during impact with an abutment connected to the implant; and
   a property determiner for:
   (a) maintaining a mathematical model for impacting the impact body against the abutment, the mathematical model comprising a set of interrelated equations of motion for notional elements of the abutment, the implant, the medium, and the interface;
   (b) determining a system property from the signal; and
   (c) analytically determining the property of the interface by applying the system property to the mathematical model.

2. The apparatus for of claim 1, wherein the property of the interface is a measure of an integrity of the interface.

3. The apparatus of claim 1 further comprising:
   a filter for filtering the signal before determining the system property.

4. The apparatus of claim 3, wherein the filter is a zero-phase filter.

5. The apparatus of claim 4, wherein the zero-phase filter is a moving average filter.

6. The apparatus of claim 1, wherein the system property is a natural frequency.

7. The apparatus of claim 6, wherein the property of the interface is a measure of a stiffness of the interface, and analytically determining the property of the interface by applying the system property to the mathematical model comprises:
   determining a lowest natural frequency based on the signal; and
   determining the stiffness of the interface, k, that would produce the same lowest natural frequency based on the equation $|[K]-\omega^2[M]|=0$, wherein [M] contains constants that describe mass properties of each system element and [K] contains constants that describe stiffness of various system components including the stiffness of the interface.

8. The apparatus of claim 1, wherein the mathematical model comprises three-degrees of movement.

9. The apparatus of claim 1, wherein the mathematical model comprises four-degrees of movement.

10. The apparatus of claim 1, wherein the mathematical model comprises notional elements comprising:
    a rigid impact body;

a rigid abutment body beside the impact body;
a horizontal linear impact spring between the impact body and the abutment body;
a rigid implant body vertically below the abutment body;
a medium within which the implant body is at least partially embedded; and
a plurality of horizontal and vertical linear interface springs having distributive stiffness per unit length k between the implant body and the medium.

11. The apparatus of claim 10, wherein the mathematical model further comprises as a notional element:
a torsional spring between the abutment body and the implant body.

12. The apparatus of claim 10, wherein the mathematical model further comprises as a notional element:
vertical linear springs between an external flange of the implant and a surface of the medium.

13. The apparatus of claim 1, further comprising:
the impact body; and
a motion detector connected to the impact body for translating the motion of the impact body during impact into the signal.

14. A method of determining a property of an interface between a medium and an implant that is at least partially embedded therein, the method comprising:
maintaining a mathematical model for impacting an impact body against an abutment connected to the implant, the mathematical model comprising a set of interrelated equations of motion for notional elements of the abutment, the implant, the medium, and the interface;
receiving a signal generated from a motion of the impact body during impact with the abutment;
determining a system property based on the signal; and
analytically determining the property of the interface by applying the system property to the mathematical model.

15. The method of claim 14, wherein the property of the interface is a measure of an integrity of the interface.

16. The method of claim 14, further comprising:
filtering the signal using a filter before determining the system property.

17. The method of claim 16, wherein the filter is a zero-phase filter.

18. The method of claim 17, wherein the zero-phase filter is a moving average filter.

19. The method of claim 16, wherein the system property is a natural frequency.

20. The method of claim 19, wherein the property of the interface is a measure of a stiffness of the interface, and analytically determining the property of the interface by applying the system property to the mathematical model comprises:
determining the lowest natural frequency based on the signal; and
determining the stiffness of the interface, k, that would produce the same lowest natural frequency based on the equation $|[K]-\omega^2[M]|=0$, wherein [M] contains constants that describe mass properties of each system element and [K] contains constants that describe stiffness of various system components including the stiffness of the interface.

21. The method of claim 14, wherein the mathematical model comprises three-degrees of movement.

22. The method of claim 14, wherein the mathematical model comprise four-degrees of movement.

23. The method of claim 14, wherein the mathematical model comprises notional elements comprising:
a rigid impact body;
a rigid abutment body beside the impact body;
a horizontal linear impact spring between the impact body and the abutment body;
a rigid implant body vertically below the abutment body;
a medium within which the implant body is at least partially embedded; and
a plurality of horizontal and vertical linear interface springs having distributive stiffness per unit length k between the implant body and the medium.

24. The method of claim 23, wherein the mathematical model further comprises as a notional element:
a torsional spring between the abutment body and the implant body.

25. The method of claim 23, wherein the mathematical model further comprises as a notional element:
vertical linear springs between an external flange of the implant and a surface of the medium.

26. The method of claim 14, further comprising the further step of:
translating a motion of the impact body during impact into a signal.

27. A non-transitory computer readable medium having computer executable instructions stored thereon for execution on a processor to implement the method of claim 14.

* * * * *